US012767646B1

(12) United States Patent
Blackburn et al.

(10) Patent No.: US 12,767,646 B1
(45) Date of Patent: Oct. 20, 2026

(54) CRYSTALLINE FORMS AND PROCESSES FOR THE PREPARATION OF PYRIMIDINE DERIVATIVES USEFUL AS MODULATORS OF THE 5-HT2A SEROTONIN RECEPTOR

(71) Applicant: Arena Pharmaceuticals, Inc., New York, NY (US)

(72) Inventors: Anthony C. Blackburn, San Diego, CA (US); Jui-Chen Lin, San Diego, CA (US)

(73) Assignee: Arena Pharaceuticals, Inc., New York, NY (US)

( * ) Notice: Subject to any disclaimer, the term of this patent is extended or adjusted under 35 U.S.C. 154(b) by 345 days.

(21) Appl. No.: 18/702,970

(22) PCT Filed: Oct. 19, 2022

(86) PCT No.: PCT/IB2022/060059
§ 371 (c)(1),
(2) Date: Apr. 19, 2024

(87) PCT Pub. No.: WO2023/067520
PCT Pub. Date: Apr. 27, 2023

Related U.S. Application Data

(60) Provisional application No. 63/270,926, filed on Oct. 22, 2021.

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC .......................... C07D 403/12; C07B 2200/13
See application file for complete search history.

(56) References Cited

FOREIGN PATENT DOCUMENTS

| | | | |
|---|---|---|---|
| EP | 1264820 | A1 | 12/2002 |
| WO | 2007136703 | A1 | 11/2007 |
| WO | 2022093849 | A1 | 5/2022 |

OTHER PUBLICATIONS

International Patent Application No. PCT/IB2022/060059, filed Oct. 19, 2022, Search Report and Written Opinion mailed Jan. 20, 2023, (WO 2023/067520) published Apr. 27, 2023, 14 pages.

*Primary Examiner* — Sarah Pihonak
*Assistant Examiner* — Padmaja S Rao
(74) *Attorney, Agent, or Firm* — Young-In J. Oh

(57) ABSTRACT

The present disclosure relates to a crystalline form and crystalline salts of s of N-(3-(4,6-dimethylpyrimidin-5-yl)-4-(2-(pyrrolidin-1-yl)ethoxy)phenyl)cyclopropanecarboxamide (Compound Ia) and pharmaceutical compositions thereof that modulate the activity of the 5HT2A 5 receptor. The present disclosure further relates to processes useful in the preparation of crystalline form and salts of Compound Ia and pharmaceutical compositions thereof.

16 Claims, 27 Drawing Sheets

PXRD Diffractogram of Compound Ia (Crystalline Form)

PXRD Diffractogram of Compound 1a (Crystalline Form)

DSC Thermogram of Compound Ia (Crystalline Form)

TGA Thermogram of Compound 1 (Anhydrous Form)

PXRD Diffractogram of Compound Ia (Besylate Salt)

DSC Thermogram of Compound Ia (Besylate Salt)

TGA Thermogram of Compound Ia (Besylate Salt)

PXRD Diffractogram of Compound Ia (Citrate Salt)

DSC Thermogram of Compound Ia (Citrate Salt)

TGA Thermogram of Compound Ia (Citrate Salt)

PXRD Diffractogram of Compound Ia (Fumarate Salt)

DSC Thermogram of Compound Ia (Fumarate Salt)

TGA Thermogram of Compound Ia (Fumarate Salt)

PXRD Diffractogram of Compound Ia (Hydrochloride Salt)

DSC Thermogram of Compound Ia (Hydrochloride Salt)

TGA Thermogram of Compound Ia (Hydrochloride Salt)

PXRD Diffractogram of Compound Ia (Mesylate Salt)

DSC Thermogram of Compound Ia (Mesylate Salt)

PXRD Diffractogram of Compound Ia (Phosphate Salt)

DSC Thermogram of Compound Ia (Phosphate Salt)

TGA Thermogram of Compound Ia (Phosphate Salt)

PXRD Diffractogram of Compound Ia (Succinate Salt)

DSC Thermogram of Compound Ia (Succinate Salt)

TGA Thermogram of Compound Ia (Succinate Salt)

PXRD Diffractogram of Compound Ia (Tosylate Salt)

DSC Thermogram of Compound Ia (Tosylate Salt)

TGA Thermogram of Compound Ia (Tosylate Salt)

CRYSTALLINE FORMS AND PROCESSES FOR THE PREPARATION OF PYRIMIDINE DERIVATIVES USEFUL AS MODULATORS OF THE 5-HT2A SEROTONIN RECEPTOR

CROSS REFERENCE

This application is a National Stage Application under 35 U.S.C. § 371 of PCT/IB2022/060059, filed on Oct. 19, 2022, which claims the benefit of U.S. Provisional Patent Application No. 63/270,926, filed on Oct. 22, 2021, the disclosures of which are hereby incorporated by reference in their entirety.

The present disclosure relates to crystalline forms and salts of N-(3-(4,6-dimethylpyrimidin-5-yl)-4-(2-(pyrrolidin-1-yl)ethoxy)phenyl)cyclopropanecarboxamide (Compound Ia) and pharmaceutical compositions thereof that modulate the activity of the 5-$HT_{2A}$ serotonin receptor. The present invention further relates to processes useful in the preparation of crystalline forms and salts of N-(3-(4,6-dimethylpyrimidin-5-yl)-4-(2-(pyrrolidin-1-yl)ethoxy)phenyl)cyclopropanecarboxamide and pharmaceutical compositions thereof.

BACKGROUND

Receptors for serotonin (5-hydroxytryptamine, 5-HT) are an important class of G protein coupled receptors. Serotonin receptors are divided into seven subfamilies, referred to as 5-$HT_1$ through 5-$HT_7$, inclusive. These subfamilies are further divided into subtypes. For example, the 5-$HT_2$ subfamily is divided into three receptor subtypes: 5-$HT_{2A}$, 5-$HT_{2B}$, and 5-$HT_{2C}$. Certain modulators of 5-$HT_{2A}$ serotonin receptor activity are useful in the treatment of platelet aggregation, coronary artery disease, myocardial infarction, transient ischemic attack, angina, stroke, atrial fibrillation, blood clot formation, or symptoms thereof.

There is a need for compounds that can be used to treat disorders related to the 5-$HT_{2A}$ serotonin receptor, including disorders of the cardiovascular system. In particular, there is a need for compounds that possess physical and chemical stability and favorable pharmacokinetic properties.

SUMMARY

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Formula (Ia)):

Ia

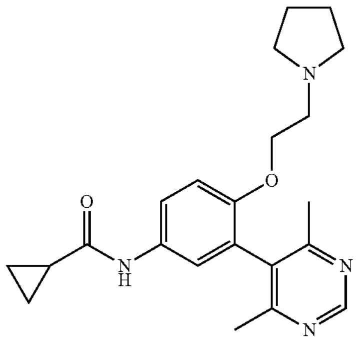

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide comprising the steps of:

a) contacting said N-(3-(4,6-dimethylpyrimidin-5-yl)-4-(2-(pyrrolidin-1-yl)ethoxy)phenyl)cyclopropanecarboxamide (Formula (Ia)) with an acid, in the presence of a contacting-step solvent;

b) crystallizing N-(3-(4,6-dimethylpyrimidin-5-yl)-4-(2-(pyrrolidin-1-yl)ethoxy)phenyl)cyclopropanecarboxamide (Formula (Ia)) to obtain a crystalline salt of N-(3-(4,6-dimethylpyrimidin-5-yl)-4-(2-(pyrrolidin-1-yl)ethoxy)phenyl)cyclopropanecarboxamide (Formula (Ia)) in a crystallizing mixture; and c) isolating said crystalline salt of N-(3-(4,6-dimethylpyrimidin-5-yl)-4-(2-(pyrrolidin-1-yl)ethoxy)phenyl)cyclopropanecarboxamide (Formula (Ia)) from said crystallizing mixture to obtain said crystalline salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide, wherein the process further comprises stirring after the contacting step.

One aspect of the present disclosure relates to processes wherein the the contacting-step solvent is selected from a group consisting of acetone, acetonitrile, 1-butanol, 2-butanol, butyl acetate, 1,2-dimethoxyethane, N,N-dimethylacetamide, 1,4-dioxane, ethanol, 2-ethoxyethanol, ethyl acetate, isopropyl acetate, heptane, methyl isobutyl ketone (MIBK), 2-methyl-1-propanol, N-methyl pyrrolidone, 1-propanol, 2-propanol, n-propyl acetate, tert-butyl methyl ether (TBME), tetrahydrofuran (THF), water, and dimethyl sulfoxide (DMSO) and combinations thereof.

One aspect of the present disclosure relates to processes wherein the acid is a mineral acid or an organic acid.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide comprising the step of:

isolating said crystalline salt of N-(3-(4,6-dimethylpyrimidin-5-yl)-4-(2-(pyrrolidin-1-yl)ethoxy)phenyl)cyclopropanecarboxamide (Formula (Ia)) from said crystallizing mixture to obtain said crystalline salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Formula (Ia)) prepared by a process as described herein.

One aspect of the present disclosure relates to compositions comprising a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein.

One aspect of the present disclosure relates to compositions comprising a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein, and a pharmaceutically acceptable carrier.

One aspect of the present disclosure relates to processes of making a composition comprising mixing a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein, with a phamaceutically acceptable carrier.

One aspect of the present disclosure relates to methods of treating a $5HT_{2A}$-related disorder in an individual, comprising administering to an individual in need thereof, a therapeutically effective amount of a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein or a pharmaceutical composition thereof.

One aspect of the present disclosure relates to the use of a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein, in the manufacture of a medicament for the treatment of a $5HT_{2A}$-related disorder.

One aspect of the present disclosure relates to a crystalline form of $5HT_{2A}$-related disorder as described herein, for use in a method of treatment of the human or animal body by therapy. One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein, for use in a method of treatment of a $5HT_{2A}$-related disorder. One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein, for use in a method of treatment of a $5HT_{2A}$-related disorder. One aspect of the present disclosure relates to crystalline salts of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline besylate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline besylate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline citrate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline fumarate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline hydrochloride salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline mesylate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline phosphate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline succinate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline tosylate salt of N-(3-(4,6-dimethylpyrimidin-5-yl)-4-(2-(pyrrolidin-1-yl)ethoxy)phenyl)cyclopropanecarboxamide (Formula (Ia)).

These and other aspects of the invention disclosed herein will be set forth in greater detail as the patent disclosure proceeds.

DETAILED DESCRIPTION

Definitions

Figure 1:
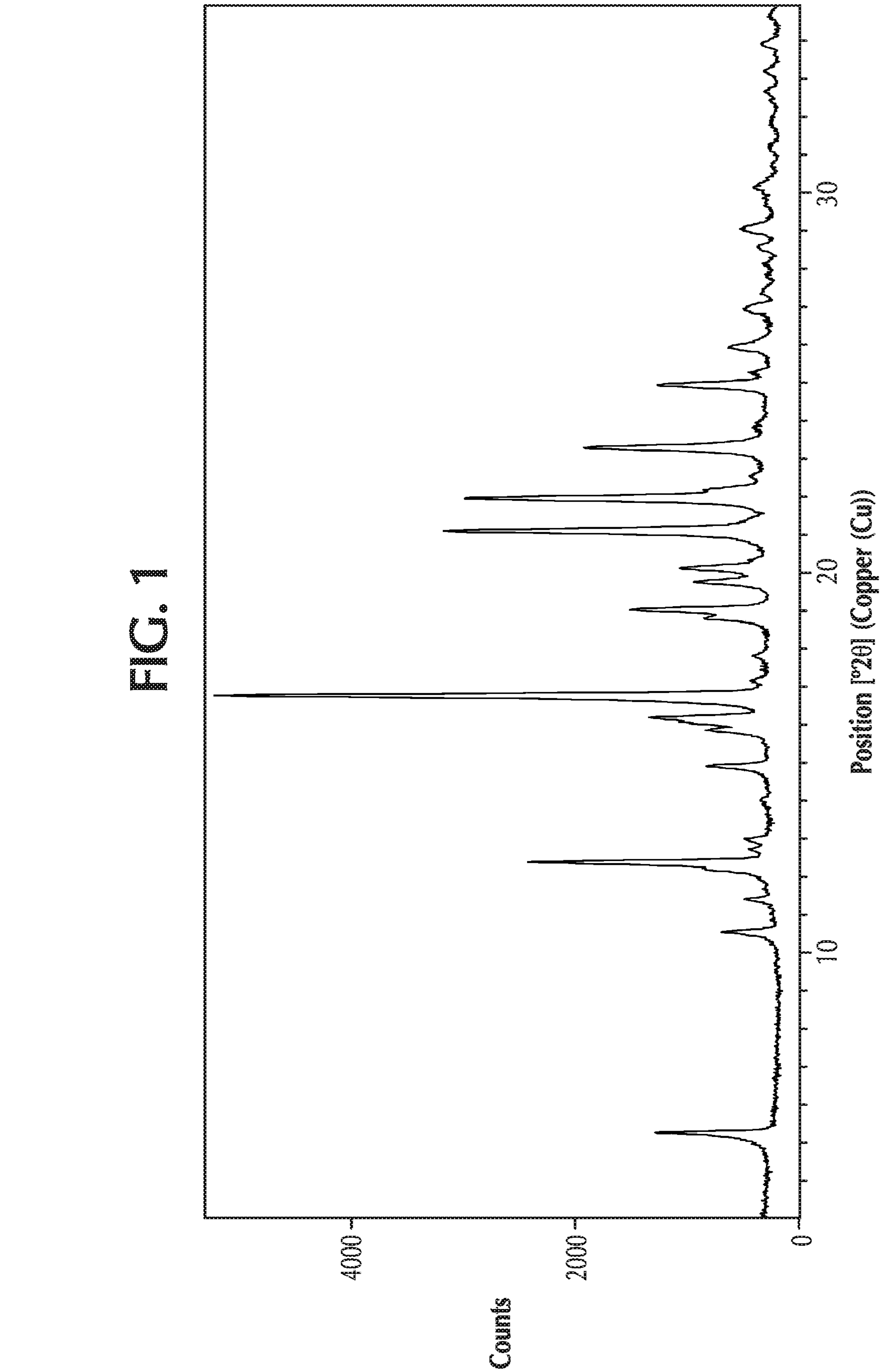
FIG. 1 shows a powder X-ray diffraction (PXRD) pattern for a sample containing a crystalline form of Compound of Formula (Ia).

For clarity and consistency, the following definitions will be used throughout this patent document.

The term "agonists" is intended to mean moieties that interact and activate the receptor, such as the 5-$HT_{2A}$ serotonin receptor, and initiate a physiological or pharmacological response characteristic of that receptor. For example, when moieties activate the intracellular response upon binding to the receptor, or enhance GTP binding to membranes.

The term "antagonists" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

The term "contact or contacting" is intended to mean bringing the indicated moieties together, whether in an in vitro system or an in vivo system. Thus, "contacting" a 5-$HT_{2A}$ serotonin receptor with a compound of the invention includes the administration of a compound of the present invention to an individual, preferably a human, having a 5-$HT_{2A}$ serotonin receptor, as well as, for example, introducing a compound of the invention into a sample containing a cellular or more purified preparation containing a 5-$HT_{2A}$ serotonin receptor.

The term "inverse agonists" is intended to mean moieties that bind to the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

The term "modulate or modulating" is intended to mean an increase or decrease in the amount, quality, response or effect of a particular activity, function or molecule.

As used herein, "administering" means to provide a compound or other therapy, remedy, or treatment such that an individual internalizes a compound.

The term "prescribing" refers to order, authorize, or recommend the use of a drug or other therapy, remedy, or treatment. In some embodiments, a health care provider orally advises, recommends, or authorizes the use of a compound, dosage regimen, or other treatment to an individual. The health care provider may or may not provide a written prescription for the compound, dosage regimen, or treatment. Further, the health care provider may or may not provide the compound or treatment to the individual. For example, the health care provider can advise the individual where to obtain the compound without providing the compound. In some embodiments, a health care provider can provide a written prescription for the compound, dosage regimen, or treatment to the individual. A prescription can be written on paper or recorded on electronic media. In addition, a prescription can be called in (oral) or faxed in (written) to a pharmacy or a dispensary. In some embodiments, a sample of the compound or treatment is given to the individual. As used herein, giving a sample of a compound constitutes an implicit prescription for the compound. Different health care systems around the world use different methods for prescribing and administering compounds or treatments, and these methods are encompassed by the disclosure herein.

A health care provider can include, for example, a physician, nurse, nurse practitioner, or other health care professional who can prescribe or administer compounds (drugs) for the disorders disclosed herein. In addition, a health care provider can include anyone who can recommend, prescribe, administer, or prevent an individual from receiving a compound or drug, including, for example, an insurance provider.

The terms "in need of treatment" and "in need thereof" when referring to treatment, are used interchangeably to mean a judgment made by a caregiver (e.g., physician, nurse, or nurse practitioner in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the disclosure. Accordingly, the compounds of the disclosure can be used in a protective or preventive manner; or compounds of the disclosure can be used to alleviate, inhibit, or ameliorate the disease, condition, or disorder.

The term "individual" refers to any animal, including mammals such as mice, rats, and other rodents, rabbits, dogs, cats, swine, cattle, sheep, horses, primates, and humans. In some embodiments, "individual" refers to humans.

The term "composition" refers to a compound or crystalline form thereof, including but not limited to, salts, solvates, and hydrates of a compound of the present invention, in combination with at least one additional component, such as, a composition obtained/prepared during synthesis, preformulation, in-process testing (i.e., TLC, HPLC, NMR samples), and the like.

The term "hydrate" as used herein means a compound of the invention or a salt thereof that further includes a stoichiometric or non-stoichiometric amount of water bound by non-covalent intermolecular forces.

The term "pharmaceutical composition" refers to a specific composition comprising at least one active ingredient, including but not limited to, salts, solvates, and hydrates of compounds of the present disclosure, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The phrase "pharmaceutically acceptable salts, solvates, and hydrates" when referring to a compound/compounds as described herein embraces pharmaceutically acceptable solvates and/or hydrates of the compound/compounds, pharmaceutically acceptable salts of the compound/compounds, as well as pharmaceutically acceptable solvates and/or hydrates of pharmaceutically acceptable salts of the compound/compounds. It is also understood that when the phrase "pharmaceutically acceptable solvates and hydrates" or the phrase "pharmaceutically acceptable solvate or hydrate" is used when referring to a compound/compounds as described herein that are salts, it embraces pharmaceutically acceptable solvates and/or hydrates of such salts. It is also understood by a person of ordinary skill in the art that hydrates are a subgenus of solvates.

The term "compound," as used herein, is meant to include all stereoisomers, geometric isomers, tautomers, and isotopes of the structures depicted, unless otherwise specified. All compounds, and pharmaceutically acceptable salts thereof, can be found together with other substances such as water and solvents (e.g., in the form of hydrates and solvates) or can be isolated. For example, the term "solvate," as used herein, means a compound or a salt thereof that further includes a stoichiometric or non-stoichiometric amount of a solvent bound by non-covalent intermolecular forces. Exemplary solvents are volatile, non-toxic, and/or acceptable for administration to humans in trace amounts. The term "hydrate" as used herein means a compound or a salt thereof that further includes a stoichiometric or non-stoichiometric amount of water bound by non-covalent intermolecular forces. The term "compound" is also meant to be agnostic as to how the compound is formed, be it synthetically or biologically. For example, a compound of the present disclosure can be produced in the body through metabolism.

The terms "prevent," "preventing," and "prevention" refer to the elimination or reduction of the occurrence or onset of one or more symptoms associated with a particular disorder. For example, the terms "prevent," "preventing," and "prevention" can refer to the administration of therapy on a prophylactic or preventative basis to an individual who may ultimately manifest at least one symptom of a disorder but who has not yet done so. Such individuals can be identified on the basis of risk factors that are known to correlate with the subsequent occurrence of the disease, such as the presence of a biomarker. Alternatively, prevention therapy can be administered as a prophylactic measure without prior identification of a risk factor. Delaying the onset of the at least one episode and/or symptom of a disorder can also be considered prevention or prophylaxis.

The terms "treat," "treating," and "treatment" refer to the administration of therapy to an individual who already manifests, or who has previously manifested, at least one symptom of a disease, disorder, condition, dependence, or behavior. For example, "treating" can include any of the following with respect to a disease, disorder, condition, dependence, or behavior: alleviating, abating, ameliorating, improving, inhibiting (e.g., arresting the development), relieving, or causing regression. "Treating" can also include treating the symptoms, preventing additional symptoms, preventing the underlying physiological causes of the symptoms, or stopping the symptoms (either prophylactically and/or therapeutically) of a disease, disorder, condition, dependence, or behavior. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder.

The term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which can include one or more of the following:

(1) preventing the disorder, for example, preventing a disease, condition, or disorder in an individual who may be predisposed to the disease, condition, or disorder but does not yet experience or display the relevant pathology or symptomatology;

(2) inhibiting the disorder, for example, inhibiting a disease, condition, or disorder in an individual who is experiencing or displaying the relevant pathology or symptomatology (i.e., arresting further development of the pathology and/or symptomatology); and (3) ameliorating the disorder, for example, ameliorating a disease, condition, or disorder in an individual who is experiencing or displaying the relevant pathology or symptomatology (i.e., reversing the pathology and/or symptomatology).

In some embodiments, the term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which includes preventing the disorder, for example, preventing a disease, condition, or disorder in an individual who may be predisposed to the disease, condition, or disorder but does not yet experience or display the relevant pathology or symptomatology.

In some embodiments, the term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which includes inhibiting the disorder, for example, inhibiting a disease, condition, or disorder in an individual who is experiencing or displaying the relevant pathology or symptomatology (i.e., arresting further development of the pathology and/or symptomatology).

In some embodiments, the term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which includes ameliorating the disorder, for example, ameliorating a disease, condition, or disorder in an individual who is experiencing or displaying the relevant pathology or symptomatology (i.e., reversing the pathology and/or symptomatology).

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkylene" means a bivalent branched, or straight chain chemical group containing only carbon and hydrogen, such as methylene, ethylene, n-propylene, isopropylene, n-butylene, iso-butylene, sec-butylene, tert-butylene, n-pentylene, iso-pentylene, sec-pentylene and neopentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "cycloalkyl" means a non-aromatic cyclic ring system containing only carbon atoms in the ring system backbone, such as cyclopropyl, cyclobutyl, cyclopentyl, cyclohexyl, and cyclohexenyl. Cycloalkyl may include multiple fused rings. Cycloalkyl may have any degree of saturation provided that none of the rings in the ring system are aromatic. Cycloalkyl groups can either be unsubstituted or substituted with one or more substituents. In some embodiments, cycloalkyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, and 2,3-dihydro-IH-indenyl. In some embodiments, the aryl is phenyl.

As used herein, "halo," "halide," or "halogen" refers to a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched alkyl substituted with one or more chloro, bromo, fluoro, and/or iodo atom(s). In some embodiments, a haloalkyl is a fluoroalkyl, wherein one or more of the hydrogen atoms have been substituted by fluoro. In some embodiments, haloalkyls are of 1 to 3 carbons in length (e.g., 1 to 2 carbons in length or 1 carbon in length).

As used herein, "haloalkylene" means a bivalent branched, or straight chain alkylene substituted with one or more chloro, bromo, fluoro, and/or iodo atom(s), such as chloromethylene, dichloromethylene, 1,1-dichloroethylene, and 1,2-dichloroehtylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "oxo" means=O, wherein the double bond is to a carbon atom.

As used herein, the term "heteroaryl" means a mono- or bicyclic group having 5 to 10 ring atoms, such as 5, 6, 8, 9, or 10 ring atoms, such as 5, 6, 9, or 10 ring atoms; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrrolo[2,3-6]pyridinyl, quinazolinyl, quinolinyl, thieno[2,3-c]pyridinyl, pyrazolo[3,4-6]pyridinyl, pyrazolo[3,4-c]pyridinyl, pyrazolo[4,3-c]pyridine, pyrazolo[4,3-6]pyridinyl, tetrazolyl, chromane, 2,3-dihydrobenzofuran, tetrahydroquinoline, and isoindoline. In some embodiments, the heteroaryl is selected from thienyl, pyridinyl, furyl, pyrazolyl, imidazolyl, isoindolinyl, pyranyl, pyrazinyl, and pyrimidinyl.

As used herein, "heterocyclyl" or "heterocycloalkyl" means a 3-14 membered, such as 3-11 membered, such as 3-8 membered nonaromatic mono-, bi- or tricyclic group comprising at least one heteroatom in the ring system backbone. Bicyclic and tricyclic heterocyclyl groups may include fused ring systems, spirocyclic ring systems, and bridged ring systems and may include multiple fused rings. In some embodiments, heterocyclyls have one to four heteroatom(s) independently selected from N, O, and S. In some embodiments, heterocyclyls have one to three heteroatom(s) independently selected from N, O, and S. In some embodiments, heterocyclyls have one to two heteroatom(s) independently selected from N, O, and S. In some embodiments, monocyclic heterocyclyls are 3-membered rings. In some embodiments, monocyclic heterocyclyls are 4-membered rings. In some embodiments, monocyclic heterocyclyls are 5-membered rings. In some embodiments, monocyclic heterocyclyls are 6-membered rings. In some embodiments, monocyclic heterocyclyls are 7-membered rings. As used herein, "monocyclic heterocyclyl" means a single nonaromatic cyclic ring comprising at least one heteroatom in the ring system backbone. Examples of heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, and thiomorpholinyl. In some embodiments, the heterocyclyl is selected from azetidinyl, morpholinyl, piperazinyl, pyrrolidinyl, and tetrahydropyridinyl. As used herein, "bicyclic heterocyclyl" means a nonaromatic bicyclic ring system comprising at least one heteroatom in the ring system backbone. Examples of bicyclic heterocyclyls include 2-azabicyclo[1.1.0]butane, 2-azabicyclo[2.1.0]pentane, 2-azabicyclo[I.I.I]pentane, 3-azabicyclo[3.1.0]hexane, 5-azabicyclo[2.1.1]hexane, 3-azabicyclo[3.2.0]heptane, 2-oxa-5-azabicyclo[2.2.1]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, and 2-azabicyclo[2.2.2]octane. As used herein, "spirocyclic heterocyclyl" means a nonaromatic bicyclic ring system comprising at least one heteroatom in the ring system backbone and with the rings connected through just one atom. Examples of spirocyclic heterocyclyls include 2-azaspiro[2.2]pentane, 2-oxa-6-azaspiro[3.3]heptane, 4-azaspiro[2.5]octane, I-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[3.5]nonane, 2,7-diazaspiro[3.5]nonane, 1,7-diazaspiro[4.5]decane, 2,5-diazaspiro[3.6]decane, 1-oxa-8-azaspiro[4.5]decane, 2-oxa-8-azaspiro[4.5]decane.

Examples of heterocycloalkyls include azetidinyl, azetidinyl-3-ol, 3-fluoroazetidinyl, pyrrolidinyl, pyrrolidinyl-3-ol, 3-methoxypyrrolidinyl, 2-(pyrrolidin-3-yl) acetic acid, piperidinyl, piperidinyl-4-ol, 2-(piperidin-4-yl) acetic acid, 4-methoxypiperidinyl, piperazinyl, piperazinyl-1-carbaldehyde, 1-methylpiperazinyl-2-one, 1-(piperazin-1-yl)ethan-1-one, 1-(methylsulfonyl) piperazinyl, 2-hydroxy-1-(piperazin-1-yl)ethan-1-one, 2-oxo-2-(piperazin-1-yl) acetic acid, morpholinyl, 3-azabicyclo[3.1.0]hexanyl, 2-oxa-5-azabicyclo[2.2.1]heptanyl, 3-oxa-6-azabicyclo[3.1.1]heptanyl, octahydropyrrolo[1,2-a]pyrazinyl, hexahydropyrrolo[1,2-a]pyrazinyl-6 (2H)-one, hexahydro-3H-oxazolo[3,4-a]pyrazinyl, hexahydro-3H-oxazolo[3,4-a]pyrazinyl-3-one, 1,4-oxazepanyl-7-one, 2-oxa-6-azaspiro[3.3]heptanyl, 6-oxa-1-azaspiro[3.3]heptanyl, 1,7-diazaspiro[3.5]nonanyl, 1,7-diazaspiro[3.5]nonanyl-2-one, 2,7-diazaspiro[3.5]nonanyl, 2,7-diazaspiro[3.5]nonanyl-1-one, 1-oxa-8-azaspiro[4.5]decanyl, 1-oxa-8-azaspiro[4.5]decanyl-2-one, 2-oxa-8-azaspiro[4.5]decanyl, and 2-oxa-8-azaspiro[4.5]decanyl-1-one.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. In addition, subcombinations of uses and medical indications listed in the embodiments describing such uses and medical indications described herein, are also specifically embraced by the present invention just as if each and every subcombination of uses and medical indications was individually and explicitly recited herein.

Processes

The present disclosure is directed to, inter alia, processes useful in the preparation of a crystalline form of N-(3-(4,6-dimethylpyrimidin-5-yl)-4-(2-(pyrrolidin-1-yl)ethoxy)phenyl)cyclopropanecarboxamide, a modulator of the $5\text{-HT}_{2A}$ serotonin receptor.

The present invention provides, inter alia, processes for preparing compounds of Formula (IIe):

IIe

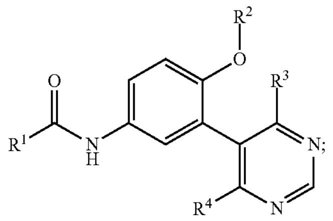

comprising the step of:

coupling the compound of Formula (IId) or a salt thereof:

IId

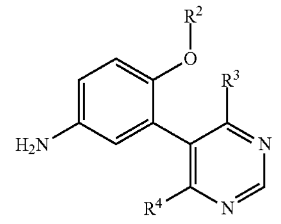

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein $R^{2A}$ and $R^{2B}$, taken together with the nitrogen to which they are attached, form a 3-9 membered heterocycloalkyl ring; and;

$R^3$ and $R^4$ are each independently selected from H, $C_1$-$C_6$ alkyl, and $C_1$-$C_6$ haloalkyl; with an acyl chloride of Formula (IId-1);

IId-1

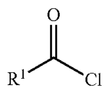

wherein $R^1$ is selected from $R^1$ is selected from $C_1$-$C_6$ alkyl, $C_3$-$C_6$ cycloalkyl, phenyl, 5-10 membered heteroaryl, and 5-9 membered heterocycloalkyl;

in the presence of a base and a solvent to form said compound of Formula (IIe).

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Formula (Ia)):

Ia

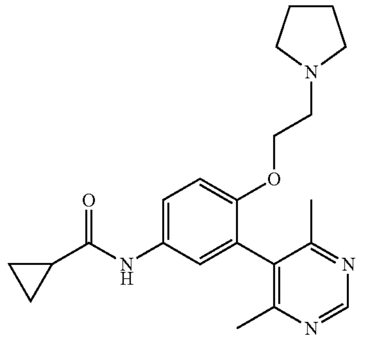

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide comprising the steps of:

a) contacting said N-(3-(4,6-dimethylpyrimidin-5-yl)-4-(2-(pyrrolidin-1-yl)ethoxy)phenyl)cyclopropanecarboxamide (Formula (Ia)) with an acid, in the presence of a contacting-step solvent;

b) crystallizing N-(3-(4,6-dimethylpyrimidin-5-yl)-4-(2-(pyrrolidin-1-yl)ethoxy)phenyl)cyclopropanecarboxamide (Formula (Ia)) to obtain a crystalline salt of N-(3-(4,6-dimethylpyrimidin-5-yl)-4-(2-(pyrrolidin-1-yl)ethoxy)phenyl)cyclopropanecarboxamide (Formula (Ia)) in a crystallizing mixture; and c) isolating said crystalline salt of N-(3-(4,6-dimethylpyrimidin-5-yl)-4-(2-(pyrrolidin-1-yl)ethoxy)phenyl)cyclopropanecarboxamide (Formula (Ia)) from said crystallizing mixture to obtain said crystalline salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the process further comprises stirring after the contacting step.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the stirring is conducted at a temperature of about 20° C. to about 75° C.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the stirring is conducted at a temperature of about 30° C. to about 65° C.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the stirring is conducted at a temperature of about 30° C. to about 55° C.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the stirring is conducted at a temperature of about 30° C. to about 45° C.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the contacting-step solvent is selected from a group consisting of acetone, acetonitrile, 1-butanol, 2-butanol, butyl acetate, 1,2-dimethoxyethane, N,N-dimethylacetamide, 1,4-dioxane, ethanol, 2-ethoxyethanol, ethyl acetate, isopropyl acetate, heptane, methyl isobutyl ketone (MIBK), 2-methyl-1-propanol, N-methyl pyrrolidone, 1-propanol, 2-propanol, n-propyl acetate, tert-butyl methyl ether (TBME), tetrahydrofuran (THF), water, and dimethyl sulfoxide (DMSO) and combinations thereof.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the acid is a mineral acid or an organic acid.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the mineral acid is selected from a group consisting of hydrochloric acid, phosphoric acid, and sulfuric acid. One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein the organic acid is selected from a group consisting of benzenesulfonic acid, benzoic acid, citric acid, fumaric acid, maleic acid, methanesulfonic acid, succinic acid, and p-toluenesulfonic acid.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein isolating comprises filtering said crystalline salt of N-(3-(4,6-dimethylpyrimidin-5-yl)-4-(2-(pyrrolidin-1-yl)ethoxy)phenyl)cyclopropanecarboxamide from said crystallizing mixture.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein isolating comprises removing said crystalline salt of N-(3-(4,6-dimethylpyrimidin-5-yl)-4-(2-(pyrrolidin-1-yl)ethoxy)phenyl)cyclopropanecarboxamide from said crystallizing mixture.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein isolating comprises drying said crystalline salt of N-(3-(4,6-dimethylpyrimidin-5-yl)-4-(2-(pyrrolidin-1-yl)ethoxy)phenyl)cyclopropanecarboxamide from said crystallizing mixture.

In some embodiments, drying is conducted at a temperature of about 25° C. to about 90° C. In some embodiments, drying is conducted at a temperature of about 25° C. to about 85° C. In some embodiments, drying is conducted at a temperature of about 35° C. to about 75° C. In some embodiments, drying is conducted at a temperature of about 35° C. to about 45° C.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein after isolating, said crystalline salt of N-(3-(4,6-dimethylpyrimidin-5-yl)-4-(2-(pyrrolidin-1-yl)ethoxy)phenyl)cyclopropanecarboxamide has a chemical purity of about 95% or greater.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein after isolating, said crystalline salt of N-(3-(4,6-dimethylpyrimidin-5-yl)-4-(2-(pyrrolidin-1-yl)ethoxy)phenyl)cyclopropanecarboxamide has a chemical purity of about 98% or greater.

One aspect of the present disclosure relates to processes for preparing a crystalline salt of N-(3-(4,6-dimethylpyrimidin-5-yl)-4-(2-(pyrrolidin-1-yl)ethoxy)phenyl)cyclopropanecarboxamide (Formula (Ia)), wherein after isolating, said crystalline salt of N-(3-(4,6-dimethylpyrimidin-5-yl)-4-(2-(pyrrolidin-1-yl)ethoxy)phenyl)cyclopropanecarboxamide has a chemical purity of about 99% or greater.

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Formula (Ia)) prepared by a process described herein.

One aspect of the present disclosure relates to processes of making a composition comprising mixing a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein with a pharmaceutically acceptable carrier.

One aspect of the present disclosure relates to processes of making a composition further comprising forming the composition into drug product, such as, a tablet, a pill, a powder, a lozenge, a sachet, a cachet, an elixir, a suspension, an emulsion, a solution, a syrup, a soft gelatin capsule, a hard gelatin capsule, a suppository, a sterile injectable solution, or a sterile packaged powder.

Processes of the Invention

The present invention is directed, inter alia, to processes and intermediates useful in the preparation of N-(3-(4,6-dimethylpyrimidin-5-yl)-4-(2-(pyrrolidin-1-yl)ethoxy)phenyl)cyclopropanecarboxamide of Formula (Ia) and/or salts related thereto.

Representative coupling, alkylation, and reduction steps, and intermediates of Formulae (IIb), (IIc), and (IId) of the present invention are provided below in Schemes I-III.

Scheme I

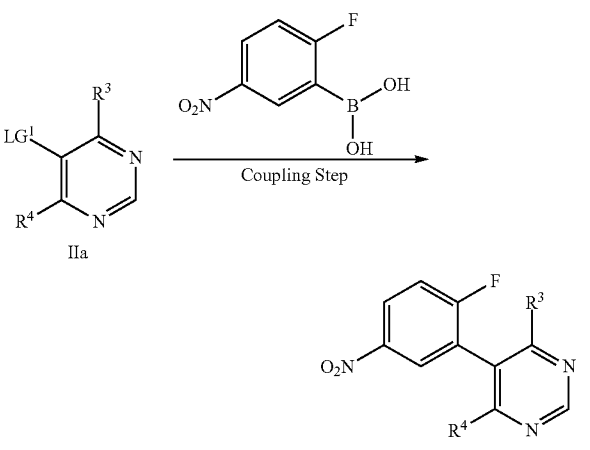

IIa

IIb

Scheme II

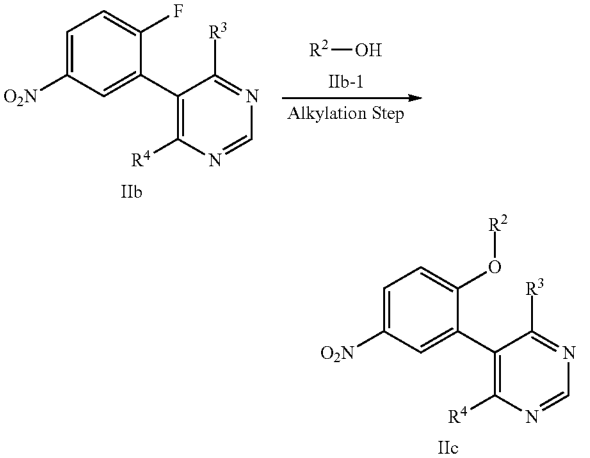

IIb

IIc

Scheme III

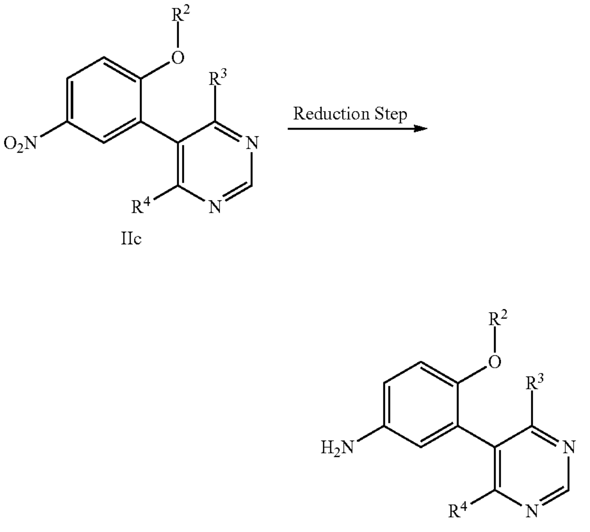

IIc

IId

Representative amide formation step and intermediate of Formulae (IId) of the present invention are provided below in Scheme IV.

Scheme IV

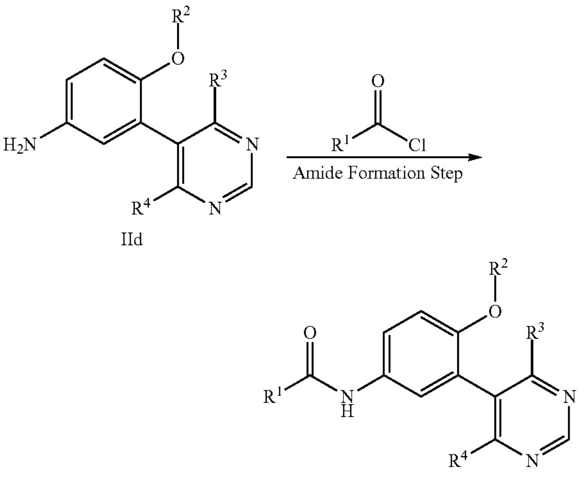

IId

IIe

One aspect of the present invention pertains to processes, such as those exemplified by Schemes I, II, III, and IV (supra), that involve Compounds (IIb), (IIc), (IId), and (IIe).

One aspect of the present invention pertains to intermediates, Compounds (IIb), (IIc), (IId), and (IIe), as exemplified in Schemes I, II, III, and IV (supra), useful in the preparation of Compounds of Formula (IIe), (Ia) and/or a salt related thereto, a salt of compound of Formula (Ia).

One aspect of the present invention pertains to intermediates as exemplified in Schemes I, II, III, and IV (supra), that involve Compounds of formulae (IIb), (IIc), (IId), and (IIe), wherein:

$R^1$ is selected from $R^1$ is selected from $C_1$-$C_6$ alkyl, $C_3$-$C_6$ cycloalkyl, phenyl, 5-10 membered heteroaryl, and 5-9 membered heterocycloalkyl;

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl;

or wherein $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S; and;

$R^3$ and $R^4$ are each independently selected from H, $C_1$-$C_6$ alkyl, and $C_1$-$C_6$ haloalkyl; and $LG^1$ comprises the groups Cl, Br, I, TfO, or TsO.

In some embodiments, $R^1$ is selected from $C_1$-$C_6$ alkyl, $C_3$-$C_6$ cycloalkyl, and 5-10 membered heteroaryl.

In some embodiments, $R^1$ is selected from $C_1$-$C_6$ alkyl, and $C_3$-$C_6$ cycloalkyl.

In some embodiments, $R^1$ is selected $C_3$-$C_6$ cycloalkyl and 5-10 membered heteroaryl. In some embodiments, $R^1$ is $C_3$-$C_6$ cycloalkyl.

In some embodiments, $R^2$ is selected from ($C_1$-$C_3$ alkylene)-(4-10 membered heterocycloalkyl) and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-7 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl).

In some embodiments, $R^2$ is selected from azetidinyl, pyrrolidinyl, and piperidinyl, each of which is optionally substituted with one or more substituents independently selected from halogen, oxo, —OH, ($C_1$-$C_3$ alkyl), and —O—($C_1$-$C_3$ alkyl).

In some embodiments, $R^2$ is selected from azetidinyl, pyrrolidinyl, and piperidinyl, each of which is optionally substituted with one or more $C_1$-$C_3$ alkyl.

In some embodiments, $R^2$ is ($C_1$-$C_3$ alkylene)-(4-10 membered heterocycloalkyl) and the 4-10 membered heterocycloalkyl is selected from azetidinyl, pyrrolidinyl, piperidinyl, piperazinyl, morpholinyl, 3-azabicyclo[3.1.0]hexanyl, 2-oxa-5-azabicyclo[2.2.1]heptanyl, 3-oxa-6-azabicyclo[3.1.1]heptanyl, octahydropyrrolo[1,2-a]pyrazinyl, hexahydro-3H-oxazolo[3,4-a]pyrazinyl, 1,4-oxazepanyl, 2-oxa-6-azaspiro[3.3]heptanyl, 6-oxa-1-azaspiro[3.3]heptanyl, 1,7-diazaspiro[3.5]nonanyl, 2,7-diazaspiro[3.5]nonanyl, 1-oxa-8-azaspiro[4.5]decanyl, and 2-oxa-8-azaspiro[4.5]decanyl, each of which is optionally substituted with one or more substituents independently selected from halogen, oxo, —OH, ($C_1$-$C_3$ alkyl), and —O—($C_1$-$C_3$ alkyl).

In some embodiments, $R^2$ is an optionally substituted ($C_1$-$C_3$ alkyl)-(4-10 membered heterocycloalkyl), where the 4-10 membered heterocycloalkyl is selected from azetidinyl, azetidinyl-3-ol, 3-fluoroazetidinyl, pyrrolidinyl, pyrrolidinyl-3-ol, 3-methoxypyrrolidinyl, 2-(pyrrolidin-3-yl) acetic acid, piperidinyl, piperidinyl-4-ol, 2-(piperidin-4-yl) acetic acid, 4-methoxypiperidinyl, piperazinyl, piperazinyl-1-carbaldehyde, 1-methylpiperazinyl-2-one, 1-(piperazin-1-yl) ethan-1-one, 1-(methylsulfonyl) piperazinyl, 2-hydroxy-1-(piperazin-1-yl)ethan-1-one, 2-oxo-2-(piperazin-1-yl) acetic acid, morpholinyl, 3-azabicyclo[3.1.0]hexanyl, 2-oxa-5-azabicyclo[2.2.1]heptanyl, 3-oxa-6-azabicyclo[3.1.1]heptanyl, octahydropyrrolo[1,2-a]pyrazinyl, hexahydropyrrolo[1,2-a]pyrazinyl-6 (2H)-one, hexahydro-3H-oxazolo[3,4-a] pyrazinyl, hexahydro-3H-oxazolo[3,4-a]pyrazinyl-3-one, 1,4-oxazepanyl-7-one, 2-oxa-6-azaspiro[3.3]heptanyl, 6-oxa-1-azaspiro[3.3]heptanyl, 1,7-diazaspiro[3.5]nonanyl, 1,7-diazaspiro[3.5]nonanyl-2-one, 2,7-diazaspiro[3.5] nonanyl, 2,7-diazaspiro[3.5]nonanyl-1-one, 1-oxa-8-azaspiro[4.5]decanyl, 1-oxa-8-azaspiro[4.5]decanyl-2-one, 2-oxa-8-azaspiro[4.5]decanyl, and 2-oxa-8-azaspiro[4.5]decanyl-1-one.

In some embodiments, $R^2$ is ($C_1$-$C_3$ alkylene)-(4-10 membered heterocycloalkyl) and the 4-10 membered heterocycloalkyl is pyrrolidinyl optionally substituted with one or more substituents independently selected from halogen, oxo, —OH, ($C_1$-$C_3$ alkyl), and —O—($C_1$-$C_3$ alkyl).

In some embodiments, $R^2$ is ($C_1$-$C_3$ alkylene)-$NR^{2A}R^{2B}$, wherein $R^{2A}$ and $R^{2B}$, taken together with the nitrogen to which they are attached, form a 3-7 membered heterocycloalkyl ring.

In some embodiments, $R^{2A}$ and $R^{2B}$, taken together with the nitrogen to which they are attached, form a pyrrolidinyl ring optionally substituted with one or more substituents independently selected from —OH, $C_1$-$C_3$ alkyl, and —O—($C_1$-$C_3$ alkyl).

In some embodiments, $R^2$ is ($C_1$-$C_3$ alkylene)-$NR^{2A}R^{2B}$ In some embodiments, $R^2$ is $CH_2$—$NR^{2A}R^{2B}$.

In some embodiments, $R^2$ is $(CH_2)_2$—$NR^{2A}R^{2B}$ In some embodiments, $R^2$ is $(CH_2)_3$—$NR^{2A}R^{2B}$ In some embodiments, $R^3$ and $R^4$ are each independently selected from H and $C_1$-$C_6$ alkyl.

In some embodiments, $R^3$ and $R^4$ are each $C_1$-$C_6$ alkyl.

In some embodiments, $R^3$ and $R^4$ are each $C_1$-$C_3$ alkyl.

In some embodiments, $R^3$ and $R^4$ are each methyl.

In some embodiments, $LG^1$ is selected from the group consisting Cl, Br, I, and TfO.

In some embodiments, $LG^1$ is selected from the group consisting Cl, Br, and I.

In some embodiments, $LG^1$ is Br or I.

In some embodiments, $LG^1$ is Br.

One aspect of the present invention pertains to a compound of Formula (IIe):

IIe

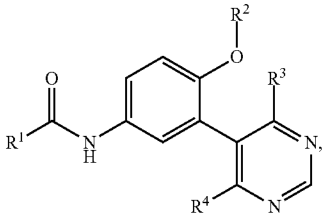

wherein: $R^1$ is $C_3$-$C_6$ cycloalkyl; $R^2$ is ($C_1$-$C_3$ alkylene)-$NR^{2A}R^{2B}$, wherein $R^{2A}$ and $R^{2B}$, taken together with the nitrogen to which they are attached, form a 3-7 membered heterocycloalkyl ring; and $R^3$ and $R^4$ are each $C_1$-$C_6$ alkyl.

In some embodiments, $R^1$ is cyclopropyl.

In some embodiments, $R^2$ is

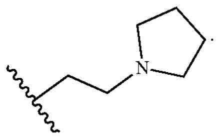 [SMILES: *CCN1CCCC1]

In some embodiments, $R^3$ and $R^4$ are each methyl.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $LG^1$, $R^1$, $R^2$, $R^3$, and $R^4$) contained within the generic chemical formulae described herein are specifically embraced by the present invention just as if each and every combination was individually explicitly recited, to the extent that such combinations embrace stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

I. Coupling Step

One aspect of the present invention pertains to processes for preparing the intermediate compound of Formula (IIb):

IIb

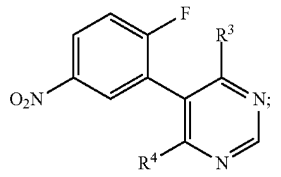

comprising reacting (2-fluoro-5-nitrophenyl) boronic acid with a compound of Formula (IIa):

IIa

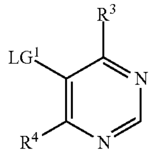

wherein $R^3$ and $R^4$ are each independently selected from H, $C_1$-$C_6$ alkyl, and $C_1$-$C_6$ haloalkyl; and $LG^1$ comprises the groups Cl, Br, I, TfO, or TsO;

in the presence of:

i) a palladium catalyst;

ii) a base; and iii) a solvent;

to form compound of Formula (IIb).

In some embodiments, $R^3$ and $R^4$ are each independently selected from H and $C_1$-$C_6$ alkyl.

In some embodiments, $R^3$ and $R^4$ are each $C_1$-$C_6$ alkyl.

In some embodiments, $R^3$ and $R^4$ are each $C_1$-$C_3$ alkyl.

In some embodiments, $R^3$ and $R^4$ are each methyl.

In some embodiments, $LG^1$ is selected from the group consisting Cl, Br, and I.

In some embodiments, $LG^1$ is Br or I.

In some embodiments, $LG^1$ is Br.

In some embodiments, the palladium-based catalyst comprises (2-Dicyclohexylphosphino-2',6'-dimethoxybiphenyl) [2-(2'-amino-1,1'-biphenyl)]palladium (II) methanesulfonate (SPhos Pd G3), 2-Dicyclohexylphosphino-2',4',6'-triisopropyl-1,1'-biphenyl) [2-(2'-amino-1,1'-biphenyl)] palladium (II) methanesulfonate (XPhos Pd G3), Methanesulfonato (2-dicyclohexylphosphino-2',4', 6'-tri-i-propyl-1,1'-biphenyl) (2'-methylamino-1,1'-biphenyl-2-yl) palladium (II) (XPhos Pd G4), Chloro(2-dicyclohexylphosphino-2',4',6'-triisopropyl-1,1'-biphenyl) [2-(2'-amino-1,1'-biphenyl)] palladium (II) (XPhos Pd G2), Chloro(2-dicyclohexylphosphino-2', 6'-dimethoxy-1,1'-biphenyl) [2-(2'-amino-1,1'-biphenyl)]palladium (II) (SPhos Pd G2), or [(2-Di-tert-butylphosphino-2',4',6'-triisopropyl-1,1'-biphenyl)-2-(2'-amino-1,1'-biphenyl)]palladium (II) methanesulfonate (tBuXPhos Pd G3).

In some embodiments, the base comprises dipotassium hydrogenphosphate ($K_2HPO_4$), potassium bicarbonate ($KHCO_3$), potassium carbonate ($K_2CO_3$), potassium dihydrogen phosphate ($KH_2PO_4$), potassium phosphate ($K_3PO_4$), potassium tert-butoxide (KOtBu), sodium bicarbonate ($NaHCO_3$), or sodium carbonate ($Na_2CO_3$).

In some embodiments, the solvent comprises acetonitrile; 2-methyltetrahydrofuran; tetrahydrofuran (THF); THF-water; THF-water with ethanol; THF-water with 2-propanol; or toluene.

In some embodiments, the solvent is 2-methyltetrahydrofuran; tetrahydrofuran (THF); or THF-water.

In some embodiments, the solvent is THF-water; THF-water with 10% ethanol; or THF-water with 10% 2-propanol.

In some embodiments, said reacting step is conducted at a temperature of about 40° C. to about 100° C.

In some embodiments, said reacting step is conducted at a temperature of about 50° C. to about 100° C.

In some embodiments, said reacting step is conducted at a temperature of about 60° C. to about 100° C.

In one embodiment, a compound of Formula (IIb-1):

(IIb-1)

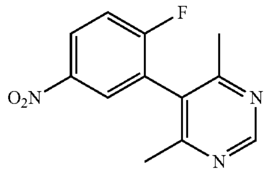

is prepared by process according to the coupling step.

II. Alkylation Step

One aspect of the present invention pertains to processes for preparing the intermediate compound of Formula (IIc) or salt thereof:

IIc

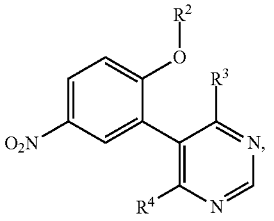

comprising the step of alkylating a compound of Formula (IIb-1):

IIb-1

$R^2$—OH, with the compound of Formula (IIb):

IIb

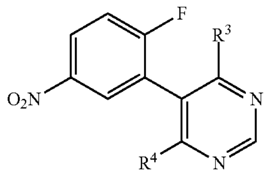

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-7 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl); and;

$R^3$ and $R^4$ are each independently selected from H, $C_1$-$C_6$ alkyl, and $C_1$-$C_6$ haloalkyl; and optionally followed by treatment with a mineral acid in presence of an alcoholic solvent to form the salt of the compound of Formula (IIc).

In some embodiments, $R^2$ is ($C_1$-$C_3$ alkylene)-$NR^{2A}R^{2B}$, wherein $R^{2A}$ and $R^{2B}$, taken together with the nitrogen to which they are attached, form a 3-5 membered heterocycloalkyl ring. In some embodiments, $R^{2A}$ and $R^{2B}$, taken together with the nitrogen to which they are attached, form a pyrrolidinyl ring optionally substituted with one or more substituents independently selected from —OH, $C_1$-$C_3$ alkyl, and —O—($C_1$-$C_3$ alkyl).

In some embodiments, $R^2$ is ($C_1$-$C_3$ alkylene)-$NR^{2A}R^{2B}$.

In some embodiments, $R^2$ is $CH_2$—$NR^{2A}R^{2B}$.

In some embodiments, $R^2$ is $(CH_2)_2$—$NR^{2A}R^{2B}$ In some embodiments, $R^2$ is $(CH_2)_3$—$NR^{2A}R^{2B}$.

In some embodiments, $R^3$ and $R^4$ are each independently selected from H and $C_1$-$C_6$ alkyl.

In some embodiments, $R^3$ and $R^4$ are each $C_1$-$C_3$ alkyl.

In some embodiments, $R^3$ and $R^4$ are each methyl.

In some embodiments, the alkylating step is done in the presence of an alkylating-step base and an alkylating-step solvent.

In some embodiments, the alkylating step comprises a alkylating-step base comprises calcium carbonate ($CaCO_3$), cesium carbonate ($CS_2CO_3$), N,N-diisopropylethylamine (DIPEA), dipotassium hydrogenphosphate ($K_2HPO_4$), potassium bicarbonate ($KHCO_3$), potassium carbonate ($K_2CO_3$), potassium dihydrogen phosphate ($KH_2PO_4$), potassium phosphate ($K_3PO_4$), potassium tert-butoxide (KOtBu), sodium bicarbonate ($NaHCO_3$), sodium carbonate ($Na_2CO_3$), or triethylamine.

In some embodiments, the alkylating-step solvent comprises acetonitrile, N,N-dimethylacetamide, N,N-dimethylformamide (DMF), dimethylsulfoxide (DMSO), hexamethylphosphoric triamide (HMPA), tetrahydrofuran (THF) or mixtures thereof.

In some embodiments, said alkylating step is conducted at a temperature of about 25° C. to about 100° C.

In some embodiments, said alkylating step is conducted at a temperature of about 45° C. to about 100° C.

In some embodiments, said alkylating step is conducted at a temperature of about 55° C. to about 100° C.

In some embodiments, said alkylating step is conducted at a temperature of about 65° C. to about 100° C.

In some embodiments, alkylating atep is followed by treatment with a mineral acid in presence of an alcoholic solvent to form the salt of the compound of Formula (IIc).

In some embodiments, alkylating atep is followed by treatment with HCl in presence of methanol to form the hydrochloride salt of the compound of Formula (IIc).

In some embodiments, alkylating atep is followed by treatment with HCl in presence of 2-propanol to form the hydrochloride salt of the compound of Formula (IIc).

In one embodiment, a compound of Formula (IIc-1) or a hydrochloride salt thereof:

IIc-1

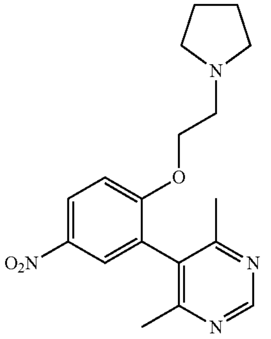

is prepared by process according to the alkylation step.

III. Reduction Step

One aspect of the present invention pertains to processes for preparing the intermediate compound of Formula (IId) or salt thereof:

IId

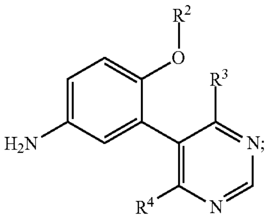

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-7 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl); and; $R^3$ and $R^4$ are each independently selected from H, $C_1$-$C_6$ alkyl, and $C_1$-$C_6$ haloalkyl;

is prepared by process comprising the step of reducing a compound of Formula (IIc) or a salt thereof:

IIc

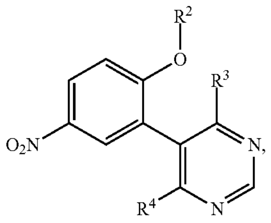

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein $R^{2A}$ and $R^{2B}$, taken together with the nitrogen to which they are attached, form a 3-7 membered heterocycloalkyl ring; and;

$R^3$ and $R^4$ are each independently selected from H, $C_1$-$C_6$ alkyl, and $C_1$-$C_6$ haloalkyl.

In some embodiments, $R^2$ is selected from ($C_1$-$C_3$ alkylene)-(4-10 membered heterocycloalkyl), and ($C_1$-$C_3$ alkylene)-$NR^{2A}R^{2B}$, wherein $R^{2A}$ and $R^{2B}$, taken together with the nitrogen to which they are attached, form a 3-5 membered heterocycloalkyl ring.

In some embodiments, $R^{2A}$ and $R^{2B}$, taken together with the nitrogen to which they are attached, form a pyrrolidinyl ring optionally substituted with one or more substituents independently selected from —OH, $C_1$-$C_3$ alkyl, and —O—($C_1$-$C_3$ alkyl).

In some embodiments, $R^2$ is ($C_1$-$C_3$ alkylene)-$NR^{2A}R^{2B}$ In some embodiments, $R^2$ is $CH_2$—$NR^{2A}R^{2B}$.

In some embodiments, $R^2$ is $(CH_2)_2$—$NR^{2A}R^{2B}$.

In some embodiments, $R^2$ is $(CH_2)_3$—$NR^{2A}R^{2B}$.

In some embodiments, $R^3$ and $R^4$ are each independently selected from H and $C_1$-$C_6$ alkyl.

In some embodiments, $R^3$ and $R^4$ are each $C_1$-$C_3$ alkyl.

In some embodiments, $R^3$ and $R^4$ are each methyl.

In some embodiments, the reducing step is done in the presence of a reducing-step agent and a reducing-step solvent.

In some embodiments, the reducing step comprises a reducing-step agent is selected from the group consisting of:

a) iron (Fe) and ammonium chloride ($NH_4Cl$); or b) hydrogen and palladium/carbon (Pd/C); or c) sodium dithionite.

In some embodiments, the reducing step comprises a reducing-step solvent comprises dimethylsulfoxide (DMSO), ethanol, 2-propanol, water, or mixtures thereof.

In some embodiments, the said reducing is conducted at a temperature of about 15° C. to about 90° C.

In some embodiments, the said compound of Formula (IIc) or salt thereof is:

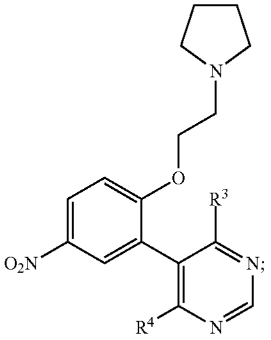

wherein $R^3$ and $R^4$ are each independently selected from H and $C_1$-$C_6$ alkyl;

the reducing-step agent comprises hydrogen and palladium/carbon (Pd/C); and the reducing-step solvent is ethanol and water.

In one embodiment, a compound of Formula (IId-1) or a hydrochloride salt thereof:

IId-1

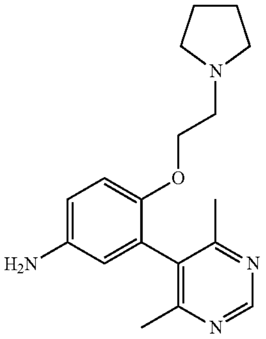

is prepared by process according to the reduction step.

IV. Amide Formation Step

One aspect of the present invention pertains to processes for preparing the intermediate compound of Formula (IIe) or salt thereof:

IIe

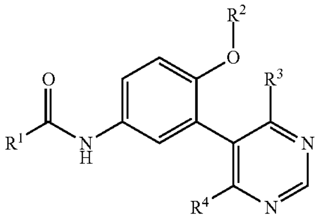

comprising the step of:

coupling the compound of Formula (IId) or a salt thereof:

IId

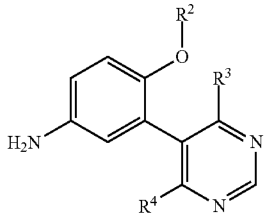

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl); and;

$R^3$ and $R^4$ are each independently selected from H, $C_1$-$C_6$ alkyl, and $C_1$-$C_6$ haloalkyl;

with an acyl chloride of Formula (IId-1)

IId-1

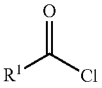

wherein $R^1$ is selected from $R^1$ is selected from $C_1$-$C_6$ alkyl, $C_3$-$C_6$ cycloalkyl, phenyl, 5-10 membered heteroaryl, and 5-9 membered heterocycloalkyl;

in the presence of a base and a solvent to form said compound of Formula (IIe).

In some embodiments, $R^2$ is selected from ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-7 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl); and; $R^3$ and $R^4$ are each independently selected from H and $C_1$-$C_6$ alkyl.

In some embodiments, $R^2$ is ($C_1$-$C_3$ alkylene)-$NR^{2A}R^{2B}$, wherein $R^{2A}$ and $R^{2B}$, taken together with the nitrogen to which they are attached, form a 3-5 membered heterocycloalkyl ring.

In some embodiments, $R^{2A}$ and $R^{2B}$, taken together with the nitrogen to which they are attached, form a pyrrolidinyl ring optionally substituted with one or more substituents independently selected from —OH, $C_1$-$C_3$ alkyl, and —O—($C_1$-$C_3$ alkyl).

In some embodiments, $R^2$ is ($C_1$-$C_3$ alkylene)-$NR^{2A}R^{2B}$.

In some embodiments, $R^2$ is $CH_2$—$NR^{2A}R^{2B}$.

In some embodiments, $R^2$ is $(CH_2)_2$—$NR^{2A}R^{2B}$ In some embodiments, $R^2$ is $(CH_2)_3$—$NR^{2A}R^{2B}$.

In some embodiments, $R^3$ and $R^4$ are each independently selected from H and $C_1$-$C_6$ alkyl.

In some embodiments, $R^3$ and $R^4$ are each $C_1$-$C_3$ alkyl.

In some embodiments, $R^3$ and $R^4$ are each methyl.

In some embodiments, $R^1$ is selected from $R^1$ is selected from $C_1$-$C_6$ alkyl and $C_3$-$C_6$ cycloalkyl.

In some embodiments, the base is selected from the group consisting of N,N-dimethylpyridin-4-amine, 2,6-Dimethylpyridine, N-ethyl-N-isopropylpropan-2-amine, potassium carbonate ($K_2CO_3$), potassium phosphate ($K_3PO_4$), potassium hydrogen phosphate ($K_2HPO_4$), pyridine, and triethylamine.

In some embodiments, the base is selected from the group consisting of potassium carbonate ($K_2CO_3$), potassium phosphate ($K_3PO_4$), potassium hydrogen phosphate ($K_2HPO_4$), and triethylamine.

In some embodiments, the solvent is selected from the group consisting of acetonitrile, dichloromethane (DCM), dimethylformamide (DMF), dimethylacetamide (DMA), dimethylsulfoxide (DMSO), 1,4-dioxane, 2-methyltetrahydrofuran, tetrahydrofuran and dichloromethane-water mixture.

In some embodiments, the said compound of Formula (IId) or salt thereof is:

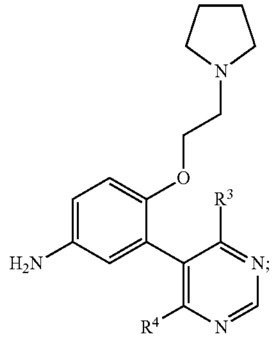

wherein $R^3$ and $R^4$ are each independently selected from H and $C_1$-$C_6$ alkyl;

the base comprises potassium carbonate, potassium phosphate, potassium hydrogen phosphate, or triethylamine; and the solvent comprises dichloromethane, 2-methyltetrahydrofuran, tetrahydrofuran or dichloromethane-water mixture.

In some embodiments, $R^3$ and $R^4$ are each methyl.

In some embodiments, $R^1$ is cyclopropyl.

In some embodiments, the base is potassium carbonate.

In some embodiments, the solvent is dichloromethane and water mixture.

In one embodiment, a compound of Formula (Ia) or a hydrochloride salt thereof:

(Ia)

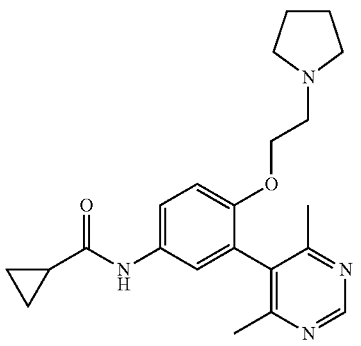

is prepared by process according to the amide formation step.

In one embodiment, the compound of Formula (Ia) is crystalline.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 3rd Ed., Wiley & Sons, 1999.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, 1,2-dichlorobenzene, 1,3-dichlorobenzene, 1,4-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable solvents can include ether solvents, such as: dimethoxymethane, tetrahydrofuran, 2-mthyltetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable solvents can include protic solvents, such as: water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable solvents can include aprotic solvents, such as: benzene, cyclohexane, pentane, hexane, toluene, cycloheptane, methylcyclohexane, heptane, ethylbenzene, o, m-, or p-xylene, octane, indane, nonane, naphthalene, tetrahydrofuran, acetonitrile, dimethyl sulfoxide, propionitrile, ethyl formate, methyl acetate, hexachloroacetone, acetone, ethyl methyl ketone, ethyl acetate, isopropyl acetate, sulfolane, 1,3-dimethyl-3,4,5,6-tetrahydro-2 (1H)-pyrimidinone, 1,3-dimethyl-2-imidazolidinone, N-methylpyrrolidinone, tetramethylurea, nitromethane, and nitrobenzene, and amides, including but not limited to, N,N-dimethylformamide, N,N-dimethylacetamide, formamide, N-methylacetamide, N-methylformamide, N,N-dimethylpropionamide, and hexamethylphosphoramide. It is understood by a person of ordinary skill in the art that that the term amide refers to the following formula:

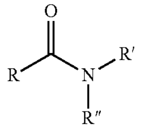

wherein R, R', and R" may be the same or different. In some embodiments, R, R', and R" are each independently selected from H and $C_1$-$C_6$ alkyl. In some embodiments, R, R', and R" are each independently selected from H and $C_1$-$C_4$ alkyl. In some embodiments, R, R', and R" are each independently selected from H and $C_1$-$C_2$ alkyl.

Supercritical carbon dioxide can also be used as a solvent.

The reactions of the processes described herein can be carried out at appropriate temperatures which can be readily determined by one skilled in the art. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to one skilled in the art.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, trifluoroacetic acid, propionic acid, butanoic acid, methanesulfonic acid, p-toluene sulfonic acid, benzenesulfonic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, isopropyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Salts of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of β-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

The compounds described herein and salts thereof can also include all isotopes of atoms occurring in the intermediates or final compounds or salts thereof. Isotopes include those atoms having the same atomic number but different mass numbers. For example, isotopes of hydrogen include tritium and deuterium.

The compounds described herein and salts thereof can also include tautomeric forms, such as keto-enol tautomers. Tautomeric forms can be in equilibrium or sterically locked into one form by appropriate substitution.

Upon carrying out preparation of compounds according to the processes described herein, the usual isolation and purification operations such as concentration, filtration, extraction, solid-phase extraction, recrystallization, chromatography, and the like may be used, to isolate the desired products.

Crystalline Salts of Compound of Formula (Ia)

One aspect of the present disclosure relates to crystalline salts of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline besylate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline besylate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline citrate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline fumarate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline hydrochloride salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline mesylate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline phosphate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline succinate salt of N-(3-(4,6-dimethylpyrimidin-5-yl)-4-(2-(pyrrolidin-1-yl)ethoxy)phenyl)cyclopropanecarboxamide (Formula (Ia)).

One aspect of the present disclosure relates to a crystalline tosylate salt of N-(3-(4,6-dimethylpyrimidin-5-yl)-4-(2-(pyrrolidin-1-yl)ethoxy)phenyl)cyclopropanecarboxamide (Formula (Ia)).

Crystalline salts described herein can be identified by their unique solid state signature with respect to, for example, differential scanning calorimetry (DSC), X-ray powder diffraction (PXRD), and other solid state methods.

Further characterization with respect to water or solvent content of crystalline forms can be gauged by any of the following methods for example, thermogravimetric analysis (TGA), DSC and the like.

For DSC, it is known that the temperatures observed will depend upon sample purity, the rate of temperature change, as well as sample preparation technique and the particular instrument employed. Thus, the values reported herein relating to DSC thermograms can vary by plus or minus about 4°

C. The values reported herein relating to DSC thermograms can also vary by plus or minus about 20 joules per gram.

In some embodiments, the DSC thermogram values reported herein relate to desolvation events. When DSC thermogram values reported herein relate to desolvation events, the values reported herein are estimates. Scan rate and pan closure can influence DSC values for desolvation events, which can vary by plus or minus about 25° C. DSC values for desolvation events reported herein were recorded using a sample in an aluminum pan with an uncrimped lid and a scan rate of 10° C./min.

For PXRD, the relative intensities of the peaks can vary, depending upon the sample preparation technique, the sample mounting procedure and the particular instrument employed. Moreover, instrument variation and other factors can often affect the 20 values. Therefore, the peak assignments of diffraction patterns can vary by plus or minus 0.2° 20 (i.e., +0.2).

For TGA, the features reported herein can vary by plus or minus about 5° C. The TGA features reported herein can also vary by plus or minus about 2% weight change due to, for example, sample variation.

1. Compound Ia (Crystalline Form).

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Compound Ia). The physical properties of the crystalline form of Compound Ia are summarized in Table 1 below.

TABLE 1

| | Compound Ia (Crystalline Form, Example 4) |
|---|---|
| PXRD | FIG. 1: Peaks of about □ 9.9% relative intensity at 5.3 ± 0.2°, 10.6 ± 0.2°, 12.4 ± 0.2°, 14.9 ± 0.2°, 15.9 ± 0.2°, 16.2 ± 0.2°, 16.8 ± 0.2°, 18.8 ± 0.2°, 19.0 ± 0.2°, 19.8 ± 0.2°, 20.1 ± 0.2°, 21.1 ± 0.2°, 22.0 ± 0.2°, 23.3 ± 0.2°, and 24.9 ± 0.2° °2□ |
| TGA | FIG. 3: Decrease in weight of about 3.6% out to about 240° C. |
| DSC | FIG. 2: Endotherm extrapolated onset temperature: about 140.1° C. |

Certain X-ray powder diffraction peaks for the crystalline form of N-(3-(4,6-dimethylpyrimidin-5-yl)-4-(2-(pyrrolidin-1-yl)ethoxy)phenyl)cyclopropanecarboxamide (Compound Ia) are shown in Table 2 below.

TABLE 2

| Pos. [°2θ.] | d-spacing [Å] | Rel. Int. [%] | Pos. [°2θ.] | d-spacing [Å] | Rel. Int. [%] |
|---|---|---|---|---|---|
| 5.3 | 16.8 | 21.1 | 22.5 | 3.9 | 4.3 |
| 10.6 | 8.4 | 9.9 | 23. | 3.8 | 35.1 |
| 11.4 | 7.8 | 6.2 | 23.9 | 3.7 | 3.8 |
| 12.4 | 7.1 | 42.4 | 24.9 | 3.6 | 21.9 |
| 12.7 | 7.0 | 5.3 | 25.3 | 3.5 | 4.6 |
| 13.0 | 6.8 | 6.0 | 25.9 | 3.4 | 8.9 |
| 14.0 | 6.3 | 2.9 | 26.9 | 3.3 | 5. |
| 14.9 | 5.9 | 12.3 | 27.4 | 3.2 | 3.0 |
| 15.9 | 5.6 | 13.3 | 27.8 | 3.2 | 1.9 |
| 16.2 | 5.5 | 23.4 | 28.1 | 3.2 | 2.4 |
| 16.8 | 5.3 | 100 | 28.6 | 3.1 | 3.6 |
| 17.2 | 5.2 | 4.6 | 29.0 | 3.1 | 5.7 |
| 17.8 | 5.0 | 4.5 | 30.2 | 3.0 | 4.1 |
| 18.8 | 4.7 | 13.3 | 31.2 | 2.9 | 1.7 |
| 19.0 | 4.7 | 26.5 | 31.8 | 2.8 | 1.2 |
| 19.8 | 4.5 | 15.3 | 32.7 | 2.7 | 2.3 |
| 20.1 | 4.4 | 17.8 | 33.2 | 2.7 | 2.7 |
| 21.1 | 4.2 | 60.5 | 33.9 | 2.6 | 3.1 |

TABLE 2-continued

| Pos. [°2θ.] | d-spacing [Å] | Rel. Int. [%] | Pos. [°2θ.] | d-spacing [Å] | Rel. Int. [%] |
|---|---|---|---|---|---|
| 22.0 | 4.0 | 56.9 | 34.7 | 2.6 | 1.4 |
| 22.2 | 4.0 | 12.1 | | | |

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide.

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide, wherein the crystalline form has an X-ray owder diffraction pattern comprising a peak, in terms of 2θ, at 5.3°±0.2°, and 10.6°±0.2°. In some embodiments, the crystalline form has an X-ray owder diffraction pattern comprising a peak, in terms of 2θ, at 5.3°±0.2°, 10.6°±0.2°, and 12.4°±0.2°. In some embodiments, the crystalline form has an X-ray powder diffraction pattern comprising peaks, in terms of 2θ, at 5.3°±0.2°, 10.6°±0.2°, 12.4°±0.2°, 14.9°±0.2°, and 15.9°±0.2°. In some embodiments, the crystalline form has an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°. In some embodiments, the crystalline form has an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°, 19.8°±0.2°, 20.1°±0.2°, and 21.1°±0.2°. In some embodiments, the crystalline form has an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°, 19.8°±0.2°, 20.1°±0.2°, and 21.1°±0.2°, 22.0°±0.2°, 23.3°±0.2°, and 24.9°±0.2°.

In some embodiments, the crystalline form has an X-ray powder diffraction pattern substantially as shown in FIG. 1, wherein by "substantially" is meant that the reported peaks can vary by about +0.2° 20.

Figure 2:
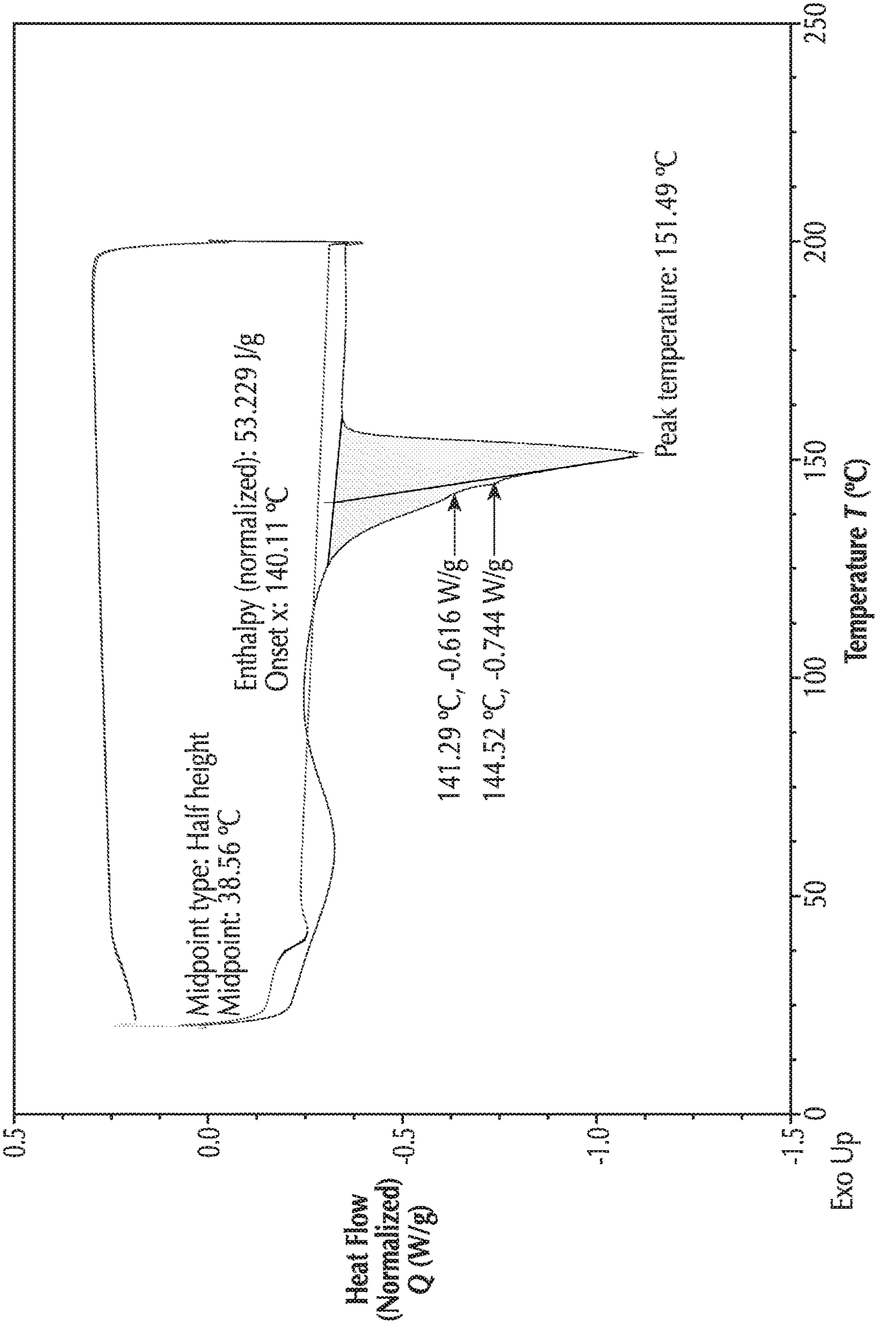
FIG. 2 shows a differential scanning calorimetry (DSC) thermogram for a sample containing a crystalline form of Compound of Formula (Ia).

In some embodiments, the crystalline form has a differential scanning calorimetry thermogram comprising an endotherm with an extrapolated onset temperature between about 138.1° C. and about 153.5° C. In some embodiments, the crystalline form has a differential scanning calorimetry thermogram comprising an endotherm with an extrapolated onset temperature between about 138.1° C. and about 152.5° C. In some embodiments, the crystalline form has a differential scanning calorimetry thermogram comprising an endotherm with an extrapolated onset temperature between about 139.1° C. and about 152.5° C. In some embodiments, the crystalline form has a differential scanning calorimetry thermogram comprising an endotherm with an extrapolated onset temperature at about 140.1° C. In some embodiments, the crystalline form has a differential scanning calorimetry thermogram substantially as shown in FIG. 2, wherein by "substantially" is meant that the reported DSC features can vary by about +4° C. and that the reported DSC features can vary by about +20 joules per gram.

Figure 3:
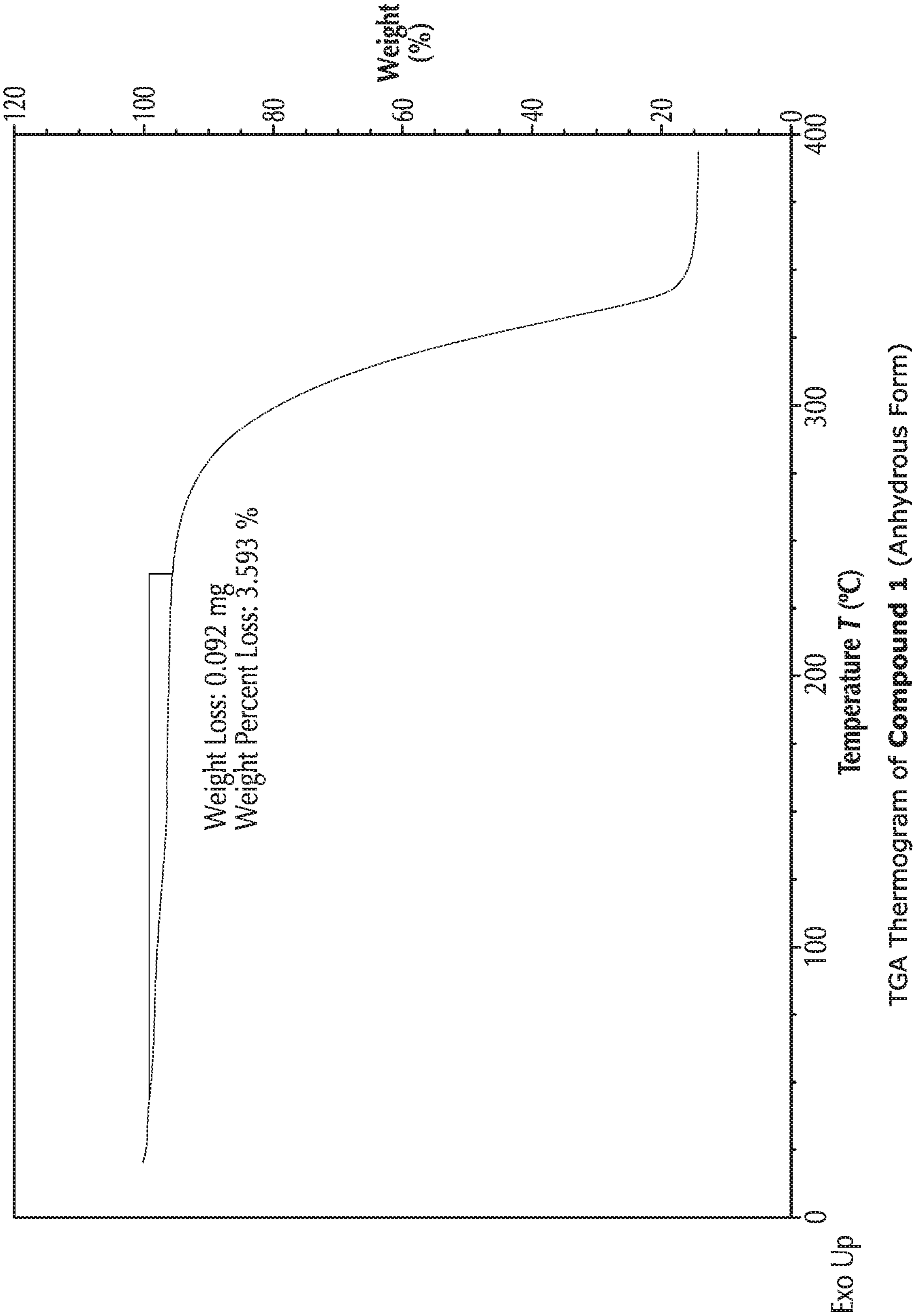
FIG. 3 shows a thermogravimetric analysis (TGA) thermogram of a sample containing a crystalline form of Compound of Formula (Ia).

In some embodiments, the crystalline form has a thermogravimetric analysis profile showing about 4.0% weight loss below about 240° C. In some embodiments, the heptane solvate has a thermogravimetric analysis profile showing about 3.8% weight loss below about 240° C. In some embodiments, the heptane solvate has a thermogravimetric analysis profile showing about 3.6% weight loss below about 240° C. In some embodiments, the crystalline form has a thermogravimetric analysis profile substantially as shown in FIG. 3, wherein by "substantially" is meant that the reported TGA features can vary by about +5° C., and that that the reported TGA features can vary by about +2% weight change.

One aspect of the present disclosure relates to the crystalline form having:

a) an X-ray powder diffraction pattern comprising peaks, in terms of 2θ, at 0.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°;

b) a differential scanning calorimetry thermogram comprising an endotherm with an extrapolated onset temperature between about 138.1° C. and about 153.5° C.; and/or c) a thermogravimetric analysis profile showing about 4.0% weight loss below about 240° C.

One aspect of the present disclosure relates to the crystalline form having:

a) an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°, 19.8°±0.2°, 20.1°±0.2°, and 21.1°±0.2°;

b) a differential scanning calorimetry thermogram comprising an endotherm with an extrapolated onset temperature between about 138.1° C. and about 152.5° C.; and/or c) a thermogravimetric analysis profile showing about 3.8% weight loss below about 240° C.

One aspect of the present disclosure relates to the crystalline form having:

a) an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°, 19.8°±0.2°, 20.1°±0.2°, and 21.1°±0.2°, 22.0°±0.2°, 23.3°±0.2°, and 24.9°±0.2°;

b) a differential scanning calorimetry thermogram comprising an endotherm with an extrapolated onset temperature between about 139.1° C. and about 152.5° C.; and/or c) a thermogravimetric analysis profile showing about 3.6% weight loss below about 240° C.

One aspect of the present disclosure relates to the crystalline form having:

a) an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°, 19.8°±0.2°, 20.1°±0.2°, and 21.1°±0.2°, 22.0°±0.2°, 23.3°±0.2°, and 24.9°±0.2°;

b) a differential scanning calorimetry thermogram comprising an endotherm with an extrapolated onset temperature at about 140.1° C.; and/or c) a thermogravimetric analysis profile showing about 3.6% weight loss below about 240° C.

One aspect of the present disclosure relates to the crystalline form having:

a) an X-ray powder diffraction pattern substantially as shown in FIG. 1;

b) a differential scanning calorimetry thermogram substantially as shown in FIG. 2; and/or c) a thermogravimetric analysis profile substantially as shown in FIG. 3.

Compound Ia (Crystalline Salts).

One aspect of the present disclosure relates to crystalline salts of N-(3-(4,6-dimethylpyrimidin-5-yl)-4-(2-(pyrrolidin-1-yl)ethoxy)phenyl)cyclopropanecarboxamide (Formula (Ia)).

The crystalline salts of Compound Ia are characterized by PXRD. The physical properties for the crystalline salts as determined by PXRD are summarized below.

2. Compound Ia (Besylate Salt)

One aspect of the present disclosure relates to besylate salt of N-(3-(4,6-dimethylpyrimidin-5-yl)-4-(2-(pyrrolidin-1-yl)ethoxy)phenyl)cyclopropanecarboxamide (Compound Ia). The besylate salt is characterized by PXRD. The physical properties for the besylate salt as determined by PXRD are summarized in Table 3 below.

TABLE 3

Figure 4:
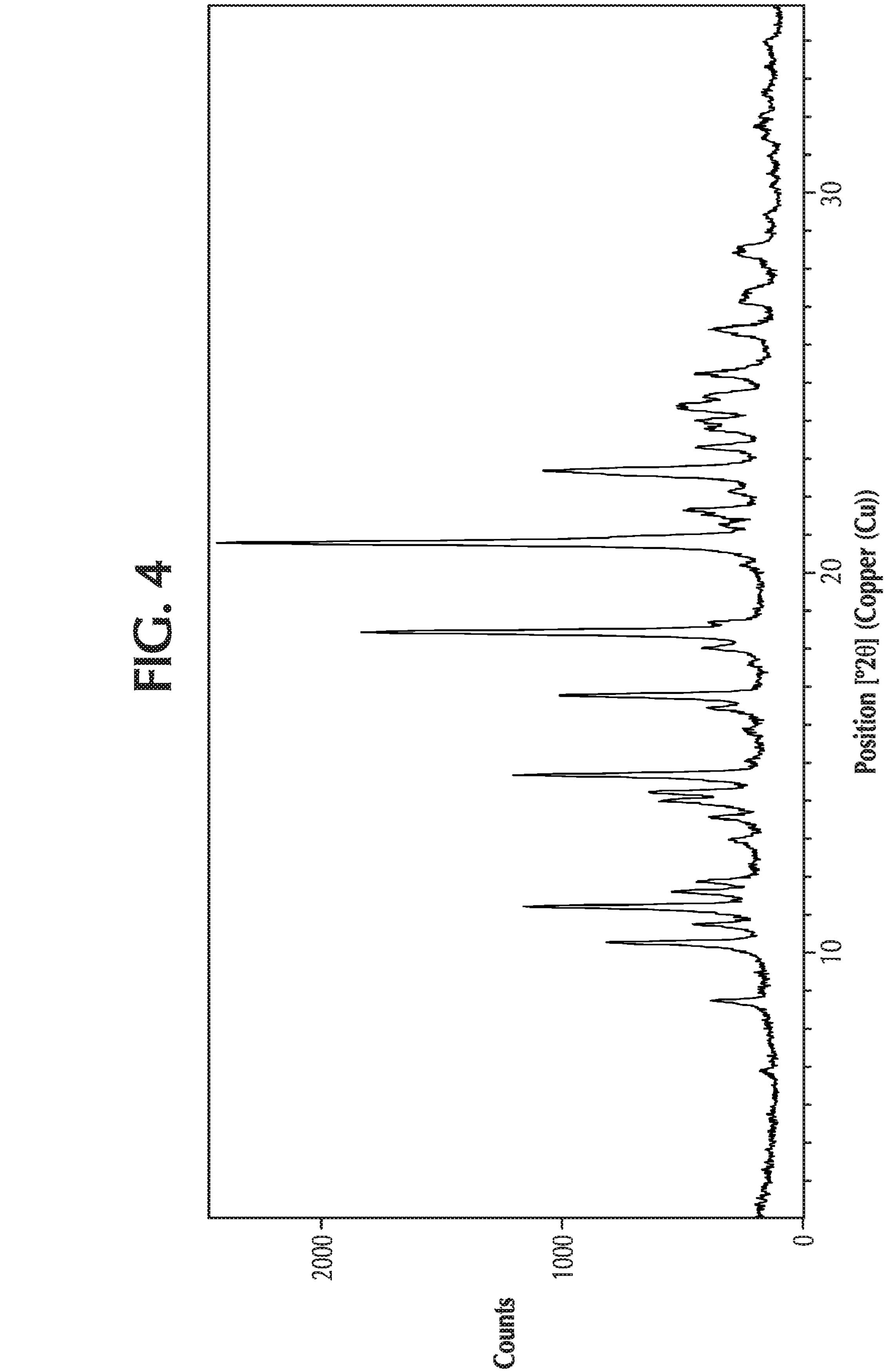
FIG. 4 shows a powder X-ray diffraction (PXRD) pattern for a sample containing a crystalline salt of Compound Ia (Besylate Salt).

| | Compound Ia (Besylate Salt, Example 5) |
|---|---|
| PXRD | FIG. 4: Peaks of about ≥10.7% relative intensity at 8.8° ± 0.2°, 10.3° ± 0.2°, 10.8° ± 0.2°, 11.3° ± 0.2°, 11.6° ± 0.2°, 11.9° ± 0.2°, 14.0° ± 0.2°, 14.3° ± 0.2°, 14.7° ± 0.2°, 16.8° ± 0.2°, 18.0° ± 0.2°, 18.5° ± 0.2°, 20.8° ± 0.2°, 21.7° ± 0.2°, 23.3° ± 0.2°, 24.0° ± 0.2°, 24.3° ± 0.2°, 25.2° ± 0.2°, and 26.4° ± 0.2° °2θ |

The physical properties for a besylate salt (Example 5) prepared using procedure from Example 5 are summarized in Table 4 below.

TABLE 4

Figure 5:
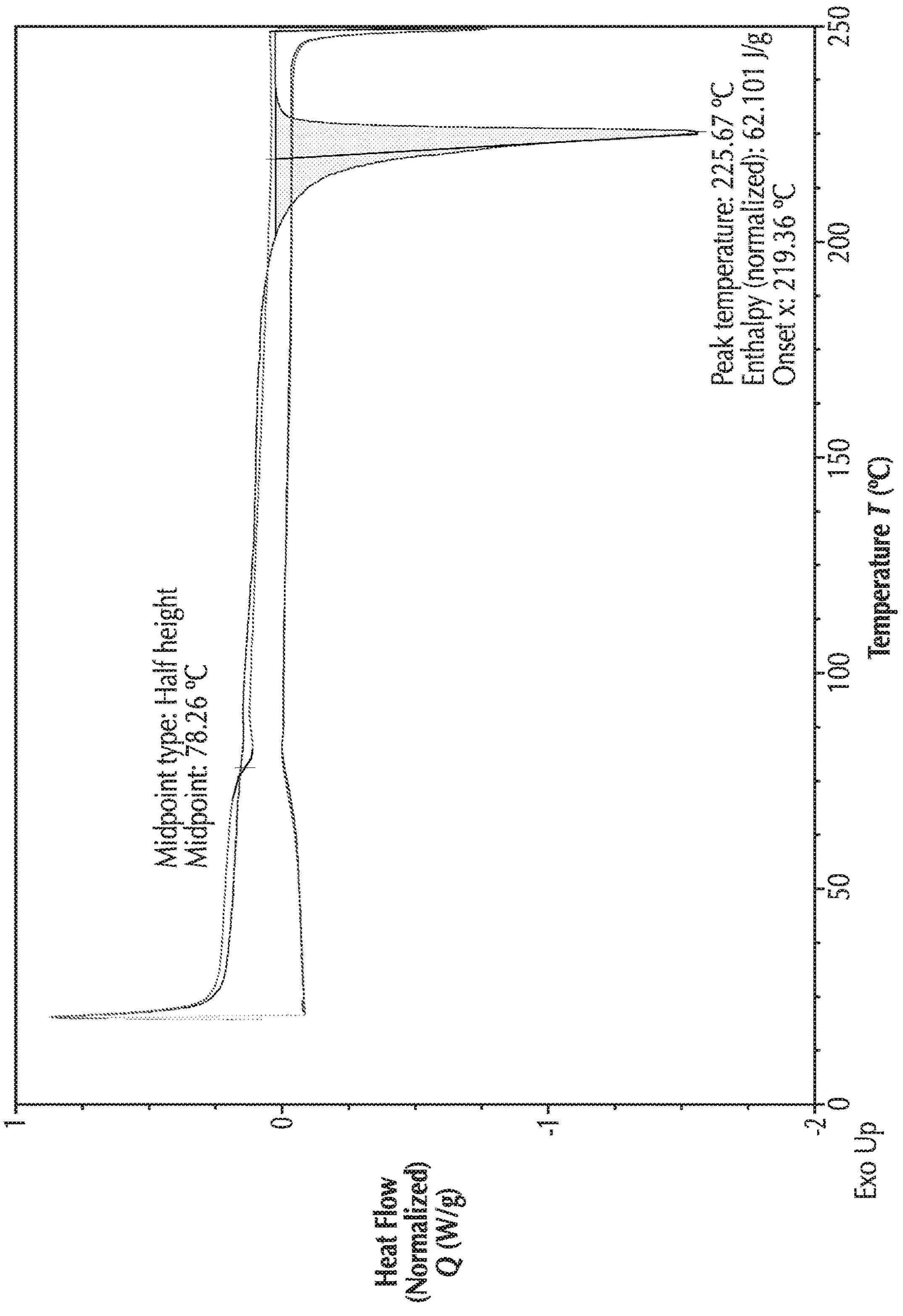
FIG. 5 shows a differential scanning calorimetry (DSC) thermogram for a sample containing a crystalline salt of Compound Ia (Besylate Salt).
Figure 6:
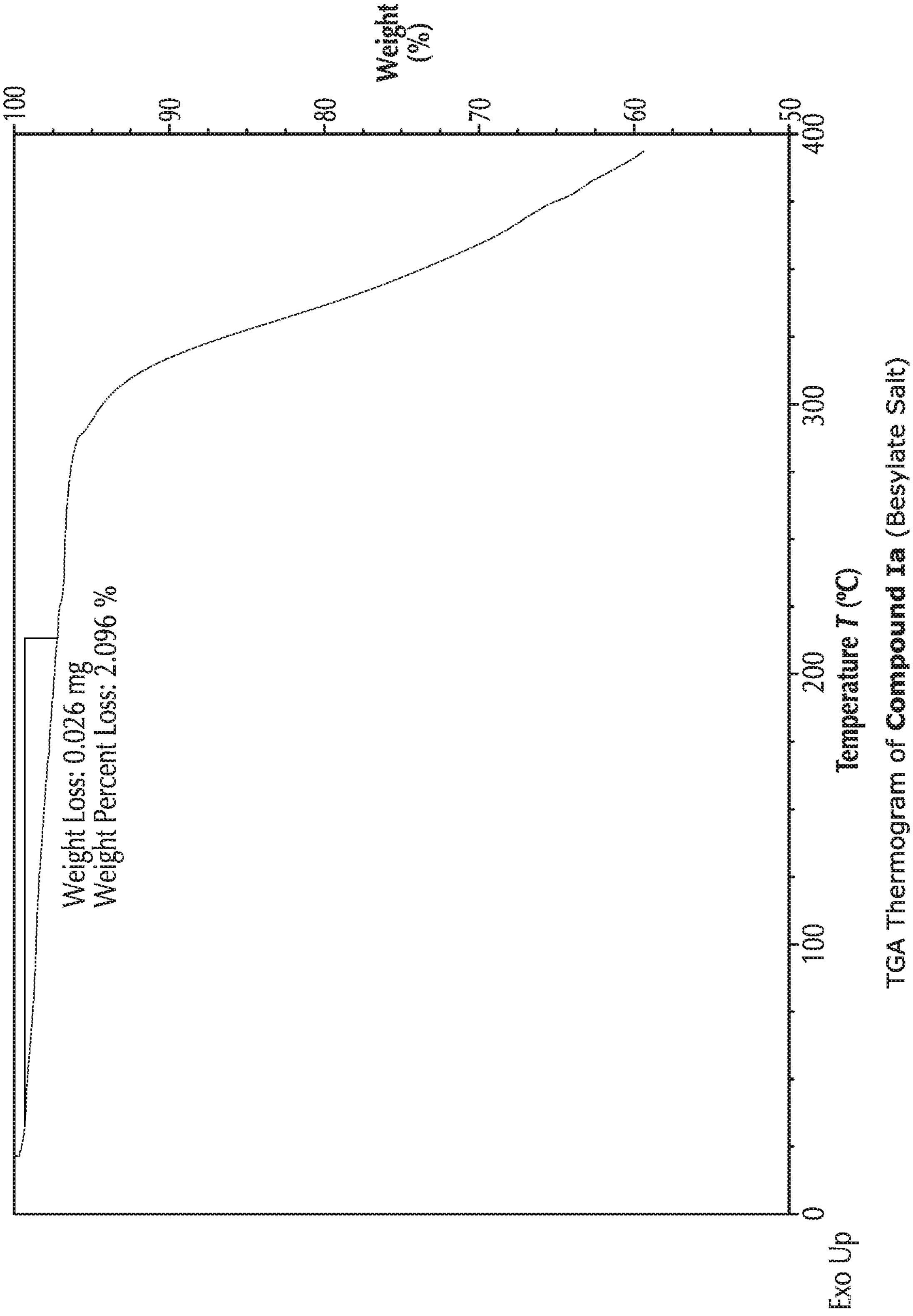
FIG. 6 shows a thermogravimetric analysis (TGA) thermogram of a sample containing a crystalline salt of Compound Ia (Besylate Salt).

| | Compound Ia (Besylate Salt, Example 5) |
|---|---|
| TGA | FIG. 6: Decrease in weight of about 2.1% out to about 220° C. |
| DSC | FIG. 5: Endotherms extrapolated onset temperature at about 145° C. and at about 172° C. |

Certain X-ray powder diffraction peaks for the besylate salt of N-(3-(4,6-dimethylpyrimidin-5-yl)-4-(2-(pyrrolidin-1-yl)ethoxy)phenyl)cyclopropanecarboxamide (Compound Ia) are shown in Table 5 below.

TABLE 5

| Pos. [°2θ.] | d-spacing [Å] | Rel. Int. [%] | Pos. [°2θ.] | d-spacing [Å] | Rel. Int. [%] |
|---|---|---|---|---|---|
| 6.9 | 12.8 | 1.9 | 21.7 | 4.1 | 15.2 |
| 8.8 | 10.1 | 10.9 | 22.2 | 4.0 | 8.2 |
| 10.3 | 8.6 | 28.0 | 22.7 | 3.9 | 40.0 |
| 10.8 | 8.2 | 13.3 | 23.3 | 3.8 | 13.5 |
| 11.3 | 7.9 | 42.4 | 23.8 | 3.7 | 11.6 |
| 11.6 | 7.6 | 17.9 | 24.0 | 3.7 | 13.2 |
| 11.9 | 7.4 | 13.1 | 24.3 | 3.7 | 15.6 |
| 13.0 | 6.8 | 7.7 | 24.7 | 3.6 | 12.3 |
| 13.6 | 6.5 | 10.2 | 25.2 | 3.5 | 13.6 |
| 14.0 | 6.3 | 20.1 | 26.4 | 3.4 | 10.7 |
| 14.3 | 6.2 | 20.3 | 27.1 | 3.3 | 6.5 |
| 14.7 | 6.0 | 45.1 | 27.4 | 3.3 | 5.4 |
| 15.9 | 5.6 | 4.8 | 28.4 | 3.1 | 7.1 |
| 16.5 | 5.4 | 11.4 | 29.4 | 3.0 | 2.1 |
| 16.8 | 5.3 | 37.3 | 31.0 | 2.9 | 1.4 |
| 17.6 | 5.0 | 3.7 | 31.4 | 2.8 | 2.5 |
| 18.0 | 4.9 | 12.5 | 31.7 | 2.8 | 3.7 |
| 18.5 | 4.8 | 70.1 | 32.0 | 2.8 | 3.1 |
| 18.7 | 4.7 | 11.1 | 32.6 | 2.7 | 2.5 |
| 20.2 | 4.4 | 4.5 | 33.3 | 2.7 | 1.8 |
| 20.8 | 4.3 | 95.5 | 34.0 | 2.6 | 2.3 |
| 21.3 | 4.2 | 8.9 | | | |

One aspect of the present disclosure relates to besylate salt of N-(3-(4,6-dimethylpyrimidin-5-yl)-4-(2-(pyrrolidin- 1-yl)ethoxy)phenyl)cyclopropanecarboxamide (Compound Ia). The besylate salt of Compound Ia was prepared by procedure from Example 5.

One aspect of the present disclosure relates to a besylate salt of N-(3-(4,6-dimethylpyrimidin-5-yl)-4-(2-(pyrrolidin-1-yl)ethoxy)phenyl)cyclopropanecarboxamide, having a powder X-ray diffraction pattern comprising a peak, in terms of 2θ, at 8.8°±0.2°, 10.3°±0.2°, 10.8°±0.2°, 11.3°±0.2°, and 11.6°±0.2°. In some embodiments, the besylate salt has an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7°±0.2°, 16.8°±0.2°, and 18.0°±0.2°.

In some embodiments, the besylate salt has an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7°±0.2°, 16.8°±0.2°, 18.0°±0.2°, 18.5°±0.2°, 20.8°±0.2°, and 21.7°±0.2°. In some embodiments, the besylate salt has an X-ray powder diffraction pattern comprising peaks, in terms of 2θ, at 8.8°±0.2°, 10.3°±0.2°, 10.8°±0.2°, 11.3° ±0.2°, 11.6°±0.2°, 11.9°±0.2°, 14.0°±0.2°, 14.3°±0.2°, 14.7°±0.2°, 16.8°±0.2°, 18.0°±0.2°, 18.5°±0.2°, 20.8°±0.2°, 21.7°±0.2°, 23.3°±0.2°, and 24.0°±0.2°. In some embodiments, the besylate salt has an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7°±0.2°, 16.8°±0.2°, 18.0°±0.2°, 18.5°±0.2°, 20.8°±0.2°, 21.7°±0.2°, 23.3°±0.2°, 24.0°±0.2°, 24.3°±0.2°, 25.2°±0.2°, and 26.4°±0.2°. In some embodiments, the besylate salt has an X-ray powder diffraction pattern substantially as shown in FIG. 4, wherein by "substantially" is meant that the reported peaks can vary by about ±0.2° 2θ.

In some embodiments, the besylate salt has a differential scanning calorimetry thermogram comprising an endotherm with an extrapolated onset temperature between about 217.4° C. and about 228.7° C. In some embodiments, the besylate salt has a differential scanning calorimetry thermogram comprising an endotherm with an extrapolated onset temperature between about 217.4° C. and about 227.7° C. In some embodiments, the besylate salt has a differential scanning calorimetry thermogram comprising an endotherm with an extrapolated onset temperature between about 218.4° C. and about 227.7° C. In some embodiments, the besylate salt has a differential scanning calorimetry thermogram comprising an endotherm with an extrapolated onset temperature between about 218.4° C. and about 226.7° C. In some embodiments, the besylate salt has a differential scanning calorimetry thermogram comprising endotherms with an extrapolated onset temperature at about 219.4° C. In some embodiments, the besylate salt has a differential scanning calorimetry thermogram substantially as shown in FIG. 5, wherein by "substantially" is meant that the reported DSC features can vary by about +4° C. and that the reported DSC features can vary by about ±20 joules per gram.

In some embodiments, the besylate salt has a thermogravimetric analysis profile showing about 2.6% weight loss below about 220° C. In some embodiments, the besylate salt has a thermogravimetric analysis profile showing about 2.4% weight loss below about 220° C. In some embodiments, the besylate salt has a thermogravimetric analysis profile showing about 2.2% weight loss below about 220° C. In some embodiments, the besylate salt has a thermogravimetric analysis profile showing about 2.1% weight loss below about 220° C. In some embodiments, the besylate salt has a thermogravimetric analysis profile substantially as shown in FIG. 6, wherein by "substantially" is meant that the reported TGA features can vary by about ±5° C., and that that the reported TGA features can vary by about ±2% weight change.

One aspect of the present disclosure relates to the besylate salt having:

a) an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7°±0.2°, 16.8°±0.2°, and 18.0°±0.2°;

b) a differential scanning calorimetry thermogram comprising an endotherm with an extrapolated onset temperature between about 217.4° C. and about 227.7° C.

c) a thermogravimetric analysis profile showing about 2.6% weight loss below about 220° C.

One aspect of the present disclosure relates to the besylate salt having:

a) an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7° ±0.2°, 16.8°±0.2°, 18.0°±0.2°, 18.5°±0.2°, 20.8°±0.2°, and 21.7°±0.2°;

b) a differential scanning calorimetry thermogram comprising an endotherm with an extrapolated onset temperature between about 218.4° C. and about 227.7° C.; and/or c) a thermogravimetric analysis profile showing about 2.4% weight loss below about 220° C.

One aspect of the present disclosure relates to the besylate salt having:

a) an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7° ±0.2°, 16.8°±0.2°, 18.0°±0.2°, 18.5°±0.2°, 20.8°±0.2°, 21.7°±0.2°, 23.3°±0.2°, 24.0°±0.2°, and 25.2°±0.2°;

b) a differential scanning calorimetry thermogram comprising an endotherm with an extrapolated onset temperature between about 218.4° C. and about 226.7° C.; and/or c) a thermogravimetric analysis profile showing about 2.2% weight loss below about 220° C.

One aspect of the present disclosure relates to the besylate salt having:

a) an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7° ±0.2°, 16.8°±0.2°, 18.0°±0.2°, 18.5°±0.2°, 20.8°±0.2°, 21.7°±0.2°, 23.3°±0.2°, 24.0°±0.2°, 24.3°±0.2°, 25.2°±0.2°, and 26.4°±0.2°;

b) a differential scanning calorimetry thermogram comprising an endotherm with an extrapolated onset temperature between about 218.4° C. and about 226.7° C.; and/or c) a thermogravimetric analysis profile showing about 2.1% weight loss below about 220° C.

One aspect of the present disclosure relates to the besylate salt having:

a) an X-ray powder diffraction pattern comprising peaks, in terms of 2θ, at 8.8°±0.2°, 10.3°±0.2°, 10.8°±0.2°, 11.3°±0.2°, 11.6°±0.2°, 11.9°±0.2°, 14.0°±0.2°, 14.3°±0.2°, 14.7° ±0.2°, 16.8°±0.2°, 18.0°±0.2°, 18.5°±0.2°, 20.8°±0.2°, 21.7°±0.2°, 23.3°±0.2°, 24.0°±0.2°, 24.3°±0.2°, 25.2°±0.2°, and 26.4°±0.2°;

b) a differential scanning calorimetry thermogram comprising an endotherm with an extrapolated onset temperature at about 219.4° C.; and/or c) a thermogravimetric analysis profile showing about 2.1% weight loss below about 220° C.

One aspect of the present disclosure relates to the besylate salt having:

a) an X-ray powder diffraction pattern substantially as shown in FIG. 4;

b) a differential scanning calorimetry thermogram substantially as shown in FIG. 5; and/or c) a thermogravimetric analysis profile substantially as shown in FIG. 6.

3. Compound Ia (Citrate Salt).

One aspect of the present disclosure relates to a citrate salt of N-(3-(4,6-dimethylpyrimidin-5-yl)-4-(2-(pyrrolidin-1-yl) ethoxy)phenyl)cyclopropanecarboxamide (Compound Ia). The citrate salt of Compound Ia are characterized by PXRD. The physical properties for the citrate salt as determined by PXRD are summarized in Table 6 below.

TABLE 6

Figure 7:
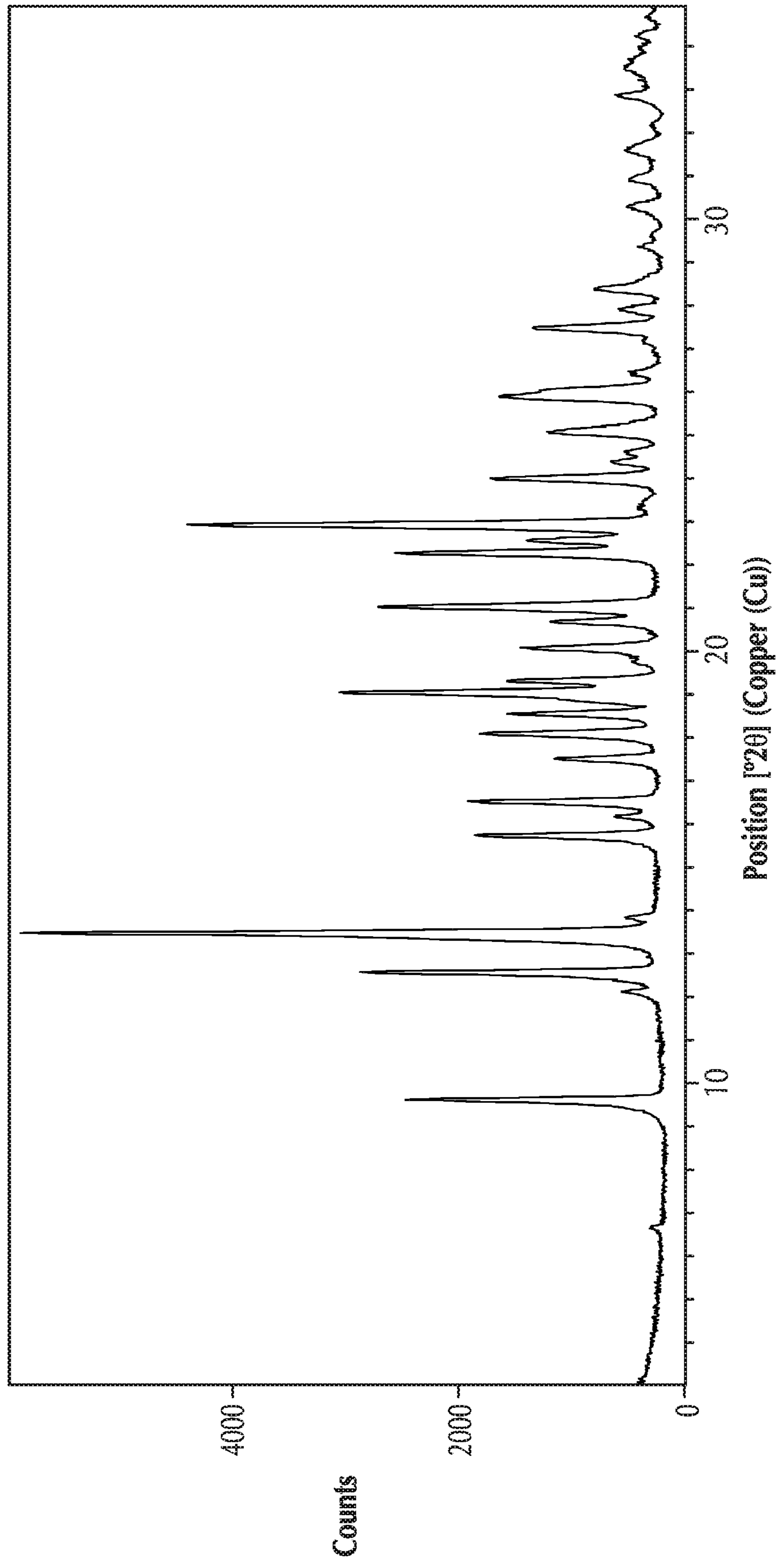
FIG. 7 shows a powder X-ray diffraction (PXRD) pattern for a sample containing a crystalline salt of Compound Ia (Citrate Salt).

| | Compound Ia (Citrate Salt, Example 6) |
|---|---|
| PXRD | FIG. 7: Peaks of about ≥6.2% relative intensity at 9.6° ± 0.2°, 12.1° ± 0.2°, 12.6° ± 0.2°, 13.5° ± 0.2°, 13.8° ± 0.2°, 15.8° ± 0.2°, 16.2° ± 0.2°, 16.6° ± 0.2°, 17.5° ± 0.2°, 18.1° ± 0.2°, 18.6° ± 0.2°, 19.1° ± 0.2°, 19.3° ± 0.2°, 20.1° ± 0.2°, 20.7° ± 0.2°, 21.1° ± 0.2°, 22.3° ± 0.2°, 22.6° ± 0.2°, 23.0° ± 0.2°, 24.0° ± 0.2°, 25.1 ± 0.2°, 25.9 ± 0.2°, 26.1 ± 0.2°, 27.5 ± 0.2°, and 28.4 ± 0.2° °2θ |

The physical properties for a citrate salt (Example 6) prepared using procedure from Example 6 are summarized in Table 7 below.

TABLE 7

Figure 8:
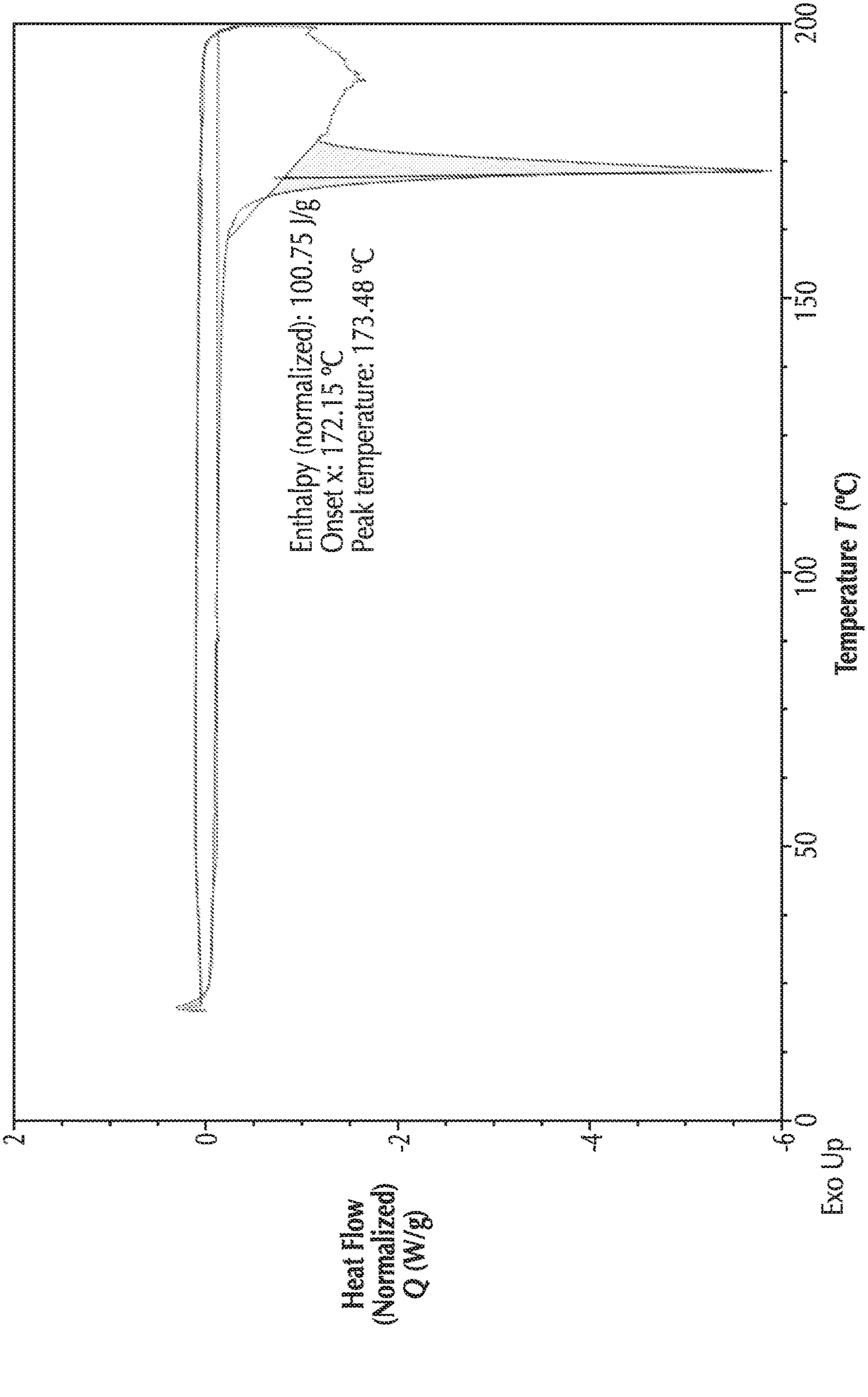
FIG. 8 shows a differential scanning calorimetry (DSC) thermogram for a sample containing a crystalline salt of Compound Ia (Citrate Salt).
Figure 9:
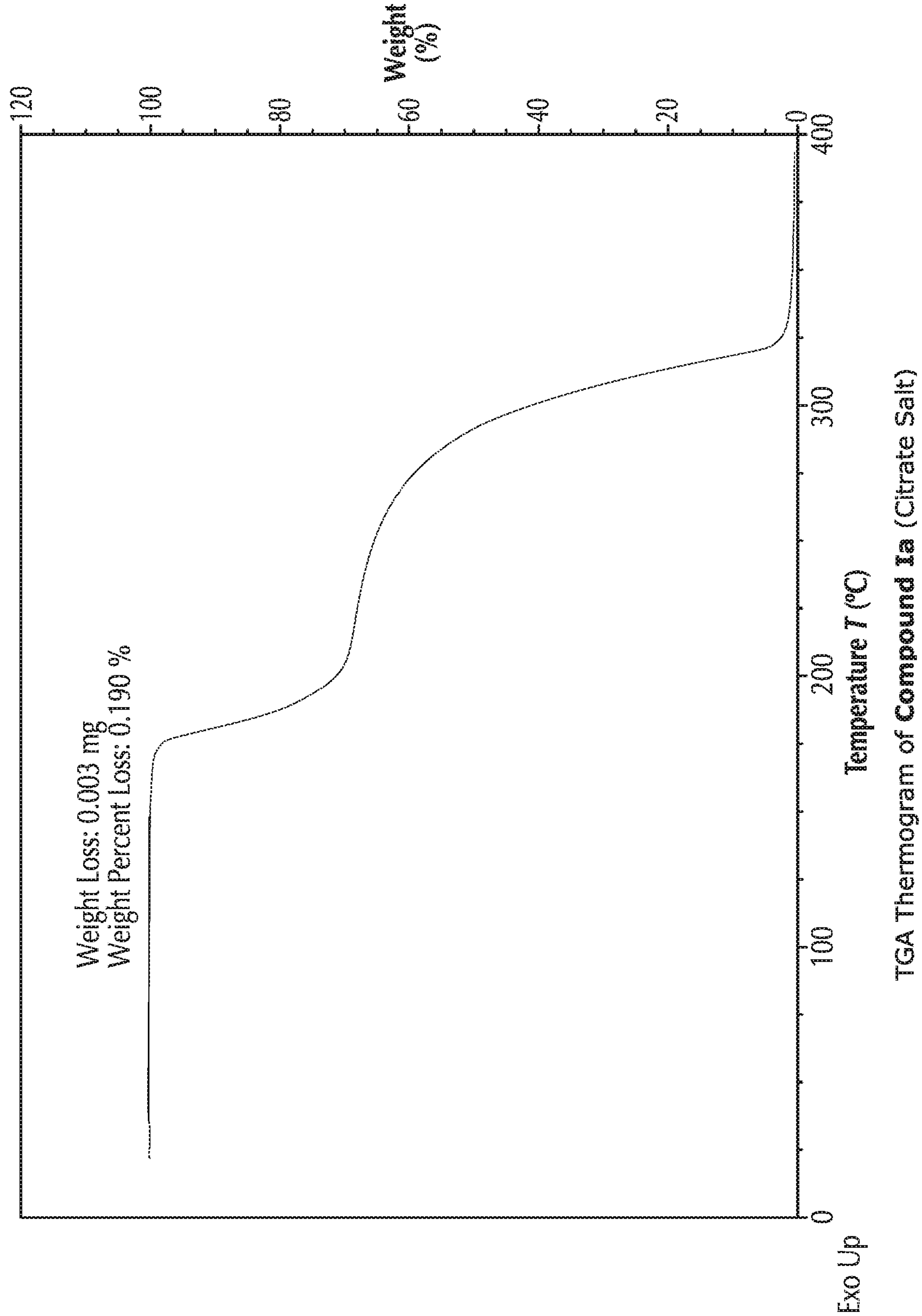
FIG. 9 shows a thermogravimetric analysis (TGA) thermogram of a sample containing a crystalline salt of Compound Ia (Citrate Salt).

| | Compound Ia (Citrate Salt, Example 6) |
|---|---|
| TGA | FIG. 9: No observable weight loss below about 175° C. |
| DSC | FIG. 8: Endotherms extrapolated onset temperature at about 172.2° C. |

Certain X-ray powder diffraction peaks for the citrate salt of N-(3-(4,6-dimethylpyrimidin-5-yl)-4-(2-(pyrrolidin-1-yl) ethoxy)phenyl)cyclopropanecarboxamide (Compound Ia) are shown in Table 8 below.

TABLE 8

| Pos. [°2θ.] | d-spacing [Å] | Rel. Int. [%] | Pos. [°2θ.] | d-spacing [Å] | Rel. Int. [%] |
|---|---|---|---|---|---|
| 6.7 | 13.3 | 1.7 | 23.4 | 3.8 | 3.8 |
| 9.6 | 9.2 | 38.4 | 24.0 | 3.7 | 26.8 |
| 12.1 | 7.3 | 6.6 | 24.4 | 3.6 | 8.5 |
| 12.6 | 7.0 | 48.0 | 24.6 | 3.6 | 6.0 |
| 13.5 | 6.6 | 100.0 | 25.1 | 3.6 | 16.4 |
| 13.8 | 6.4 | 6.2 | 25.9 | 3.4 | 20.5 |
| 15.8 | 5.6 | 29.5 | 25.9 | 3.4 | 26.1 |
| 16.2 | 5.5 | 7.8 | 26.1 | 3.4 | 16.6 |
| 16.6 | 5.4 | 29.1 | 26.5 | 3.4 | 5.0 |
| 17.5 | 5.1 | 17.1 | 27.5 | 3.2 | 20.1 |
| 18.1 | 4.9 | 28.2 | 27.9 | 3.2 | 7.2 |
| 18.6 | 4.8 | 23.8 | 28.4 | 3.1 | 11.1 |
| 19.1 | 4.7 | 50.8 | 29.4 | 3.0 | 3.6 |
| 19.3 | 4.6 | 24.4 | 30.4 | 2.9 | 5.4 |
| 19.8 | 4.5 | 4.8 | 31.0 | 2.9 | 5.6 |
| 20.1 | 4.4 | 20.7 | 31.6 | 2.8 | 6.1 |
| 20.7 | 4.3 | 18.0 | 32.2 | 2.8 | 2.0 |
| 21.1 | 4.2 | 44.7 | 32.9 | 2.7 | 7.3 |
| 22.3 | 4.0 | 41.4 | 33.5 | 2.7 | 6.2 |
| 22.6 | 3.9 | 21.4 | 34.3 | 2.6 | 4.5 |
| 23.0 | 3.9 | 74.9 | 34.7 | 2.6 | 2.6 |

One aspect of the present disclosure relates to a citrate salt of N-(3-(4,6-dimethylpyrimidin-5-yl)-4-(2-(pyrrolidin-1-yl) ethoxy)phenyl)cyclopropanecarboxamide.

One aspect of the present disclosure relates to a citrate salt having an X-ray powder diffraction pattern comprising a peak, in terms of 2θ, at 9.6°±0.2°, 12.1°±0.2°, 12.6°±0.2°, 13.5°±0.2°, 13.8°±0.2°, and 15.8°±0.2°. In some embodiments, the citrate salt has an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1°±0.2°, 18.6°±0.2°, 19.1°±0.2°, and 19.3°±0.2°. In some embodiments, the citrate salt has an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1°±0.2°, 18.6°±0.2°, 19.1°±0.2°, 19.3°±0.2°, 20.1°±0.2°, 20.7°±0.2°, 21.1°±0.2°, 22.3°±0.2°, 22.6°±0.2°, 23.0°±0.2°, and 24.0°±0.2°. In some embodiments, the citrate salt has an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1°±0.2°, 18.6°±0.2°, 19.1°±0.2°, 19.3°±0.2°, 20.1°±0.2°, 20.7°±0.2°, 21.1°±0.2°, 22.3°±0.2°, 22.6°±0.2°, 23.0°±0.2°, 24.0°±0.2°, 25.1±0.2°, and 25.9±0.2°. In some embodiments, the citrate salt has an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1° ±0.2°, 18.6°±0.2°, 19.1°±0.2°, 19.3°±0.2°, 20.1°±0.2°, 20.7°±0.2°, 21.1°±0.2°, 22.3°±0.2°, 22.6°±0.2°, 23.0°±0.2°, 24.0°±0.2°, 25.1±0.2°, 25.9±0.2°, 26.1±0.2°, 27.5±0.2°, and 28.4±0.2°. In some embodiments, the citrate salt has an X-ray powder diffraction pattern substantially as shown in FIG. 7, wherein by "substantially" is meant that the reported peaks can vary by about ±0.2° 2θ.

In some embodiments, the citrate salt has a differential scanning calorimetry thermogram comprising an endotherm with an extrapolated onset temperature between about 169.2° C. and about 176.5° C.

In some embodiments, the citrate salt has a differential scanning calorimetry thermogram comprising an endotherm with an extrapolated onset temperature between about 170.2° C. and about 176.5° C.

In some embodiments, the citrate salt has a differential scanning calorimetry thermogram comprising an endotherm with an extrapolated onset temperature between about 171.2° C. and about 175.5° C.

In some embodiments, the citrate salt has a differential scanning calorimetry thermogram comprising an endotherm with an extrapolated onset temperature between about 171.2° C. and about 174.5° C.

In some embodiments, the citrate salt has a differential scanning calorimetry thermogram comprising an endotherm with an extrapolated onset temperature at about 172.2° C.

In some embodiments, the citrate salt has a differential scanning calorimetry thermogram substantially as shown in FIG. 8, wherein by "substantially" is meant that the reported DSC features can vary by about ±4° C. and that the reported DSC features can vary by about ±20 joules per gram.

In some embodiments, the citrate salt has a thermogravimetric analysis profile showing no observable weight loss below about 175° C.

In some embodiments, the citrate salt has a thermogravimetric analysis profile substantially as shown in FIG. 9, wherein by "substantially" is meant that the reported TGA features can vary by about ±5° C., and that that the reported TGA features can vary by about ±2% weight change.

One aspect of the present disclosure relates to the citrate salt having:

a) an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1°±0.2°, 18.6°±0.2°, 19.1°±0.2°, and 19.3°±0.2°;

b) a differential scanning calorimetry thermogram comprising an endotherm with an extrapolated onset temperature between about 169.2° C. and about 176.5° C.; and/or c) a thermogravimetric analysis profile showing no observable weight loss below about 175° C.; and/or One aspect of the present disclosure relates to the citrate salt having:

a) an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1°±0.2°, 18.6°±0.2°, 19.1°±0.2°, 19.3°±0.2°, 20.1°±0.2°, 20.7°±0.2°, 21.1°±0.2°, 22.3°±0.2°, 22.6°±0.2°, 23.0°±0.2°, and 24.0°±0.2°;

b) a differential scanning calorimetry thermogram comprising an endotherm with an extrapolated onset temperature between about 170.2° C. and about 176.5° C.; and/or c) a thermogravimetric analysis profile showing no observable weight loss below about 175° C.; and/or One aspect of the present disclosure relates to the citrate salt having:

a) an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 17.5°±0.2°, 18.1° ±0.2°, 18.6°±0.2°, 19.1°±0.2°, 19.3°±0.2°, 20.1°±0.2°, 20.7°±0.2°, 21.1°±0.2°, 22.3°±0.2°, 22.6°±0.2°, 23.0°±0.2°, 24.0°±0.2°, 25.1±0.2°, and 25.9±0.2°;

b) a differential scanning calorimetry thermogram comprising an endotherm with an extrapolated onset temperature between about 171.2° C. and about 175.5° C.; and/or c) a thermogravimetric analysis profile showing no observable weight loss below about 175° C.; and/or One aspect of the present disclosure relates to the citrate salt having:

a) an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1°±0.2°, 18.6°±0.2°, 19.1°±0.2°, 19.3°±0.2°, 20.1°±0.2°, 20.7°±0.2°, 21.1°±0.2°, 22.3°±0.2°, 22.6°±0.2°, 23.0°±0.2°, 24.0°±0.2°, 25.1±0.2°, 25.9±0.2°, 26.1±0.2°, 27.5±0.2°, and 28.4±0.2°;

b) a differential scanning calorimetry thermogram comprising an endotherm with an extrapolated onset temperature between about 171.2° C. and about 174.5° C.; and/or c) a thermogravimetric analysis profile showing no observable weight loss below about 175° C.

One aspect of the present disclosure relates to the citrate salt having:

a) an X-ray powder diffraction pattern comprising peaks, in terms of 2θ, at 9.6°±0.2°, 12.1°±0.2°, 12.6°±0.2°, 13.5°±0.2°, 13.8°±0.2°, 15.8°±0.2°, 16.2°±0.2°, 16.6°±0.2°, 17.5°±0.2°, 18.1°±0.2°, 18.6°±0.2°, 19.1°±0.2°, 19.3°±0.2°, 20.1°±0.2°, 20.7°±0.2°, 21.1°±0.2°, 22.3°±0.2°, 22.6°±0.2°, 23.0°±0.2°, 24.0°±0.2°, 25.1±0.2°, 25.9±0.2°, 26.1±0.2°, 27.5±0.2°, and 28.4±0.2°;

b) a differential scanning calorimetry thermogram comprising an endotherm with an extrapolated onset temperature at about 172.2° C.; and/or c) a thermogravimetric analysis profile showing no observable weight loss below about 175° C.

One aspect of the present disclosure relates to the citrate salt having:

a) an X-ray powder diffraction pattern substantially as shown in FIG. 7;

b) a differential scanning calorimetry thermogram substantially as shown in FIG. 8; and/or c) a thermogravimetric analysis profile substantially as shown in FIG. 9.

4. Compound Ia (Fumarate Salt).

One aspect of the present disclosure relates to fumarate salt of N-(3-(4,6-dimethylpyrimidin-5-yl)-4-(2-(pyrrolidin-1-yl)ethoxy)phenyl)cyclopropanecarboxamide (Compound Ia). The fumarate salt of Compound Ia are characterized by PXRD. The physical properties for the fumarate salt as determined by PXRD are summarized in Table 9 below.

TABLE 9

Figure 10:
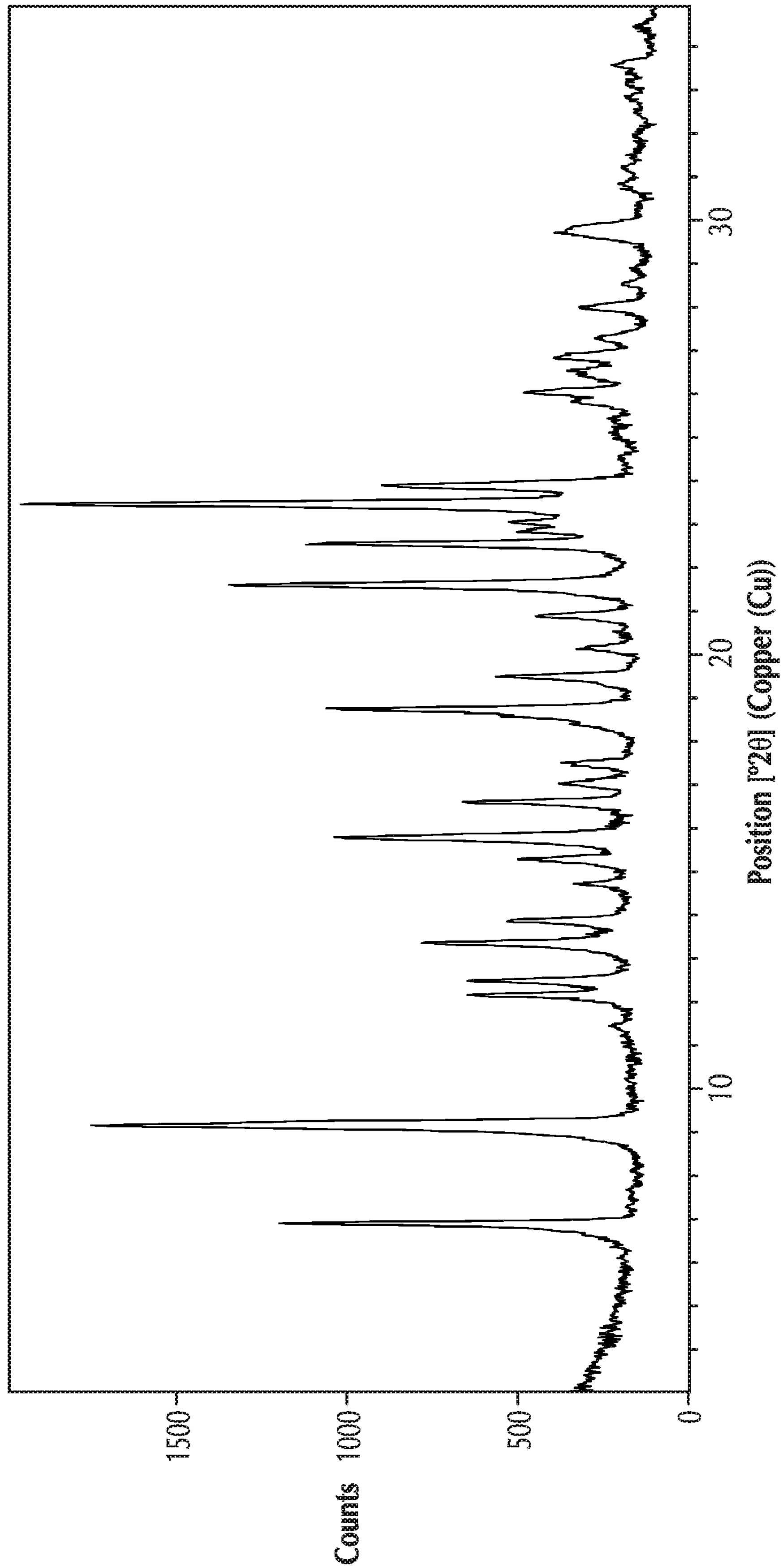
FIG. 10 shows a powder X-ray diffraction (PXRD) pattern for a sample containing a crystalline salt of Compound Ia (Fumarate Salt).

| | Compound 1 (Fumarate Salt, Example 7) |
|---|---|
| PXRD | FIG. 10: Peaks of about ≥10.0% relative intensity at 6.9° ± 0.2°, 9.2° ± 0.2°, 9.3° ± 0.2°, 12.2° ± 0.2°, 12.5° ± 0.2°, 13.4° ± 0.2°, 13.9° ± 0.2°, 14.7° ± 0.2°, 15.3° ± 0.2°, 15.8° ± 0.2°, 16.6° ± 0.2°, 17.0° ± 0.2°, 18.8° ± 0.2°, 19.5° ± 0.2°, 20.9° ± 0.2°, 21.6° ± 0.2°, 22.6° ± 0.2°, 22.9° ± 0.2°, 23.1° ± 0.2°, 23.5° ± 0.2°, 23.9° ± 0.2°, 26.1° ± 0.2°, and 26.9° ± 0.2° °2θ |

The physical properties for a fumarate salt (Example 7) prepared using procedure from Example 7 are summarized in Table 10 below.

TABLE 10

Figure 11:
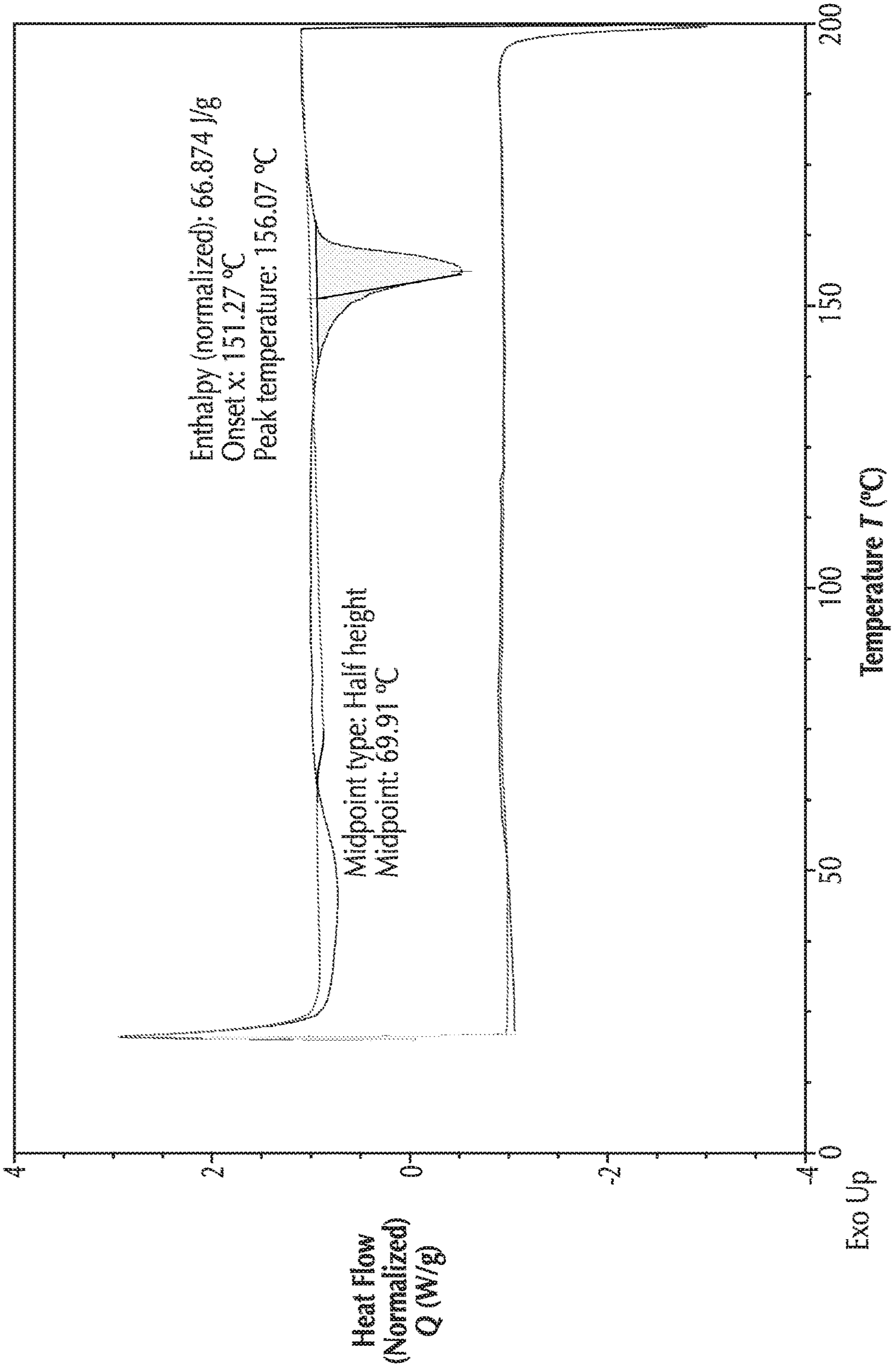
FIG. 11 shows a differential scanning calorimetry (DSC) thermogram for a sample containing a crystalline salt of Compound Ia (Fumarate Salt).
Figure 12:
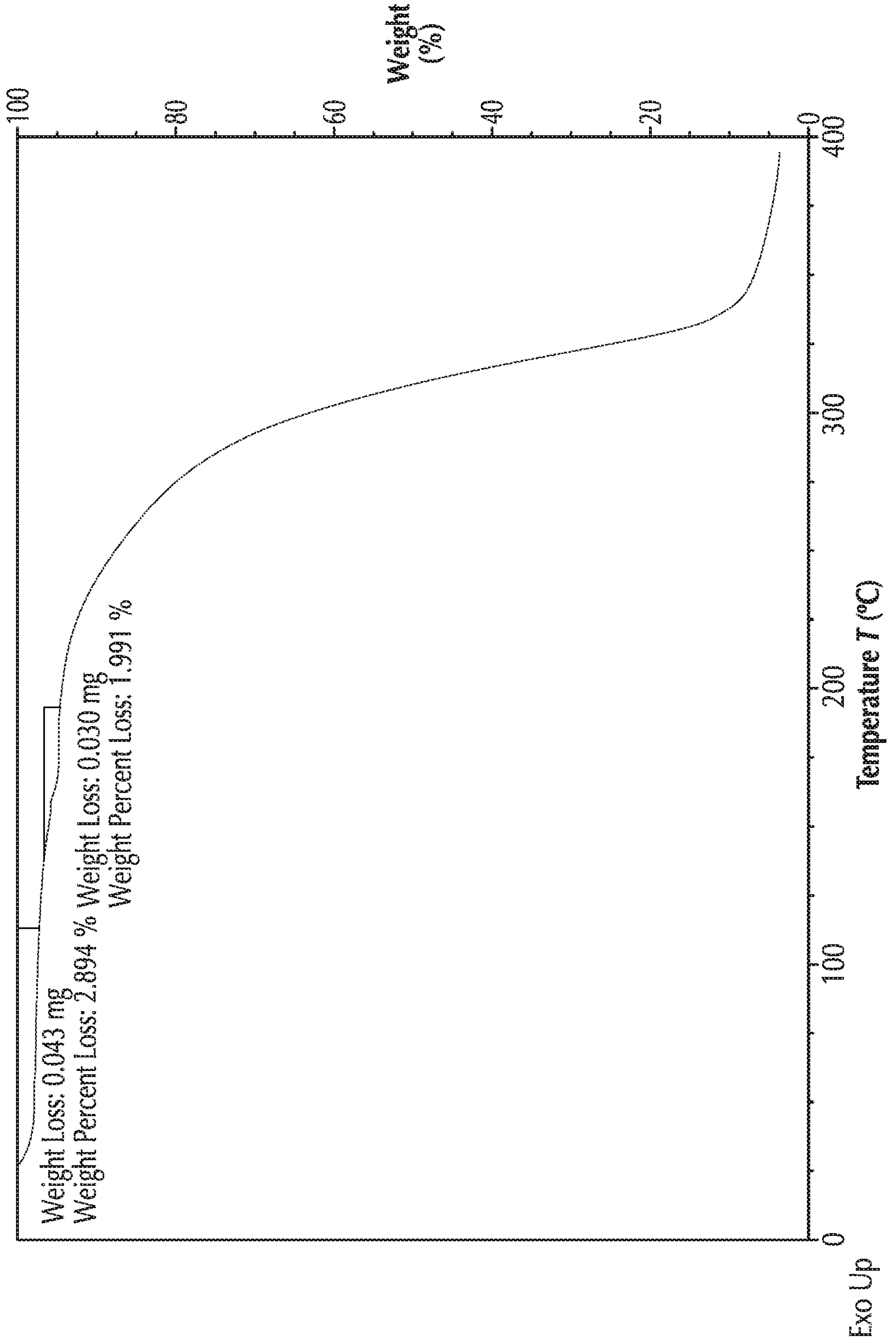
FIG. 12 shows a thermogravimetric analysis (TGA) thermogram of a sample containing a crystalline salt of Compound Ia (Fumarate Salt).

| | Compound 1 (Fumarate Salt, Example 7) |
|---|---|
| TGA | FIG. 12: Decrease in weight of about 4.9% out to about 200° C. |
| DSC | FIG. 11: Endotherm extrapolated onset temperature at about 156.1° C. |

Certain X-ray powder diffraction peaks for the fumarate salt of N-(3-(4,6-dimethylpyrimidin-5-yl)-4-(2-(pyrrolidin-1-yl)ethoxy)phenyl)cyclopropanecarboxamide (Compound Ia) are shown in Table 11 below.

TABLE 11

| Pos. [°2θ.] | d-spacing [Å] | Rel. Int. [%] | Pos. [°2θ.] | d-spacing [Å] | Rel. Int. [%] |
|---|---|---|---|---|---|
| 6.4 | 13.7 | 100.0 | 15.7 | 5.6 | 7.6 |
| 7.3 | 12.0 | 38.4 | 18.8 | 4.7 | 8.4 |
| 7.8 | 11.3 | 67.0 | 19.4 | 4.6 | 5.2 |
| 10.6 | 8.4 | 25.3 | 21.1 | 4.2 | 4.2 |
| 11.1 | 7.9 | 11.3 | 21.6 | 4.1 | 4.6 |
| 12.9 | 6.9 | 8.5 | 22.2 | 4.0 | 3.7 |
| 13.7 | 6.5 | 8.2 | 23.6 | 3.8 | 8.8 |
| 14.3 | 6.2 | 18.1 | 26.0 | 3.4 | 5.9 |
| 14.7 | 6.0 | 21.1 | | | |

One aspect of the present disclosure relates to an fumarate salt of N-(3-(4,6-dimethylpyrimidin-5-yl)-4-(2-(pyrrolidin-1-yl)ethoxy)phenyl)cyclopropanecarboxamide.

One aspect of the present disclosure relates to an fumarate salt having an X-ray powder diffraction pattern comprising a peak, in terms of 2θ, at 6.9°±0.2°, 9.2°±0.2°, 9.3°±0.2°, and 12.2°±0.2°. In some embodiments, the fumarate salt has an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, and 15.8°±0.2°. In some embodiments, the fumarate salt has an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, 15.8°±0.2°, 16.6°±0.2°, 17.0°±0.2°, 18.8°±0.2°, and 19.5°±0.2°. In some embodiments, the fumarate salt has an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, 15.8°±0.2°, 16.6°±0.2°, 17.0°±0.2°, 18.8°±0.2°, 19.5°±0.2°, 20.9°±0.2°, 21.6°±0.2°, 22.6°±0.2°, and 22.9°±0.2°. In some embodiments, the fumarate salt has an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, 15.8°±0.2°, 16.6°±0.2°, 17.0°±0.2°, 18.8°±0.2°, 19.5°±0.2°, 20.9°±0.2°, 21.6°±0.2°, 22.6°±0.2°, 22.9°±0.2°, 23.1°±0.2°, 23.5°±0.2°, 23.9°±0.2°, 26.1°±0.2°, and 26.9°±0.2° In some embodiments, the fumarate salt has an X-ray powder diffraction pattern substantially as shown in FIG. 10, wherein by "substantially" is meant that the reported peaks can vary by about ±0.2° 2θ.

In some embodiments, the fumarate salt has a differential scanning calorimetry thermogram comprising an endotherm with an extrapolated onset temperature between about 148.3° C. and about 159.1° C.

In some embodiments, the fumarate salt has a differential scanning calorimetry thermogram comprising an endotherm with an extrapolated onset temperature between about 149.3° C. and about 158.1° C.

In some embodiments, the fumarate salt has a differential scanning calorimetry thermogram comprising an endotherm with an extrapolated onset temperature between about 149.3° C. and about 157.1° C.

In some embodiments, the fumarate salt has a differential scanning calorimetry thermogram comprising an endotherm with an extrapolated onset temperature between about 150.3° C. and about 157.1° C.

In some embodiments, the fumarate salt has a differential scanning calorimetry thermogram comprising an endotherm with an extrapolated onset temperature at about 156.1° C. In some embodiments, the fumarate salt has a differential scanning calorimetry thermogram substantially as shown in FIG. 11, wherein by "substantially" is meant that the reported DSC features can vary by about ±4° C. and that the reported DSC features can vary by about ±20 joules per gram.

In some embodiments, the fumarate salt has a thermogravimetric analysis profile showing about 5.5% weight loss below about 200° C.

In some embodiments, the fumarate has a thermogravimetric analysis profile showing about 5.3% weight loss below about 200° C.

In some embodiments, the fumarate salt has a thermogravimetric analysis profile showing about 5.1% weight loss below about 200° C.

In some embodiments, the fumarate salt has a thermogravimetric analysis profile showing about 4.9% weight loss below about 200° C.

In some embodiments, the fumarate salt has a thermogravimetric analysis profile substantially as shown in FIG. 12, wherein by "substantially" is meant that the reported TGA features can vary by about ±5° C., and that that the reported TGA features can vary by about ±2% weight change.

One aspect of the present disclosure relates to the fumarate salt having:

a) an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, and 15.8°±0.2°;

b) a differential scanning calorimetry thermogram comprising an endotherm with an extrapolated onset temperature between about 148.3° C. and about 159.1° C.; and/or c) a thermogravimetric analysis profile showing about 5.5% weight loss below about 200° C.

One aspect of the present disclosure relates to the fumarate salt having:

a) an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, 15.8°±0.2°, 16.6°±0.2°, 17.0°±0.2°, 18.8°±0.2°, and 19.5°±0.2°;

b) a differential scanning calorimetry thermogram comprising an endotherm with an extrapolated onset temperature between about 149.3° C. and about 158.1° C.; and/or c) a thermogravimetric analysis profile showing about 5.3% weight loss below about 200° C.

One aspect of the present disclosure relates to the fumarate salt having:

a) an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 15.3°±0.2°, 15.8°±0.2°, 16.6°±0.2°, 17.0°±0.2°, 18.8°±0.2°, 19.5°±0.2°, 20.9°±0.2°, 21.6°±0.2°, 22.6°±0.2°, and 22.9°±0.2°;

b) a differential scanning calorimetry thermogram comprising an endotherm with an extrapolated onset temperature between about 149.3° C. and about 157.1° C.; and/or c) a thermogravimetric analysis profile showing about 5.1% weight loss or less below about 200° C.

One aspect of the present disclosure relates to the fumarate salt having:

a) an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, 15.8°±0.2°, 16.6°±0.2°, 17.0°±0.2°, 18.8°±0.2°, 19.5°±0.2°, 20.9°±0.2°, 21.6°±0.2°, 22.6°±0.2°, and 22.9°±0.2°;

b) a differential scanning calorimetry thermogram comprising an endotherm with an extrapolated onset temperature between about 150.3° C. and about 157.1° C.; and/or c) a thermogravimetric analysis profile showing about 4.9% weight loss or less below about 200° C.

One aspect of the present disclosure relates to the fumarate salt having:

a) an X-ray powder diffraction pattern comprising peaks, in terms of 2θ, at 6.9°±0.2°, 9.2°±0.2°, 9.3°±0.2°, 12.2°±0.2°, 12.5°±0.2°, 13.4°±0.2°, 13.9°±0.2°, 14.7°±0.2°, 15.3°±0.2°, 15.8°±0.2°, 16.6°±0.2°, 17.0°±0.2°, 18.8°±0.2°, 19.5°±0.2°, 20.9°±0.2°, 21.6°±0.2°, 22.6°±0.2°, 22.9°±0.2°, 23.1°±0.2°, 23.5°±0.2°, 23.9°±0.2°, 26.1°±0.2°, and 26.9°±0.2°;

b) a differential scanning calorimetry thermogram comprising an endotherm with an extrapolated onset temperature at about 156.1° C.; and/or c) a thermogravimetric analysis profile showing about 4.9% weight loss or less below about 200° C.

One aspect of the present disclosure relates to the fumarate salt having:

a) an X-ray powder diffraction pattern substantially as shown in FIG. 10;

b) a differential scanning calorimetry thermogram substantially as shown in FIG. 11; and/or c) a thermogravimetric analysis profile substantially as shown in FIG. 12.

5. Compound Ia (Hydrochloride Salt).

One aspect of the present disclosure relates to a hydrochloride salt of N-(3-(4,6-dimethylpyrimidin-5-yl)-4-(2-(pyrrolidin-1-yl)ethoxy)phenyl)cyclopropanecarboxamide (Compound Ia). The hydrochloride salt of Compound Ia are characterized by PXRD. The physical properties for the fumarate salt as determined by PXRD are summarized in Table 12 below.

TABLE 12

| | Compound Ia (Hydrochloride Salt, Example 8) |
|---|---|
| PXRD | FIG. 10: Peaks of about ≥8.3% relative intensity at 12.4° ± 0.2°, 12.8° ± 0.2°, 13.8° ± 0.2°, 15.9° ± 0.2°, 16.2° ± 0.2°, 18.4° ± 0.2°, 20.8° ± 0.2°, 23.2° ± 0.2°, 23.5° ± 0.2°, 24.8° ± 0.2°, 27.7° ± 0.2°, 27.8° ± 0.2°, and 32.7° ± 0.2° °2θ |

The physical properties for a hydrochloride salt (Example 8) prepared using procedure from Example 8 are summarized in Table 13 below.

TABLE 13

| | Compound Ia (Hydrochloride Salt, Example 8) |
|---|---|
| TGA | FIG. 12: Decrease in weight of about 4.3% out to about 100° C. |
| DSC | FIG. 11: Endotherms extrapolated onset temperature at about 23.8° C. and at about 188.5° C. |

Certain X-ray powder diffraction peaks for the hydrochloride salt of N-(3-(4,6-dimethylpyrimidin-5-yl)-4-(2-(pyrrolidin-1-yl)ethoxy)phenyl)cyclopropanecarboxamide (Compound Ia) are shown in Table 14 below.

TABLE 14

| Pos. [°2θ.] | d-spacing [Å] | Rel. Int. [%] |
|---|---|---|
| 6.4 | 13.8 | 9.2 |
| 6.9 | 12.8 | 7.0 |
| 9.0 | 9.9 | 6.7 |
| 9.6 | 9.2 | 1.8 |
| 12.0 | 7.3 | 6.0 |
| 12.4 | 7.2 | 61.0 |
| 12.5 | 7.1 | 7.5 |
| 12.8 | 6.9 | 28.3 |
| 13.8 | 6.4 | 10.3 |
| 14.1 | 6.3 | 2.1 |
| 15.9 | 5.6 | 55.8 |
| 16.2 | 5.5 | 65.4 |
| 16.7 | 5.3 | 5.7 |
| 17.8 | 5.0 | 5.2 |
| 18.4 | 4.8 | 34.0 |
| 18.8 | 4.7 | 3.7 |
| 19.3 | 4.6 | 2.0 |
| 20.1 | 4.4 | 1.8 |
| 20.8 | 4.3 | 8.3 |

TABLE 14-continued

| Pos. [°2θ.] | d-spacing [Å] | Rel. Int. [%] |
|---|---|---|
| 21.4 | 4.1 | 3.0 |
| 21.9 | 4.1 | 3.1 |
| 22.2 | 4.0 | 5.7 |
| 22.9 | 3.9 | 3.1 |
| 23.2 | 3.8 | 18.0 |
| 23.5 | 3.8 | 16.2 |
| 23.9 | 3.7 | 4.7 |
| 24.8 | 3.6 | 27.8 |
| 24.8 | 3.6 | 26.6 |
| 26.6 | 3.3 | 3.0 |
| 27.7 | 3.2 | 100.0 |
| 27.8 | 3.2 | 51.2 |
| 29.4 | 3.0 | 2.3 |
| 30.4 | 2.9 | 9.9 |
| 31.4 | 2.8 | 2.6 |
| 32.2 | 2.8 | 3.3 |
| 32.7 | 2.7 | 19.6 |
| 32.8 | 2.7 | 10.7 |
| 34.2 | 2.6 | 3.8 |

One aspect of the present disclosure relates to an hydrochloride salt of N-(3-(4,6-dimethylpyrimidin-5-yl)-4-(2-(pyrrolidin-1-yl)ethoxy)phenyl)cyclopropanecarboxamide.

One aspect of the present disclosure relates to an hydrochloride salt having an X-ray powder diffraction pattern comprising a peak, in terms of 2θ, at 12.4°±0.2°, 12.8°±0.2°, and 13.8°±0.2°. In some embodiments, the hydrochloride salt has an X-ray powder diffraction pattern comprising peaks, in terms of 2θ, at 12.4°±0.2°, 12.8°±0.2°, 13.8°±0.2°, 15.9°±0.2°, and 16.2°±0.2°.

In some embodiments, the hydrochloride salt has an X-ray powder diffraction pattern comprising peaks, in terms of 2θ, at 12.4°±0.2°, 12.8°±0.2°, 13.8°±0.2°, 15.9°±0.2°, 16.2°±0.2°, 18.4°±0.2°, 20.8°±0.2°, 23.2°±0.2°, and 23.5°±0.2°.

In some embodiments, the hydrochloride salt has an X-ray powder diffraction pattern comprising peaks, in terms of 2θ, at 12.4°±0.2°, 12.8°±0.2°, 13.8°±0.2°, 15.9°±0.2°, 16.2°±0.2°, 18.4°±0.2°, 20.8°±0.2°, 23.2°±0.2°, 23.5°±0.2°, and 24.8°±0.2°.

In some embodiments, the hydrochloride salt has an X-ray powder diffraction pattern comprising peaks, in terms of 2θ, at 12.4°±0.2°, 12.8°±0.2°, 13.8°±0.2°, 15.9°±0.2°, 16.2°±0.2°, 18.4°±0.2°, 20.8°±0.2°, 23.2°±0.2°, 23.5°±0.2°, 24.8°±0.2°, 27.7°±0.2°, 27.8°±0.2°, and 32.7°±0.2°.

Figure 13:
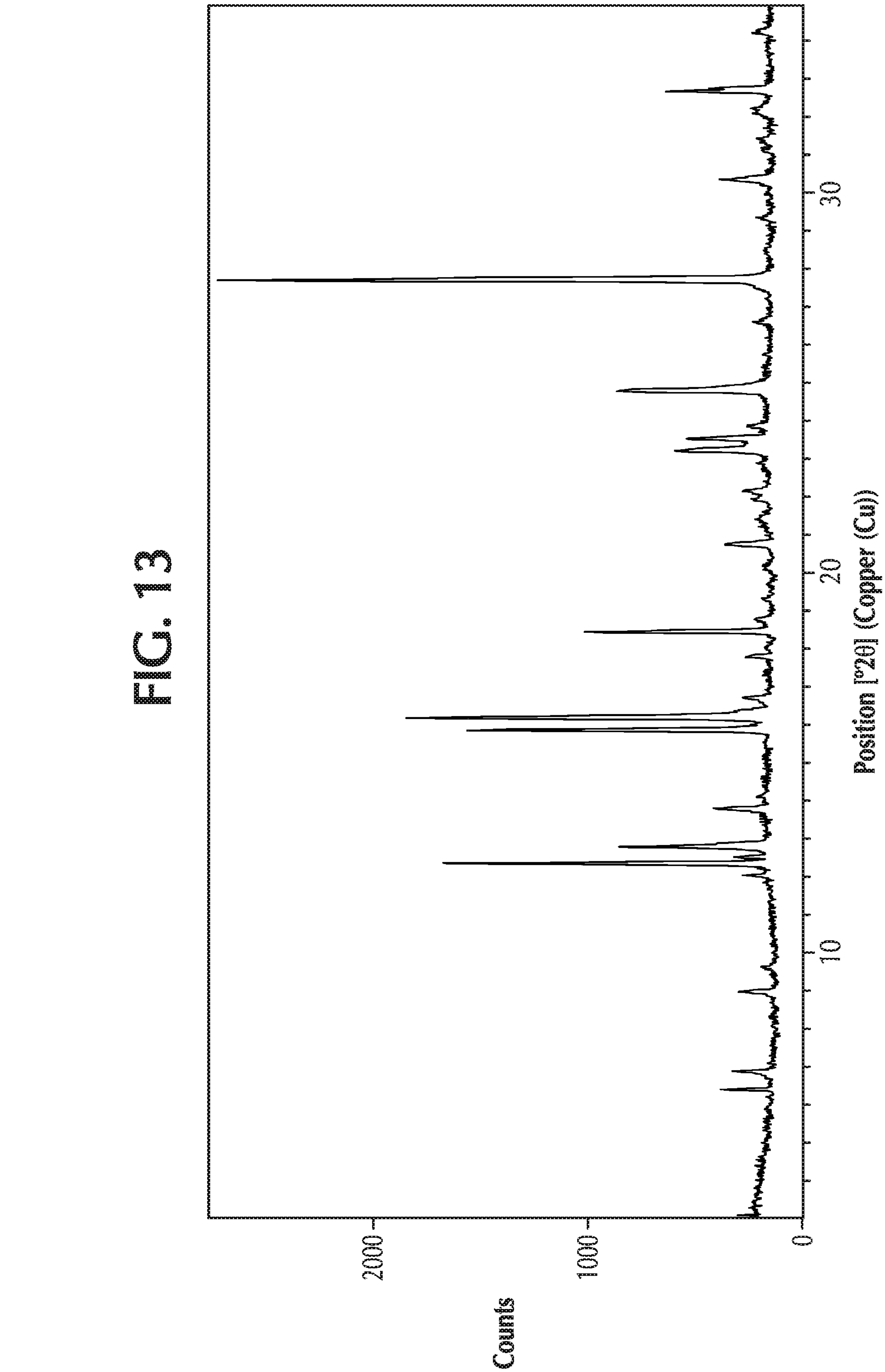
FIG. 13 shows a powder X-ray diffraction (PXRD) pattern for a sample containing a crystalline salt of Compound Ia (Hydrochloride Salt).

In some embodiments, the hydrochloride salt has an X-ray powder diffraction pattern substantially as shown in FIG. 13, wherein by "substantially" is meant that the reported peaks can vary by about ±0.2° 2θ.

In some embodiments, the hydrochloride salt has a differential scanning calorimetry thermogram comprising endotherms with an extrapolated onset temperature between about 20.8° C. and about 77.6° C. and between about 185.5° C. and about 196.9° C. . . .

In some embodiments, the hydrochloride salt has a differential scanning calorimetry thermogram comprising endotherms with an extrapolated onset temperature between about 21.8° C. and about 76.6° C. and between about 186.5° C. and about 195.9° C.

In some embodiments, the hydrochloride salt has a differential scanning calorimetry thermogram comprising endotherms with an extrapolated onset temperature between about 21.8° C. and about 74.6° C. and between about 186.5° C. and about 194.9° C.

In some embodiments, the hydrochloride salt has a differential scanning calorimetry thermogram comprising endotherms with an extrapolated onset temperature between about 22.8° C. and about 75.6° C. and between about 187.5° C. and about 194.9° C.

In some embodiments, the hydrochloride salt has a differential scanning calorimetry thermogram comprising endotherms with an extrapolated onset temperature at about 23.8° C. and at about 188.5° C.

Figure 14:
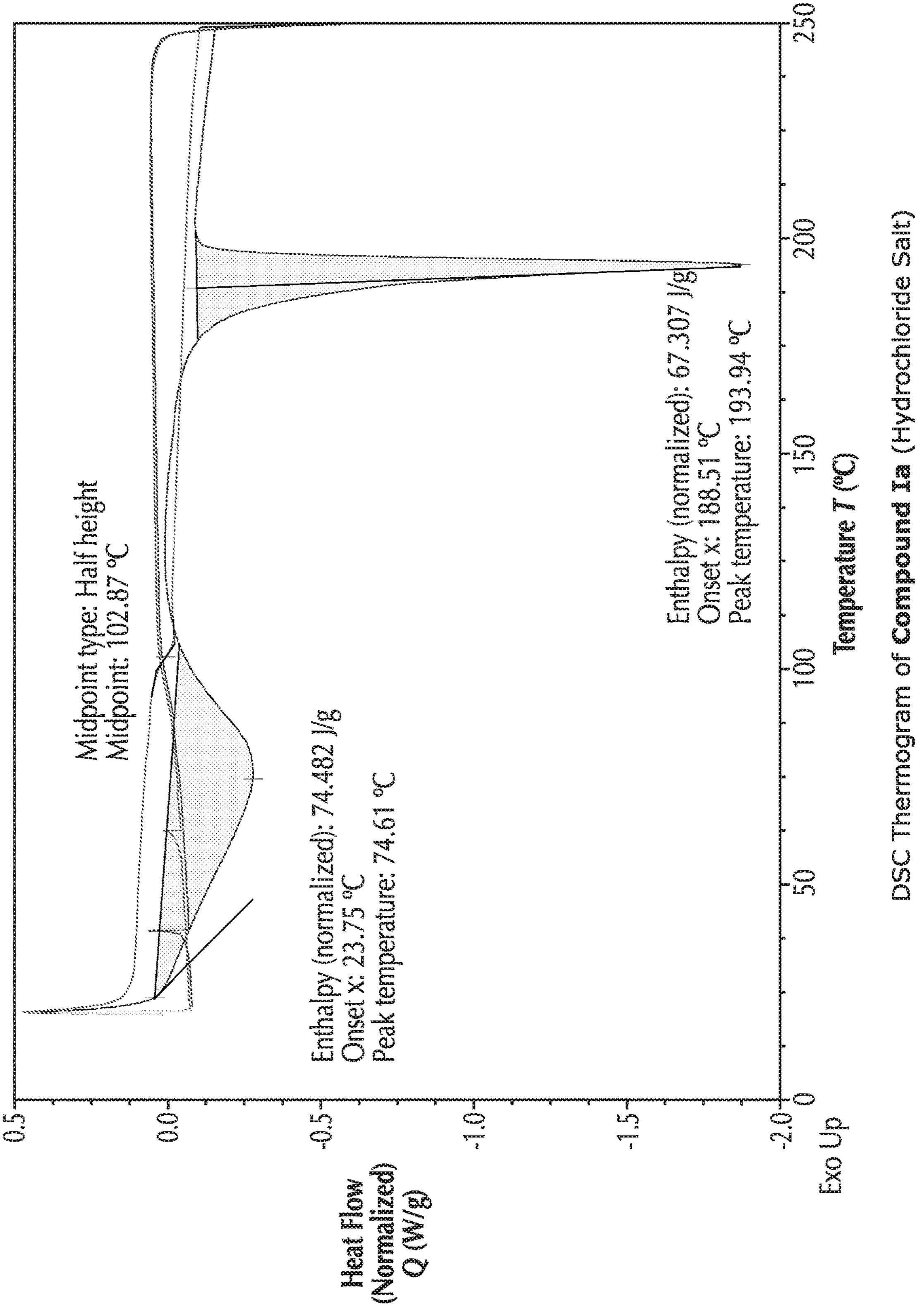
FIG. 14 shows a differential scanning calorimetry (DSC) thermogram for a sample containing a crystalline salt of Compound Ia (Hydrochloride Salt).

In some embodiments, the hydrochloride salt has a differential scanning calorimetry thermogram substantially as shown in FIG. 14, wherein by "substantially" is meant that the reported DSC features can vary by about ±4° C. and that the reported DSC features can vary by about ±20 joules per gram.

In some embodiments, the hydrochloride salt has a thermogravimetric analysis profile showing about 5.0% weight loss below about 100° C.

In some embodiments, the hydrochloride salt has a thermogravimetric analysis profile showing about 4.8% weight loss below about 100° C.

In some embodiments, the hydrochloride salt has a thermogravimetric analysis profile showing about 4.6% weight loss below about 100° C.

In some embodiments, the hydrochloride salt has a thermogravimetric analysis profile showing about 4.3% weight loss below about 100° C.

Figure 15:
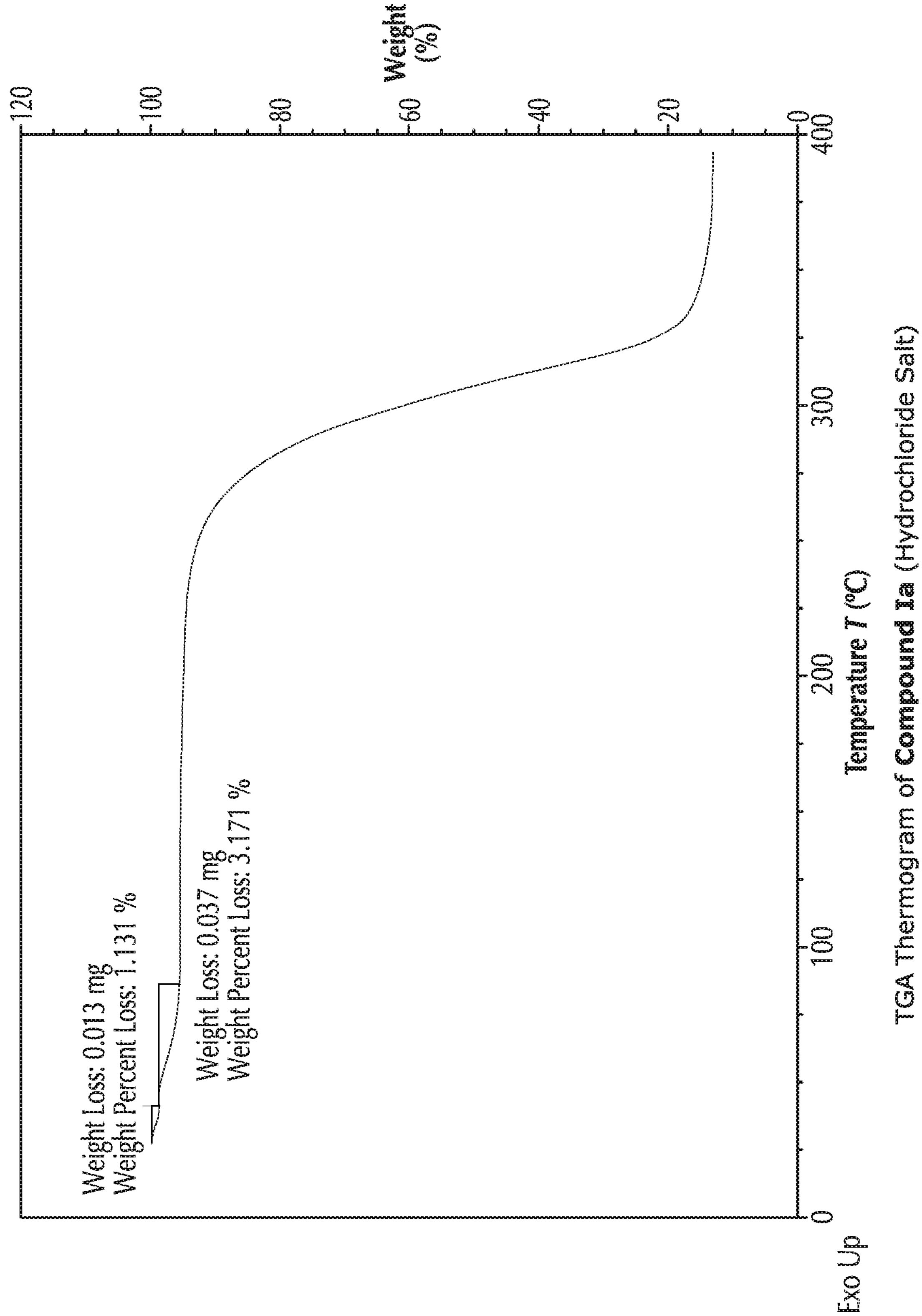
FIG. 15 shows a thermogravimetric analysis (TGA) thermogram of a sample containing a crystalline salt of Compound Ia (Hydrochloride Salt).

In some embodiments, the hydrochloride salt has a thermogravimetric analysis profile substantially as shown in FIG. 15, wherein by "substantially" is meant that the reported TGA features can vary by about ±5° C., and that that the reported TGA features can vary by about ±2% weight change.

One aspect of the present disclosure relates to the hydrochloride salt having:

a) an X-ray powder diffraction pattern comprising peaks, in terms of 2θ, at 12.4°±0.2°, 12.8°±0.2°, 13.8°±0.2°, 15.9°±0.2°, and 16.2°±0.2°;
b) a differential scanning calorimetry thermogram comprising endotherms with an extrapolated onset temperature between about 20.8° C. and about 77.6° C. and between about 185.5° C. and about 196.9° C.; and/or
c) a thermogravimetric analysis profile showing about 5.0% weight loss below about 200° C.

One aspect of the present disclosure relates to the hydrochloride salt having:

a) an X-ray powder diffraction pattern comprising peaks, in terms of 2θ, at 12.4°±0.2°, 12.8°±0.2°, 13.8°±0.2°, 15.9°±0.2°, 16.2°±0.2°, 18.4°±0.2°, 20.8°±0.2°, 23.2°±0.2°, and 23.5°±0.2°;
b) a differential scanning calorimetry thermogram comprising endotherms with an extrapolated onset temperature between about 21.8° C. and about 76.6° C. and between about 186.5° C. and about 195.9° C.; and/or
c) a thermogravimetric analysis profile showing about 4.8% weight loss below about 200° C.

One aspect of the present disclosure relates to the hydrochloride salt having:

a) an X-ray powder diffraction pattern comprising peaks, in terms of 2θ, at 12.4°±0.2°, 12.8°±0.2°, 13.8°±0.2°, 15.9°±0.2°, 16.2°±0.2°, 18.4°±0.2°, 20.8°±0.2°, 23.2°±0.2°, 23.5°±0.2°, and 24.8°±0.2°;
b) a differential scanning calorimetry thermogram comprising endotherms with an extrapolated onset temperature between about 21.8° C. and about 75.6° C. and between about 186.5° C. and about 194.9° C.; and/or
c) a thermogravimetric analysis profile showing about 4.6% weight loss below about 100° C.

One aspect of the present disclosure relates to the hydrochloride salt having:

a) an X-ray powder diffraction pattern comprising peaks, in terms of 2θ, at 12.4°±0.2°, 12.8°±0.2°, 13.8°±0.2°, 15.9°±0.2°, 16.2°±0.2°, 18.4°±0.2°, 20.8°±0.2°, 23.2°±0.2°, 23.5°±0.2°, and 24.8°±0.2°;
b) a differential scanning calorimetry thermogram comprising endotherms with an extrapolated onset temperature between about 22.8° C. and about 75.6° C. and between about 187.5° C. and about 194.9° C.; and/or
c) a thermogravimetric analysis profile showing about 4.3% weight loss or less below about 100° C.

One aspect of the present disclosure relates to the hydrochloride salt having:

a) an X-ray powder diffraction pattern comprising peaks, in terms of 2θ, at 12.4°±0.2°, 12.8°±0.2°, 13.8°±0.2°, 15.9°±0.2°, 16.2°±0.2°, 18.4°±0.2°, 20.8°±0.2°, 23.2°±0.2°, 23.5°±0.2°, 24.8°±0.2°, 27.7°±0.2°, 27.8°±0.2°, and 32.7°±0.2°;
b) a differential scanning calorimetry thermogram comprising endotherms with an extrapolated onset temperature at about 23.8° C. and at about 188.5° C.; and/or
c) a thermogravimetric analysis profile showing about 4.3% weight loss or less below about 100° C.

One aspect of the present disclosure relates to the hydrochloride salt having:

a) an X-ray powder diffraction pattern substantially as shown in FIG. 13;
b) a differential scanning calorimetry thermogram substantially as shown in FIG. 14; and/or
c) a thermogravimetric analysis profile substantially as shown in FIG. 15.

6. Compound 1 (Mesylate Salt).

One aspect of the present disclosure relates to mesylate salt of N-(3-(4,6-dimethylpyrimidin-5-yl)-4-(2-(pyrrolidin-1-yl)ethoxy)phenyl)cyclopropanecarboxamide (Compound Ia). The mesylate salt of Compound Ia are characterized by PXRD. The physical properties for the mesylate salt as determined by PXRD are summarized in Table 15 below.

TABLE 15

Figure 16:
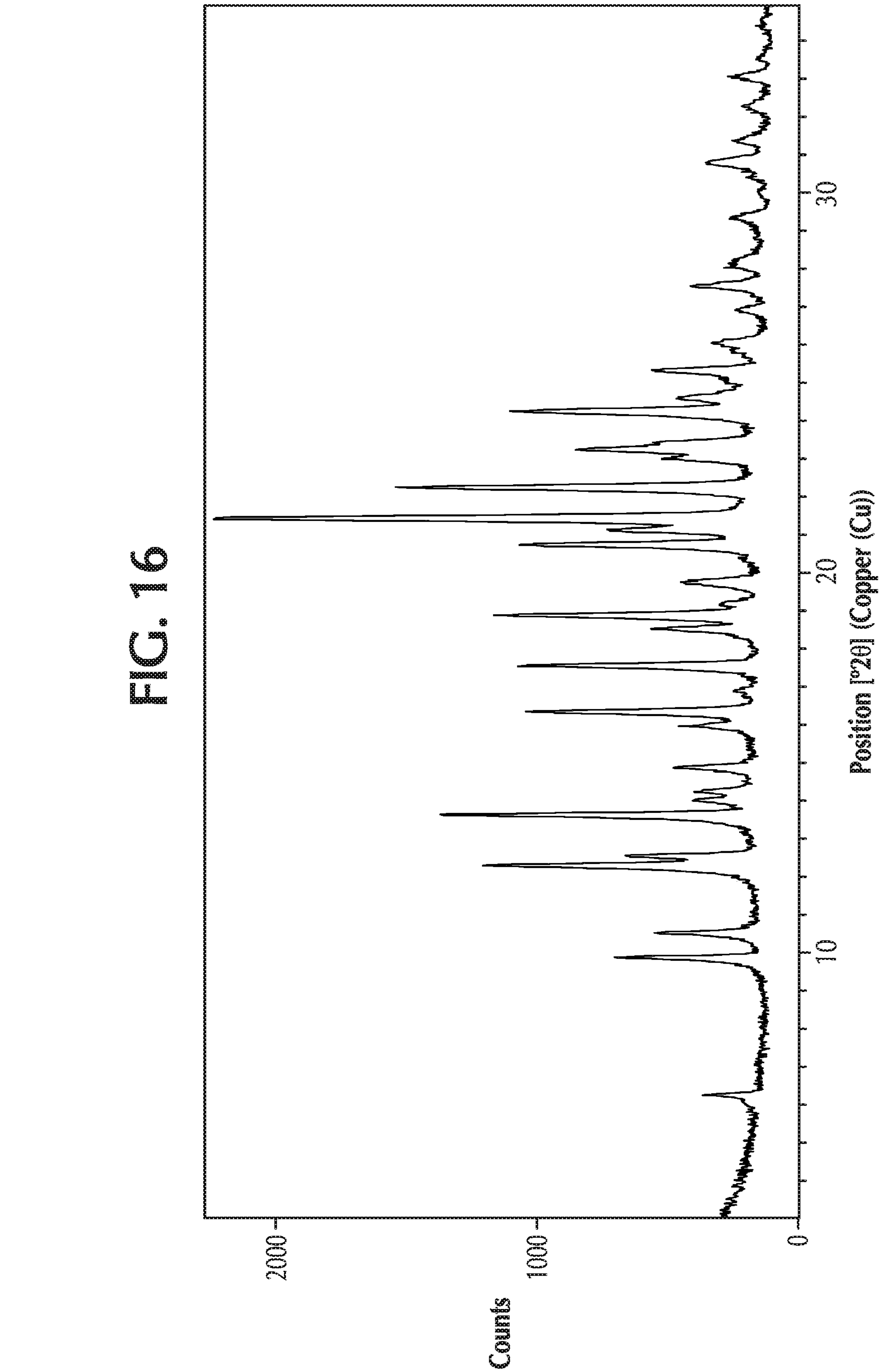
FIG. 16 shows a powder X-ray diffraction (PXRD) pattern for a sample containing a crystalline salt of Compound Ia (Mesylate Salt).

| | Compound Ia (Mesylate Salt, Example 9) |
|---|---|
| PXRD | FIG. 16: Peaks of about ≥9.8% relative intensity at 6.3° ± 0.2°, 9.9° ± 0.2°, 10.5° ± 0.2°, 12.3° ± 0.2°, 12.6° ± 0.2°, 13.6° ± 0.2°, 14.0° ± 0.2°, 14.3° ± 0.2°, 14.9° ± 0.2°, 15.9° ± 0.2°, 16.4° ± 0.2°, 17.6° ± 0.2°, 18.5° ± 0.2°, 18.9° ± 0.2°, 19.7° ± 0.2°, 20.8° ± 0.2°, 21.1° ± 0.2°, 21.4° ± 0.2°, 22.3° ± 0.2°, 23.0° ± 0.2°, 23.3° ± 0.2°, 23.5° ± 0.2°, 24.3° ± 0.2°, 24.6° ± 0.2°, 25.3° ± 0.2°, and 27.5° ± 0.2° °2θ |

The physical properties for a mesylate salt (Example 9) prepared using procedure from Example 9 are summarized in Table 16 below.

TABLE 16

Figure 17:
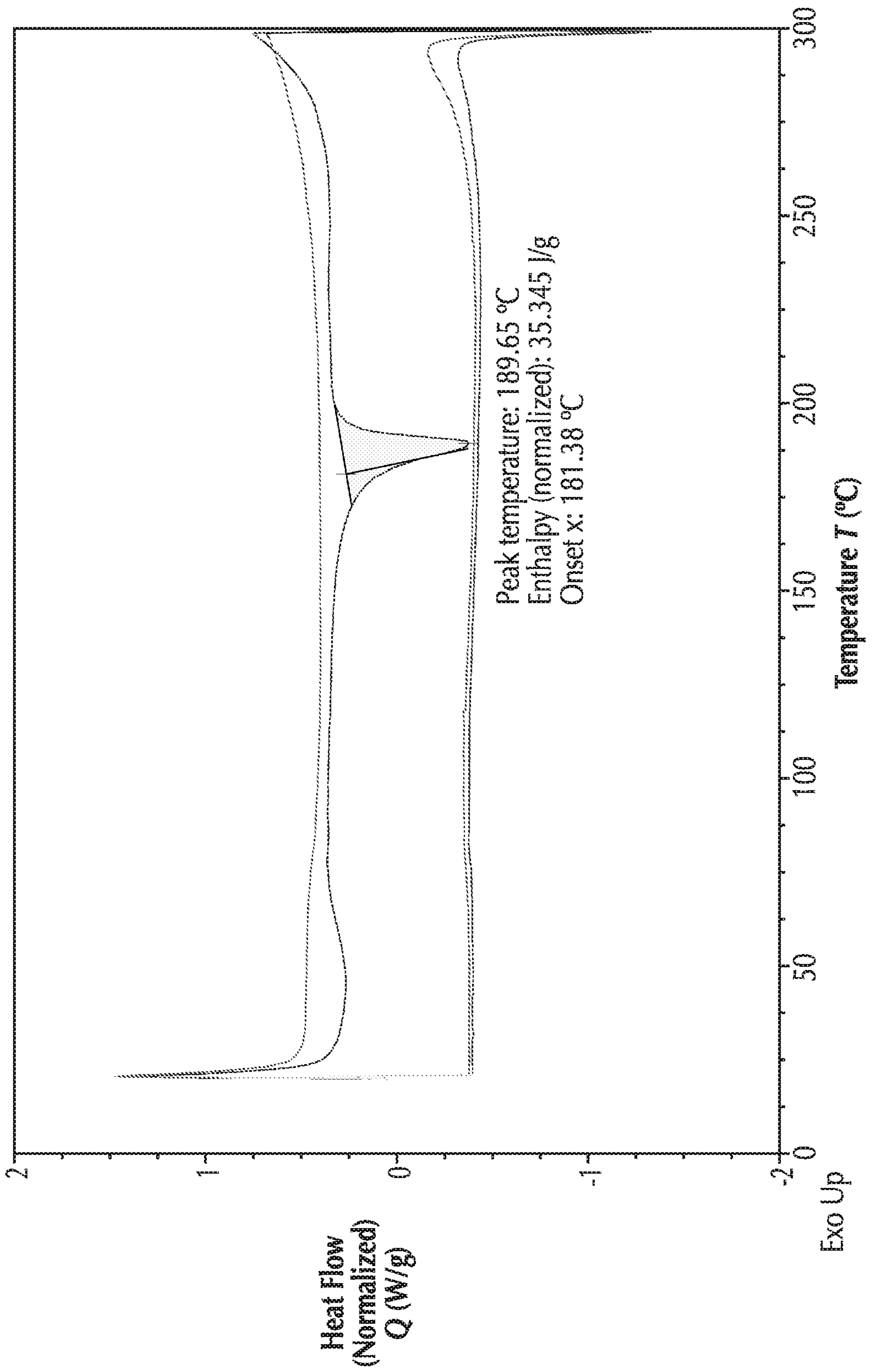
FIG. 17 shows a differential scanning calorimetry (DSC) thermogram for a sample containing a crystalline salt of Compound Ia (Mesylate Salt).
Figure 18:
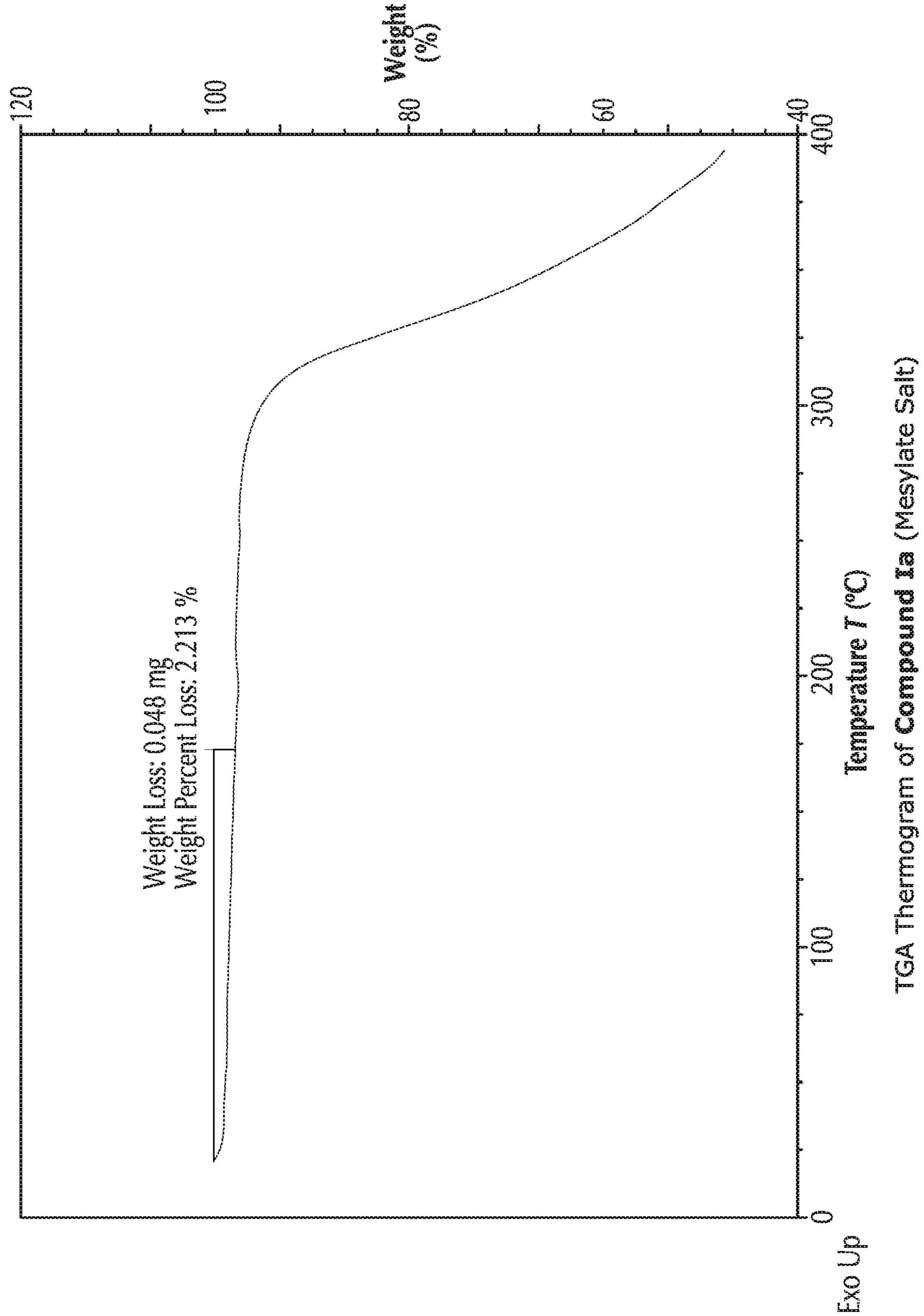
FIG. 18 shows a thermogravimetric analysis (TGA) thermogram of a sample containing a crystalline salt of Compound Ia (Mesylate Salt).

| | Compound Ia (Mesylate Salt, Example 9) |
|---|---|
| TGA | FIG. 18: Decrease in weight of about 2.2% out to about 180° C. |
| DSC | FIG. 17: Endotherm extrapolated onset temperature at about 181.4° C. |

Certain X-ray powder diffraction peaks for the methanol solvates of N-(3-(4,6-dimethylpyrimidin-5-yl)-4-(2-(pyrrolidin-1-yl)ethoxy)phenyl)cyclopropanecarboxamide (Compound Ia) are shown in Table 17 below.

TABLE 17

| Pos. [°2θ.] | d-spacing [Å] | Rel. Int. [%] |
|---|---|---|
| 6.3 | 14.1 | 9.8 |
| 9.9 | 8.9 | 26.3 |
| 10.5 | 8.4 | 20.0 |
| 12.3 | 7.2 | 51.3 |
| 12.6 | 7.0 | 23.5 |
| 13.6 | 6.5 | 59.4 |
| 14.0 | 6.3 | 13.1 |
| 14.3 | 6.2 | 12.0 |
| 14.9 | 6.0 | 16.7 |
| 16.0 | 5.5 | 14.0 |
| 16.4 | 5.4 | 41.9 |
| 16.9 | 5.2 | 5.3 |
| 17.6 | 5.0 | 43.7 |
| 18.5 | 4.8 | 21.0 |
| 18.9 | 4.7 | 46.2 |
| 19.2 | 4.6 | 8.2 |
| 19.7 | 4.5 | 14.8 |
| 20.8 | 4.3 | 42.4 |
| 21.1 | 4.2 | 26.6 |
| 21.4 | 4.1 | 100.0 |
| 22.3 | 4.0 | 67.4 |
| 23.0 | 3.9 | 18.2 |
| 23.3 | 3.8 | 34.1 |
| 23.5 | 3.8 | 18.7 |
| 24.3 | 3.7 | 47.0 |
| 24.6 | 3.6 | 16.2 |
| 25.3 | 3.5 | 20.4 |
| 26.1 | 3.4 | 8.6 |
| 26.9 | 3.3 | 5.6 |
| 27.5 | 3.2 | 13.8 |
| 28.1 | 3.2 | 6.5 |
| 29.4 | 3.0 | 6.1 |
| 30.8 | 2.9 | 11.1 |
| 31.4 | 2.9 | 5.7 |
| 32.3 | 2.8 | 4.1 |
| 33.1 | 2.7 | 6.2 |
| 33.6 | 2.7 | 1.8 |

One aspect of the present disclosure relates to an mesylate salt of N-(3-(4,6-dimethylpyrimidin-5-yl)-4-(2-(pyrrolidin-1-yl)ethoxy)phenyl)cyclopropanecarboxamide.

One aspect of the present disclosure relates to a mesylate salt having an X-ray powder diffraction pattern comprising a peak, in terms of 2θ, at 6.3°±0.2°, 9.9°±0.2°, 10.5°±0.2°, 12.3°±0.2°, and 12.6°±0.2°. In some embodiments, the mesylate salt has an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9°±0.2°, 15.9°±0.2°, and 16.4°±0.2°.

In some embodiments, the mesylate salt has an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9°±0.2°, 15.9°±0.2°, 16.4°±0.2°, 17.6°±0.2°, 18.5°±0.2°, 18.9°±0.2°, 19.7°±0.2°, 20.8°±0.2°, 21.1°±0.2°, and 21.4°±0.2°. In some embodiments, the mesylate salt has an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9°±0.2°, 15.9°±0.2°, 16.4°±0.2°, 17.6°±0.2°, 18.5°±0.2°, 18.9°±0.2°, 19.7°±0.2°, 20.8°±0.2°, 21.1°±0.2°, 21.4°±0.2°, 22.3°±0.2°, 23.0°±0.2°, 23.3°±0.2°, and 23.5°±0.2°.

In some embodiments, the mesylate salt has an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9°±0.2°, 15.9°±0.2°, 16.4°±0.2°, 17.6°±0.2°, 18.5°±0.2°, 18.9°±0.2°, 19.7°±0.2°, 20.8°±0.2°, 21.1°±0.2°, 21.4°±0.2°, 22.3°±0.2°, 23.0°±0.2°, 23.3°±0.2°, 23.5°±0.2°, 24.3°±0.2°, 24.6°±0.2°, 25.3°±0.2°, and 27.5°±0.2°.

In some embodiments, the mesylate salt has an X-ray powder diffraction pattern substantially as shown in FIG. 16, wherein by "substantially" is meant that the reported peaks can vary by about ±0.2° 2θ.

In some embodiments, the mesylate salt has a differential scanning calorimetry thermogram comprising an endotherm with an extrapolated onset temperature between about 178.4° C. and about 192.7° C.

In some embodiments, the mesylate salt has a differential scanning calorimetry thermogram comprising an endotherm with an extrapolated onset temperature between about 179.4° C. and about 192.7° C.

In some embodiments, the mesylate salt has a differential scanning calorimetry thermogram comprising an endotherm with an extrapolated onset temperature between about 179.4° C. and about 191.7° C.

In some embodiments, the mesylate salt has a differential scanning calorimetry thermogram comprising an endotherm with an extrapolated onset temperature between about 180.4° C. and about 190.7° C.

In some embodiments, the mesylate salt has a differential scanning calorimetry thermogram comprising an endotherm with an extrapolated onset temperature at about 181.4° C.

In some embodiments, the mesylate salt has a differential scanning calorimetry thermogram substantially as shown in FIG. 17, wherein by "substantially" is meant that the reported DSC features can vary by about ±4° C. and that the reported DSC features can vary by about ±20 joules per gram.

In some embodiments, the mesylate salt has a thermogravimetric analysis profile showing about 2.8% weight loss below about 180° C.

In some embodiments, the mesylate salt has a thermogravimetric analysis profile showing about 2.6% weight loss below about 180° C.

In some embodiments, the mesylate salt has a thermogravimetric analysis profile showing about 2.4% weight loss below about 180° C.

In some embodiments, the mesylate salt has a thermogravimetric analysis profile showing about 2.2% weight loss below about 180° C.

In some embodiments, the mesylate salt has a thermogravimetric analysis profile substantially as shown in FIG. 18, wherein by "substantially" is meant that the reported TGA features can vary by about ±5° C., and that that the reported TGA features can vary by about ±2% weight change.

One aspect of the present disclosure relates to the mesylate salt having:

a) an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9°±0.2°, 15.9°±0.2°, and 16.4°±0.2°;

b) a differential scanning calorimetry thermogram comprising an endotherm with an extrapolated onset temperature between about 178.4° C. and about 192.7° C.; and/or c) a thermogravimetric analysis profile showing about 2.8% weight loss below about 180° C.

One aspect of the present disclosure relates to the mesylate salt having:

a) an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9° ±0.2°, 15.9°±0.2°, 16.4°±0.2°, 17.6°±0.2°, 18.5°±0.2°, 18.9°±0.2°, 19.7°±0.2°, 20.8°±0.2°, 21.1°±0.2°, and 21.4°±0.2°;

b) a differential scanning calorimetry thermogram comprising an endotherm with an extrapolated onset temperature between about 179.4° C. and about 192.7° C.; and/or c) a thermogravimetric analysis profile showing about 2.6% weight loss below about 180° C.

One aspect of the present disclosure relates to the mesylate salt having:

a) an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9° ±0.2°, 15.9°±0.2°, 16.4°±0.2°, 17.6°±0.2°, 18.5°±0.2°, 18.9°±0.2°, 19.7°±0.2°, 20.8°±0.2°, 21.1°±0.2°, 21.4°±0.2°, 22.3°±0.2°, 23.0°±0.2°, 23.3°±0.2°, and 23.5°±0.2°;

b) a differential scanning calorimetry thermogram comprising an endotherm with an extrapolated onset temperature between about 179.4° C. and about 191.7° C.; and/or c) a thermogravimetric analysis profile showing about 2.4% weight loss or less below about 180° C.

One aspect of the present disclosure relates to the mesylate salt having:

a) an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9°±0.2°, 15.9°±0.2°, 16.4°±0.2°, 17.6°±0.2°, 18.5°±0.2°, 18.9°±0.2°, 19.7°±0.2°, 20.8°±0.2°, 21.1°±0.2°, 21.4°±0.2°, 22.3°±0.2°, 23.0°±0.2°, 23.3°±0.2°, and 23.5°±0.2°;

b) a differential scanning calorimetry thermogram comprising an endotherm with an extrapolated onset temperature between about 180.4° C. and about 190.7° C.; and/or c) a thermogravimetric analysis profile showing about 2.4% weight loss or less below about 180° C.

One aspect of the present disclosure relates to the mesylate salt having:

a) an X-ray powder diffraction pattern comprising peaks, in terms of 2θ, at 6.3°±0.2°, 9.9°±0.2°, 10.5°±0.2°, 12.3°±0.2°, 12.6°±0.2°, 13.6°±0.2°, 14.0°±0.2°, 14.3°±0.2°, 14.9° ±0.2°, 15.9°±0.2°, 16.4°±0.2°, 17.6°±0.2°, 18.5°±0.2°, 18.9°±0.2°, 19.7°±0.2°, 20.8°±0.2°, 21.1°±0.2°, 21.4°±0.2°, 22.3°±0.2°, 23.0°±0.2°, 23.3°±0.2°, 23.5°±0.2°, 24.3°±0.2°, 24.6°±0.2°, 25.3°±0.2°, and 27.5°±0.2°;

b) a differential scanning calorimetry thermogram comprising an endotherm with an extrapolated onset temperature at about 181.4° C.; and/or c) a thermogravimetric analysis profile showing about 2.2% weight loss or less below about 180° C.

One aspect of the present disclosure relates to the mesylate salt having:

a) an X-ray powder diffraction pattern substantially as shown in FIG. 16;

b) a differential scanning calorimetry thermogram substantially as shown in FIG. 17; and/or c) a thermogravimetric analysis profile substantially as shown in FIG. 18.

7. Compound Ia (Phosphate Salt).

One aspect of the present disclosure relates to phosphate salt of N-(3-(4,6-dimethylpyrimidin-5-yl)-4-(2-(pyrrolidin-1-yl)ethoxy)phenyl)cyclopropanecarboxamide (Compound Ia). The phosphate salt of Compound Ia are characterized by PXRD. The physical properties for the phosphate salt as determined by PXRD are summarized in Table 18 below.

TABLE 18

Figure 19:
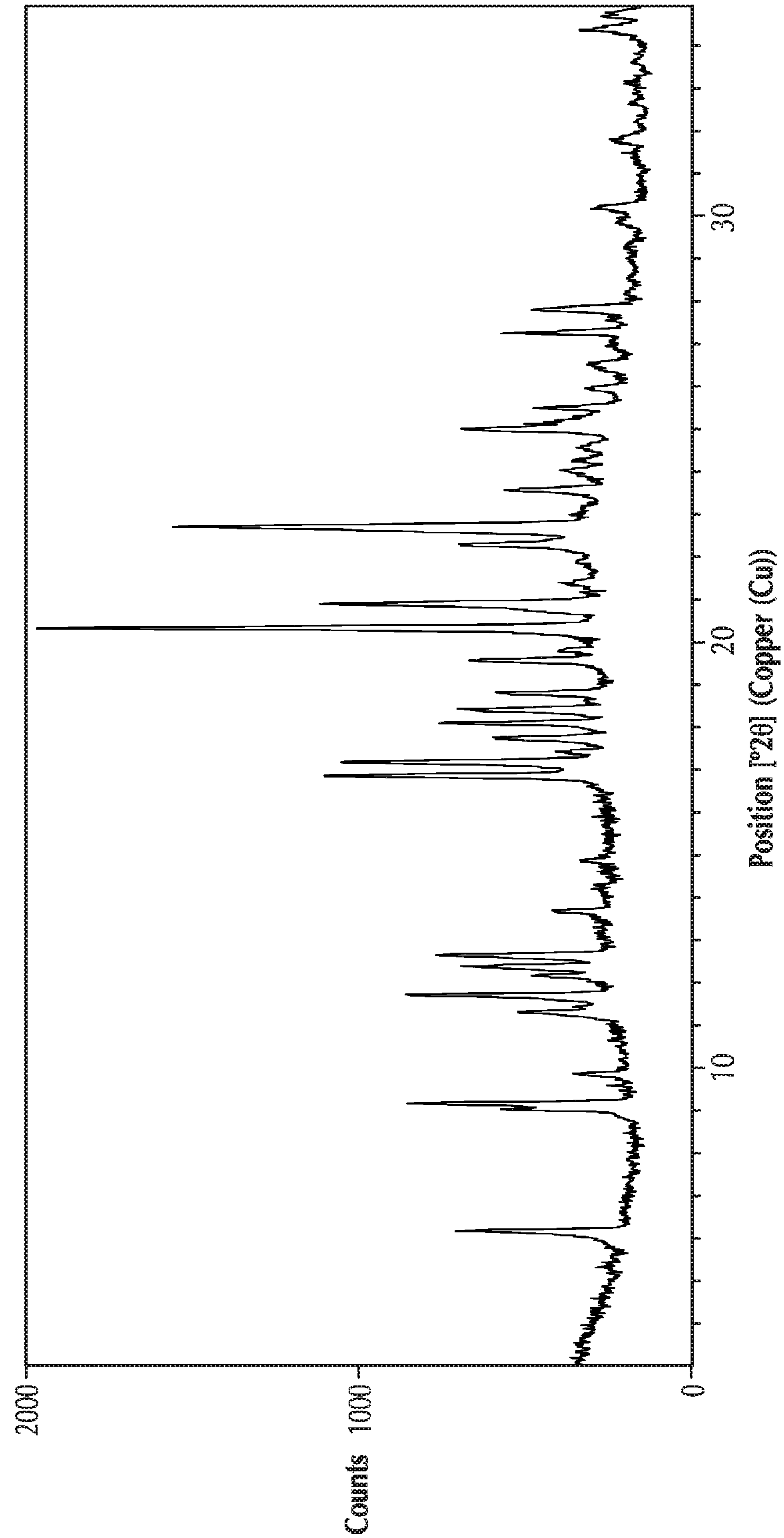
FIG. 19 shows a powder X-ray diffraction (PXRD) pattern for a sample containing a crystalline salt of Compound Ia (Phosphate Salt).

| | Compound Ia (Phosphate Salt, Example 10) |
|---|---|
| PXRD | FIG. 19: Peaks of about ≥11.4% relative intensity at 6.2° ± 0.2°, 9.0° ± 0.2°, 9.2° ± 0.2°, 9.9° ± 0.2°, 11.3° ± 0.2°, 11.7° ± 0.2°, 12.2° ± 0.2°, 12.4° ± 0.2°, 12.7° ± 0.2°, 13.7° ± 0.2°, 16.9° ± 0.2°, 17.2° ± 0.2°, 17.8° ± 0.2°, 18.1° ± 0.2°, 18.5° ± 0.2°, 18.8° ± 0.2°, 19.6° ± 0.2°, 20.3° ± 0.2°, 20.9° ± 0.2°, 22.3° ± 0.2°, 22.7° ± 0.2°, 23.6° ± 0.2°, 25.0° ± 0.2°, 25.5° ± 0.2°, 27.3° ± 0.2°, and 27.8° ± 0.2° °2θ |

The physical properties for a phosphate salt (Example 10) prepared using procedure from Example 10 are summarized in Table 19 below.

TABLE 19

Figure 20:
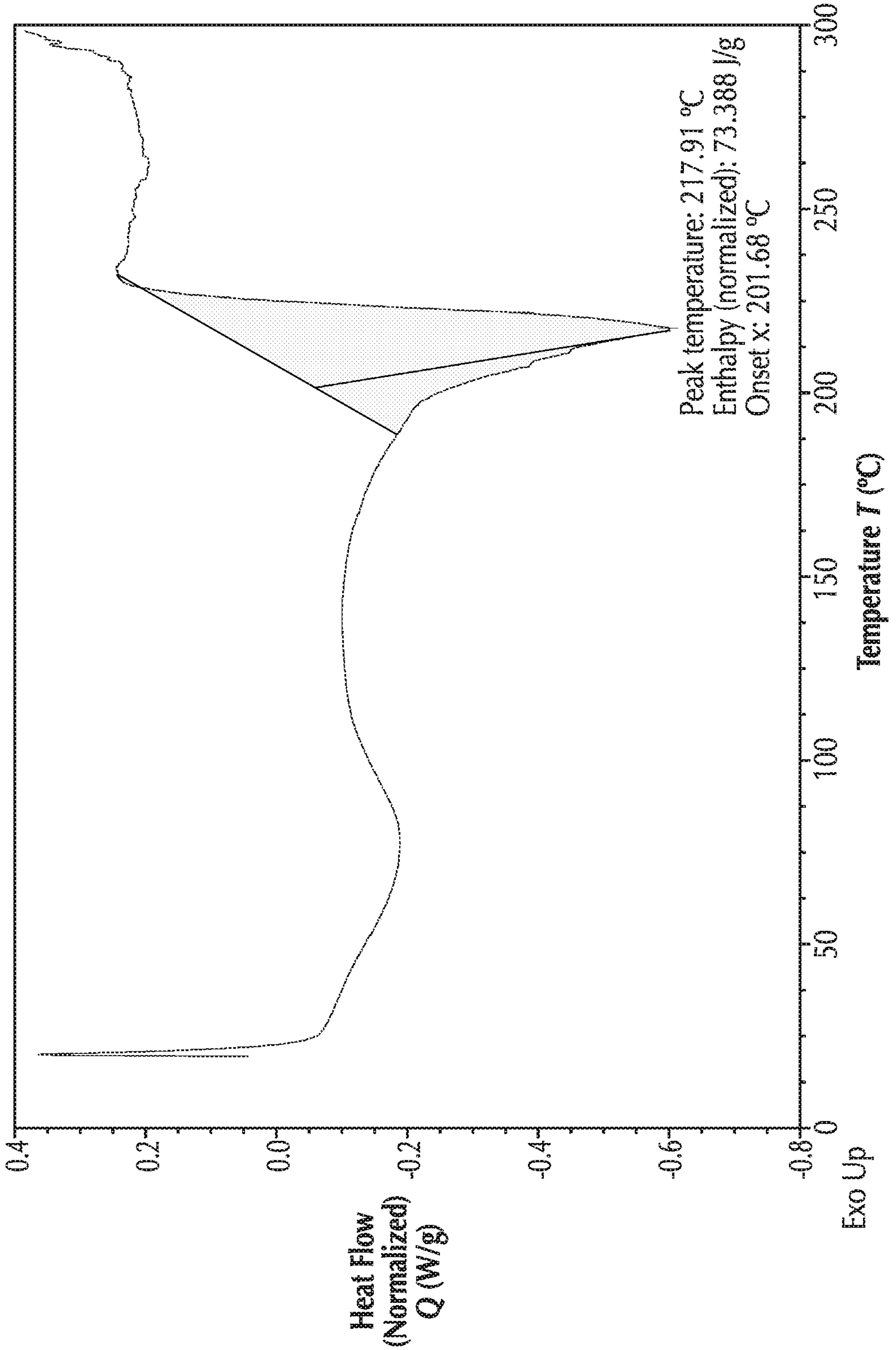
FIG. 20 shows a differential scanning calorimetry (DSC) thermogram for a sample containing a crystalline salt of Compound Ia (Phosphate Salt).
Figure 21:
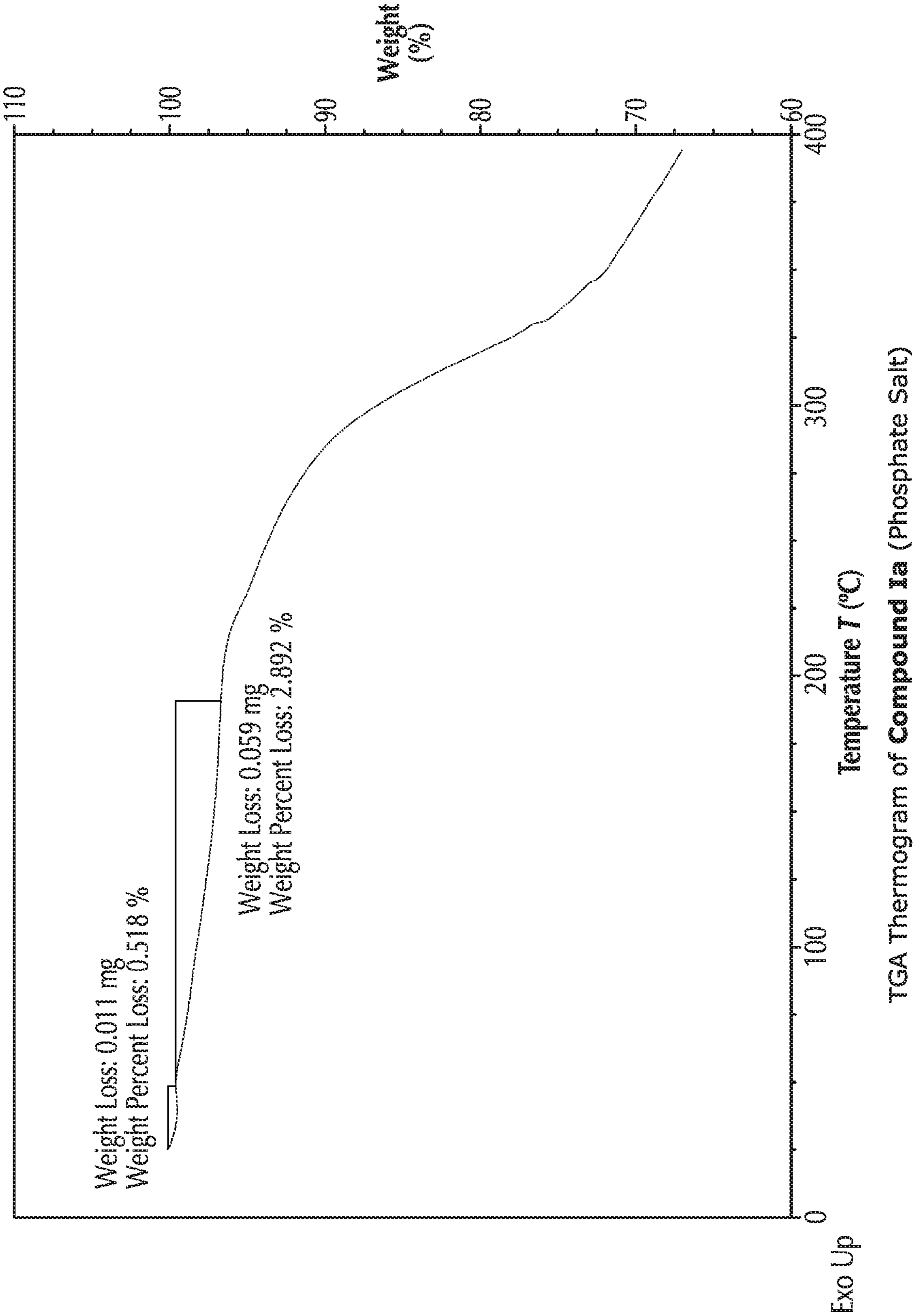
FIG. 21 shows a thermogravimetric analysis (TGA) thermogram of a sample containing a crystalline salt of Compound Ia (Phosphate Salt).

| | Compound Ia (Phosphate Salt, Example 10) |
|---|---|
| TGA | FIG. 21: No observable weight loss below about 212.5° C. |
| DSC | FIG. 20: Endotherms extrapolated onset temperature at about 145° C. and at about 173° C. |

Certain X-ray powder diffraction peaks for the phosphate salt of N-(3-(4,6-dimethylpyrimidin-5-yl)-4-(2-(pyrrolidin-1-yl)ethoxy)phenyl)cyclopropanecarboxamide (Compound Ia) are shown in Table 20 below.

TABLE 20

| Pos. [°2q.] | d-spacing [Å] | Rel. Int. [%] |
|---|---|---|
| 6.2 | 14.3 | 29.8 |
| 9.0 | 9.8 | 23.3 |
| 9.2 | 9.6 | 38.7 |
| 9.9 | 8.9 | 11.4 |
| 11.3 | 7.8 | 20.2 |
| 11.7 | 7.5 | 38.8 |
| 12.2 | 7.3 | 17.6 |
| 12.4 | 7.1 | 26.3 |
| 12.7 | 7.0 | 33.1 |
| 13.7 | 6.5 | 14.8 |
| 14.9 | 6.0 | 10.0 |
| 16.9 | 5.3 | 52.0 |
| 17.2 | 5.2 | 50.0 |
| 17.5 | 5.1 | 13.0 |
| 17.8 | 5.0 | 24.0 |
| 18.1 | 4.9 | 33.6 |
| 18.3 | 4.9 | 9.6 |
| 18.5 | 4.8 | 29.6 |
| 18.8 | 4.7 | 24.4 |
| 19.6 | 4.5 | 26.9 |
| 19.8 | 4.5 | 13.6 |
| 20.3 | 4.4 | 100.0 |
| 20.9 | 4.2 | 51.0 |
| 21.4 | 4.2 | 12.2 |
| 22.3 | 4.0 | 27.9 |
| 22.7 | 3.9 | 78.2 |
| 23.6 | 3.8 | 21.0 |
| 24.1 | 3.7 | 12.5 |
| 24.6 | 3.6 | 9.8 |
| 25.0 | 3.6 | 28.7 |
| 25.5 | 3.5 | 18.5 |
| 26.0 | 3.4 | 8.8 |
| 26.5 | 3.4 | 8.1 |
| 27.3 | 3.3 | 23.1 |
| 27.8 | 3.2 | 18.2 |
| 29.9 | 3.0 | 3.5 |
| 30.2 | 3.0 | 7.0 |
| 31.8 | 2.8 | 3.9 |
| 33.0 | 2.7 | 1.0 |
| 34.4 | 2.6 | 9.4 |
| 34.7 | 2.6 | 6.4 |

One aspect of the present disclosure relates to an phosphate salt of N-(3-(4,6-dimethylpyrimidin-5-yl)-4-(2-(pyrrolidin-1-yl)ethoxy)phenyl)cyclopropanecarboxamide.

One aspect of the present disclosure relates to an phosphate salt having an X-ray powder diffraction pattern comprising a peak, in terms of 2θ, at 6.2°±0.2°, 9.0°±0.2°, 9.2°±0.2°, 9.9° ±0.2° and 11.3°±0.2°. In some embodiments, the phosphate salt has an X-ray powder diffraction pattern comprising peaks, in terms of 2θ, at 6.2°±0.2°, 9.0°±0.2°, 9.2°±0.2°, 9.9°±0.2°, 11.3° ±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, and 18.8°±0.2°.

In some embodiments, the phosphate salt has an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, 18.8°±0.2°, 19.6°±0.2°, 20.3°±0.2°, and 20.9°±0.2°.

In some embodiments, the phosphate salt has an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, 18.8°±0.2°, 19.6°±0.2°, 20.3°±0.2°, 20.9°±0.2°, 22.3°±0.2°, 22.7°±0.2°, and 23.6°±0.2°.

In some embodiments, the phosphate salt has an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8° ±0.2°, 18.1°±0.2°, 18.5°±0.2°, 18.8°±0.2°, 19.6°±0.2°, 20.3°±0.2°, 20.9°±0.2°, 22.3°±0.2°, 22.7°±0.2°, 23.6°±0.2°, 25.0°±0.2°, 25.5°±0.2°, 27.3°±0.2°, and 27.8°±0.2°.

In some embodiments, the phosphate salt has an X-ray powder diffraction pattern substantially as shown in FIG. 19, wherein by "substantially" is meant that the reported peaks can vary by about ±0.2° 2θ.

In some embodiments, the phosphate salt has a differential scanning calorimetry thermogram comprising an endotherm with an extrapolated onset temperature between about 198.7° C. and about 220.9° C.

In some embodiments, the phosphate salt has a differential scanning calorimetry thermogram comprising an endotherm with an extrapolated onset temperature between about 199.7° C. and about 220.9° C.

In some embodiments, the phosphate salt has a differential scanning calorimetry thermogram comprising an endotherm with an extrapolated onset temperature between about 199.7° C. and about 219.9° C.

In some embodiments, the phosphate salt has a differential scanning calorimetry thermogram comprising an endotherm with an extrapolated onset temperature between about 200.7° C. and about 218.9° C.

In some embodiments, the phosphate salt has a differential scanning calorimetry thermogram comprising an endotherm with an extrapolated onset temperature at about 201.7° C.

In some embodiments, the phosphate salt has a differential scanning calorimetry thermogram substantially as shown in FIG. 20, wherein by "substantially" is meant that the reported DSC features can vary by about ±4° C. and that the reported DSC features can vary by about ±20 joules per gram.

In some embodiments, the phosphate salt has a thermogravimetric analysis profile showing about 4.0% weight loss below about 190° C.

In some embodiments, the phosphate salt has a thermogravimetric analysis profile showing about 3.8% weight loss below about 190° C.

In some embodiments, the phosphate salt has a thermogravimetric analysis profile showing about 3.6% weight loss below about 190° C.

In some embodiments, the phosphate salt has a thermogravimetric analysis profile showing about 3.4% weight loss below about 190° C.

In some embodiments, the phosphate salt has a thermogravimetric analysis profile substantially as shown in FIG. 21, wherein by "substantially" is meant that the reported TGA features can vary by about ±5° C., and that that the reported TGA features can vary by about ±2% weight change.

One aspect of the present disclosure relates to the phosphate salt having:

a) an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, and 18.8°±0.2°;

b) a differential scanning calorimetry thermogram comprising an endotherm with an extrapolated onset temperature between about 198.7° C. and about 220.9° C.; and/or c) a thermogravimetric analysis profile showing about 4.0% weight loss below about 190° C.

One aspect of the present disclosure relates to the phosphate salt having:

a) an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, 18.8°±0.2°, 19.6°±0.2°, 20.3°±0.2°, and 20.9°±0.2°;

b) a differential scanning calorimetry thermogram comprising an endotherm with an extrapolated onset temperature between about 199.7° C. and about 220.9° C.; and/or c) a thermogravimetric analysis profile showing about 3.8% weight loss below about 190° C.

One aspect of the present disclosure relates to the phosphate salt having:

a) an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, 18.8°±0.2°, 19.6°±0.2°, 20.3°±0.2°, 20.9°±0.2°, 22.3°±0.2°, 22.7°±0.2°, and 23.6°±0.2°;

b) a differential scanning calorimetry thermogram comprising an endotherm with an extrapolated onset temperature between about 199.7° C. and about 219.9° C.; and/or c) a thermogravimetric analysis profile showing about 3.6% weight loss or less below about 190° C.

One aspect of the present disclosure relates to the phosphate salt having:

a) an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, 18.8°±0.2°, 19.6°±0.2°, 20.3°±0.2°, 20.9°±0.2°, 22.3°±0.2°, 22.7°±0.2°, and 23.6°±0.2°;

b) a differential scanning calorimetry thermogram comprising an endotherm with an extrapolated onset temperature between about 200.7° C. and about 218.9° C.; and/or c) a thermogravimetric analysis profile showing about 3.6% weight loss or less below about 190° C.

One aspect of the present disclosure relates to the phosphate salt having:

a) an X-ray powder diffraction pattern comprising peaks, in terms of 2θ, at 6.2°±0.2°, 9.0°±0.2°, 9.2°±0.2°, 9.9°±0.2°, 11.3°±0.2°, 11.7°±0.2°, 12.2°±0.2°, 12.4°±0.2°, 12.7°±0.2°, 13.7°±0.2°, 16.9°±0.2°, 17.2°±0.2°, 17.8°±0.2°, 18.1°±0.2°, 18.5°±0.2°, 18.8°±0.2°, 19.6°±0.2°, 20.3°±0.2°, 20.9°±0.2°, 22.3°±0.2°, 22.7°±0.2°, 23.6°±0.2°, 25.0°±0.2°, 25.5°±0.2°, 27.3°±0.2°, and 27.8°±0.2°;

b) a differential scanning calorimetry thermogram comprising an endotherm with an extrapolated onset temperature at about 201.7° C.; and/or c) a thermogravimetric analysis profile showing about 3.4% weight loss or less below about 190° C.

One aspect of the present disclosure relates to the phosphate salt having:

a) an X-ray powder diffraction pattern substantially as shown in FIG. 19;

b) a differential scanning calorimetry thermogram substantially as shown in FIG. 20; and/or c) a thermogravimetric analysis profile substantially as shown in FIG. 21.

8. Compound Ia (Succinate Salt).

One aspect of the present disclosure relates to a succinate salt of N-(3-(4,6-dimethylpyrimidin-5-yl)-4-(2-(pyrrolidin-1-yl)ethoxy)phenyl)cyclopropanecarboxamide (Compound Ia). The succinate salt of Compound Ia are characterized by PXRD. The physical properties for the succinate salt as determined by PXRD are summarized in Table 21 below.

TABLE 21

Figure 22:
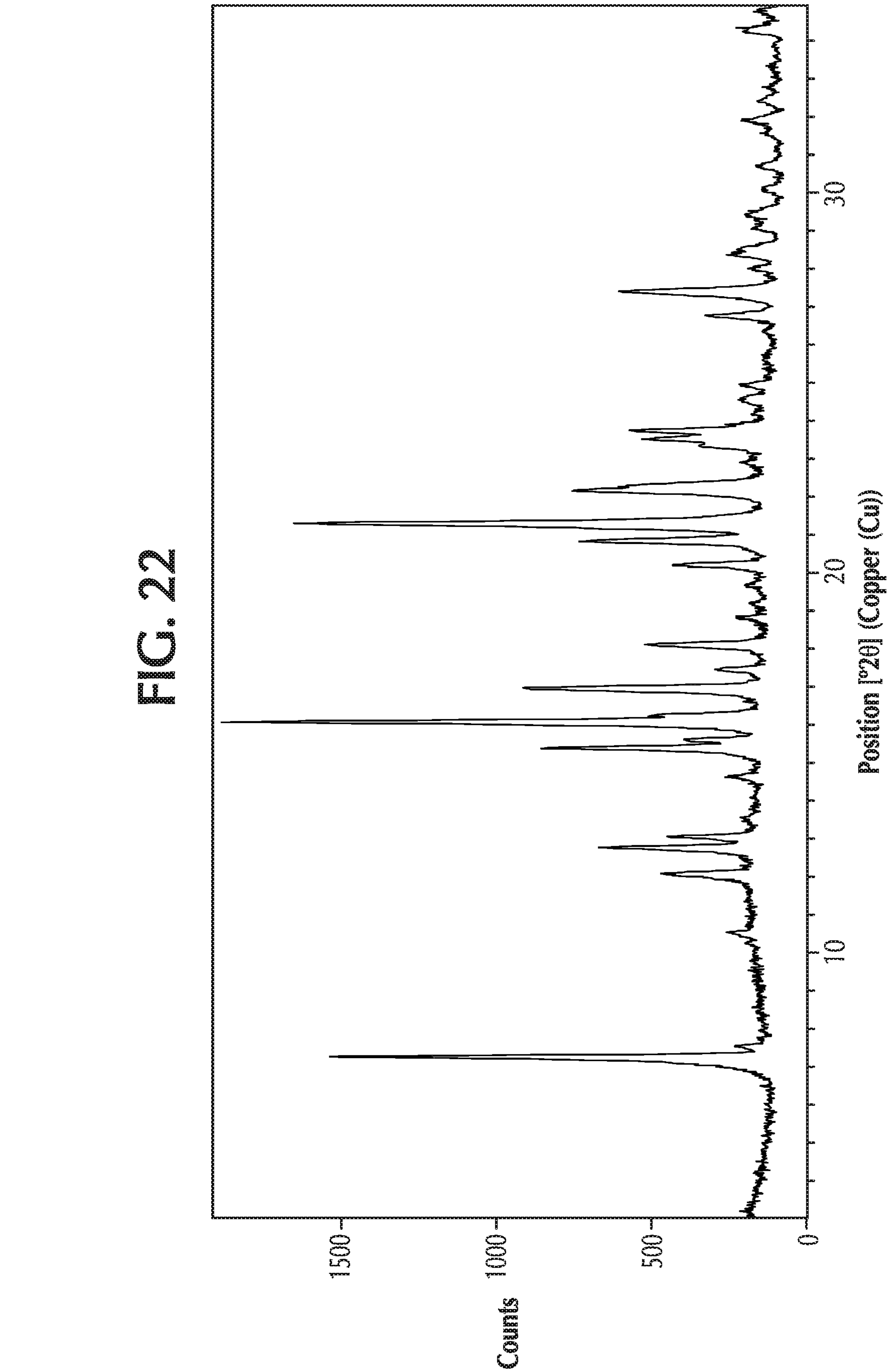
FIG. 22 shows a powder X-ray diffraction (PXRD) pattern for a sample containing a crystalline salt of Compound Ia (Succinate Salt).

| | Compound Ia (Succinate Salt, Example 11) |
|---|---|
| PXRD | FIG. 22: Peaks of about ≥9.5% relative intensity at 7.3° ± 0.2°, 12.1° ± 0.2°, 12.8° ± 0.2°, 13.1° ± 0.2°, 15.4° ± 0.2°, 15.6° ± 0.2°, 16.1° ± 0.2°, 17.0° ± 0.2°, 17.5° ± 0.2°, 18.2° ± 0.2°, 20.2° ± 0.2°, 20.9° ± 0.2°, 21.4° ± 0.2°, 22.2° ± 0.2°, 22.4° ± 0.2°, 23.4° ± 0.2°, 23.5° ± 0.2°, 23.8° ± 0.2°, 26.8° ± 0.2°, and 27.4° ± 0.2° °2θ |

The physical properties for a succinate salt (Example 11) prepared using procedure from Example 11 are summarized in Table 22 below.

TABLE 22

Figure 23:
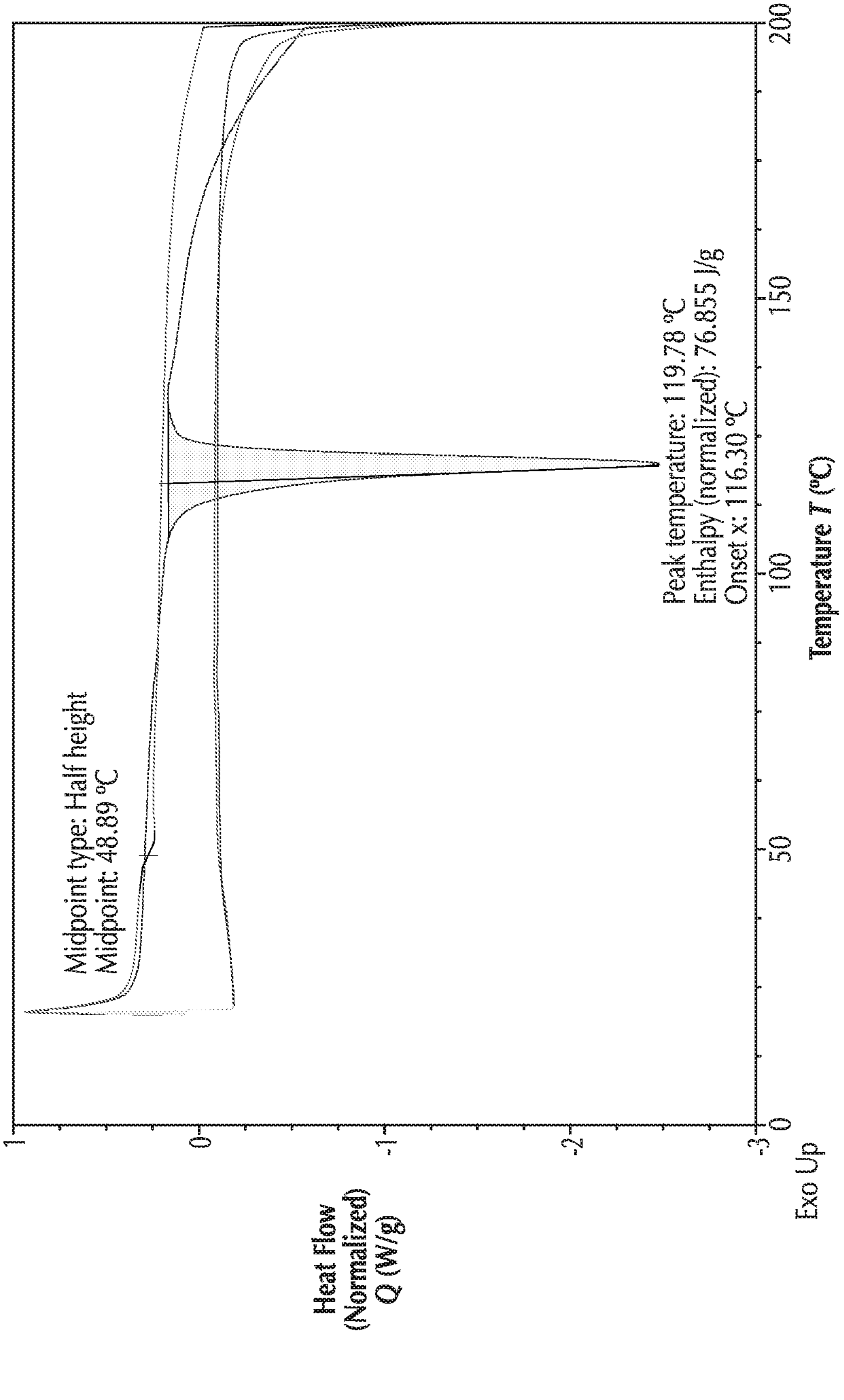
FIG. 23 shows a differential scanning calorimetry (DSC) thermogram for a sample containing a crystalline salt of Compound Ia (Succinate Salt).
Figure 24:
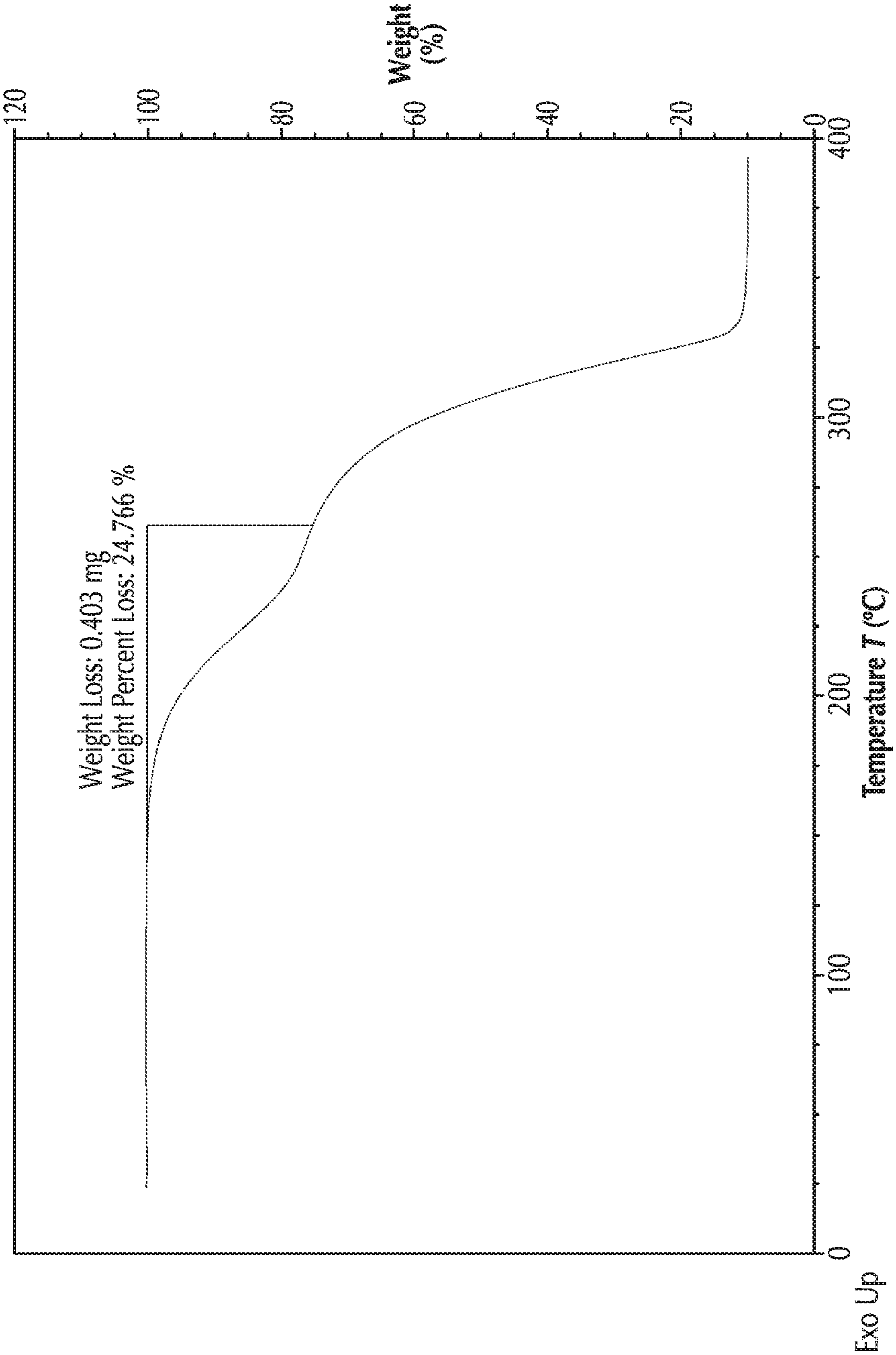
FIG. 24 shows a thermogravimetric analysis (TGA) thermogram of a sample containing a crystalline salt of Compound Ia (Succinate Salt).

| | Compound Ia (Succinate Salt, Example 11) |
|---|---|
| TGA | FIG. 24: Decrease in weight of about 24.8% out to about 2750° C. |
| DSC | FIG. 23: Endotherm extrapolated onset temperature at about 116.3° C. |

Certain X-ray powder diffraction peaks for the succinate salt of N-(3-(4,6-dimethylpyrimidin-5-yl)-4-(2-(pyrrolidin-1-yl)ethoxy)phenyl)cyclopropanecarboxamide (Compound Ia) are shown in Table 23 below.

TABLE 23

| Pos. [°2q.] | d-spacing [Å] | Rel. Int. [%] |
|---|---|---|
| 7.3 | 12.1 | 79.9 |
| 7.6 | 11.7 | 6.3 |
| 10.5 | 8.4 | 5.9 |
| 12.1 | 7.3 | 19.3 |
| 12.8 | 6.9 | 30.4 |
| 13.1 | 6.8 | 18.1 |
| 13.5 | 6.5 | 3.8 |
| 14.7 | 6.0 | 7.1 |
| 15.4 | 5.7 | 41.3 |
| 15.6 | 5.7 | 15.9 |
| 16.1 | 5.5 | 100.0 |
| 17.0 | 5.2 | 45.3 |
| 17.5 | 5.1 | 9.5 |
| 18.2 | 4.9 | 21.7 |
| 18.9 | 4.7 | 6.1 |
| 19.3 | 4.6 | 2.4 |
| 19.7 | 4.5 | 4.6 |
| 20.2 | 4.4 | 18.2 |
| 20.9 | 4.3 | 33.6 |
| 21.4 | 4.2 | 81.8 |
| 22.2 | 4.0 | 36.6 |
| 22.4 | 4.0 | 22.7 |
| 22.9 | 3.9 | 4.0 |
| 23.4 | 3.8 | 13.1 |
| 23.5 | 3.8 | 22.7 |
| 23.8 | 3.7 | 23.9 |
| 24.7 | 3.6 | 5.3 |
| 25.0 | 3.6 | 6.1 |
| 26.8 | 3.3 | 12.6 |
| 27.4 | 3.3 | 28.3 |
| 28.0 | 3.2 | 4.0 |
| 28.4 | 3.1 | 8.3 |
| 28.5 | 3.1 | 6.4 |
| 29.1 | 3.1 | 3.4 |
| 29.5 | 3.0 | 4.9 |
| 30.1 | 3.0 | 2.3 |
| 30.7 | 2.9 | 3.1 |
| 31.9 | 2.8 | 5.9 |
| 32.4 | 2.8 | 3.1 |
| 34.3 | 2.6 | 5.6 |

One aspect of the present disclosure relates to a succinate salt of N-(3-(4,6-dimethylpyrimidin-5-yl)-4-(2-(pyrrolidin-1-yl)ethoxy)phenyl)cyclopropanecarboxamide.

One aspect of the present disclosure relates to a succinate salt having an X-ray powder diffraction pattern comprising a peak, in terms of 2θ, at 7.3°±0.2°, 12.1°±0.2°, 12.8°±0.2°, and 13.1°±0.2°. In some embodiments, the succinate salt has an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, and 17.5°±0.2°.

In some embodiments, the succinate salt has an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, 17.5°±0.2°, 18.2°±0.2°, 20.2°±0.2°, 20.9°±0.2°, and 21.4°±0.2°.

In some embodiments, the succinate salt has an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, 17.5°±0.2°, 18.2°±0.2°, 20.2°±0.2°, 20.9°±0.2°, 21.4°±0.2°, 22.2°±0.2°, 22.4°±0.2°, 23.4°±0.2°, and 23.5°±0.2°.

In some embodiments, the succinate salt has an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, 17.5°±0.2°, 18.2°±0.2°, 20.2°±0.2°, 20.9°±0.2°, 21.4°±0.2°, 22.2°±0.2°, 22.4°±0.2°, 23.4°±0.2°, 23.5°±0.2°, 23.8°±0.2°, 26.8°±0.2°, and 27.4°±0.2°.

In some embodiments, the succinate salt has an X-ray powder diffraction pattern substantially as shown in FIG. 22, wherein by "substantially" is meant that the reported peaks can vary by about ±0.2° 2θ.

In some embodiments, the succinate salt has a differential scanning calorimetry thermogram comprising an endotherm with an extrapolated onset temperature between about 113.3° C. and about 122.8° C.

In some embodiments, the succinate salt has a differential scanning calorimetry thermogram comprising an endotherm with an extrapolated onset temperature between about 114.3° C. and about 122.8° C.

In some embodiments, the succinate salt has a differential scanning calorimetry thermogram comprising an endotherm with an extrapolated onset temperature between about 114.3° C. and about 121.8° C.

In some embodiments, the succinate salt has a differential scanning calorimetry thermogram comprising an endotherm with an extrapolated onset temperature between about 115.3° C. and about 120.8° C.

In some embodiments, the succinate salt has a differential scanning calorimetry thermogram comprising an endotherm with an extrapolated onset temperature at about 116.3° C. In some embodiments, the succinate salt has a differential scanning calorimetry thermogram substantially as shown in FIG. 23, wherein by "substantially" is meant that the reported DSC features can vary by about ±4° C. and that the reported DSC features can vary by about ±20 joules per gram.

In some embodiments, the succinate salt has a thermogravimetric analysis profile showing about 25.4% weight loss below about 275° C.

In some embodiments, the succinate salt has a thermogravimetric analysis profile showing about 25.2% weight loss below about 275° C.

In some embodiments, the succinate salt has a thermogravimetric analysis profile showing about 25.0% weight loss or less below about 275° C.

In some embodiments, the succinate salt has a thermogravimetric analysis profile showing about 24.8% weight loss or less below about 275° C.

In some embodiments, the succinate salt has a thermogravimetric analysis profile substantially as shown in FIG. 24, wherein by "substantially" is meant that the reported TGA features can vary by about ±5° C., and that that the reported TGA features can vary by about ±2% weight change.

One aspect of the present disclosure relates to the succinate salt having:

a) an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, and 17.5°±0.2°;

b) a differential scanning calorimetry thermogram comprising an endotherm with an extrapolated onset temperature between about 113.3° C. and about 122.8° C.; and/or c) a thermogravimetric analysis profile showing about 25.4% weight loss below about 275° C.

One aspect of the present disclosure relates to the succinate salt having:

a) an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, 17.5°±0.2°, 18.2°±0.2°, 20.2°±0.2°, 20.9°±0.2°, and 21.4°±0.2°;

b) a differential scanning calorimetry thermogram comprising an endotherm with an extrapolated onset temperature between about 114.3° C. and about 122.8° C.; and/or c) a thermogravimetric analysis profile showing about 25.2% weight loss below about 275° C.

One aspect of the present disclosure relates to the succinate salt having:

a) an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, 17.5°±0.2°, 18.2°±0.2°, 20.2°±0.2°, 20.9°±0.2°, 21.4°±0.2°, 22.2°±0.2°, 22.4°±0.2°, 23.4°±0.2°, and 23.5°±0.2°;

b) a differential scanning calorimetry thermogram comprising an endotherm with an extrapolated onset temperature between about 114.3° C. and about 121.8° C.; and/or c) a thermogravimetric analysis profile showing about 25.0% weight loss or less below about 275° C.

One aspect of the present disclosure relates to the succinate salt having:

a) an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, 17.5°±0.2°, 18.2°±0.2°, 20.2°±0.2°, 20.9°±0.2°, 21.4°±0.2°, 22.2°±0.2°, 22.4°±0.2°, 23.4°±0.2°, and 23.5°±0.2°;

b) a differential scanning calorimetry thermogram comprising an endotherm with an extrapolated onset temperature between about 115.3° C. and about 120.8° C.; and/or c) a thermogravimetric analysis profile showing about 25.0% weight loss or less below about 275° C.

One aspect of the present disclosure relates to the succinate salt having:

a) an X-ray powder diffraction pattern comprising peaks, in terms of 2θ, at 7.3°±0.2°, 12.1°±0.2°, 12.8°±0.2°, 13.1°±0.2°, 15.4°±0.2°, 15.6°±0.2°, 16.1°±0.2°, 17.0°±0.2°, 17.5° ±0.2°, 18.2°±0.2°, 20.2°±0.2°, 20.9°±0.2°, 21.4°±0.2°, 22.2°±0.2°, 22.4°±0.2°, 23.4°±0.2°, 23.5°±0.2°, 23.8°±0.2°, 26.8°±0.2°, and 27.4°±0.2°;

b) a differential scanning calorimetry thermogram comprising an endotherm with an extrapolated onset temperature at about 116.3° C.; and/or c) a thermogravimetric analysis profile showing about 24.8% weight loss or less below about 275° C.

One aspect of the present disclosure relates to the succinate salt having:

a) an X-ray powder diffraction pattern substantially as shown in FIG. 22;

b) a differential scanning calorimetry thermogram substantially as shown in FIG. 23; and/or c) a thermogravimetric analysis profile substantially as shown in FIG. 24.

9. Compound Ia (Tosylate Salt).

One aspect of the present disclosure relates to a tosylate salt of N-(3-(4,6-dimethylpyrimidin-5-yl)-4-(2-(pyrrolidin-1-yl)ethoxy)phenyl)cyclopropanecarboxamide (Compound Ia). The tosylate salt of Compound Ia are characterized by PXRD. The physical properties for the tosylate salt as determined by PXRD are summarized in Table 30 below.

TABLE 30

Figure 25:
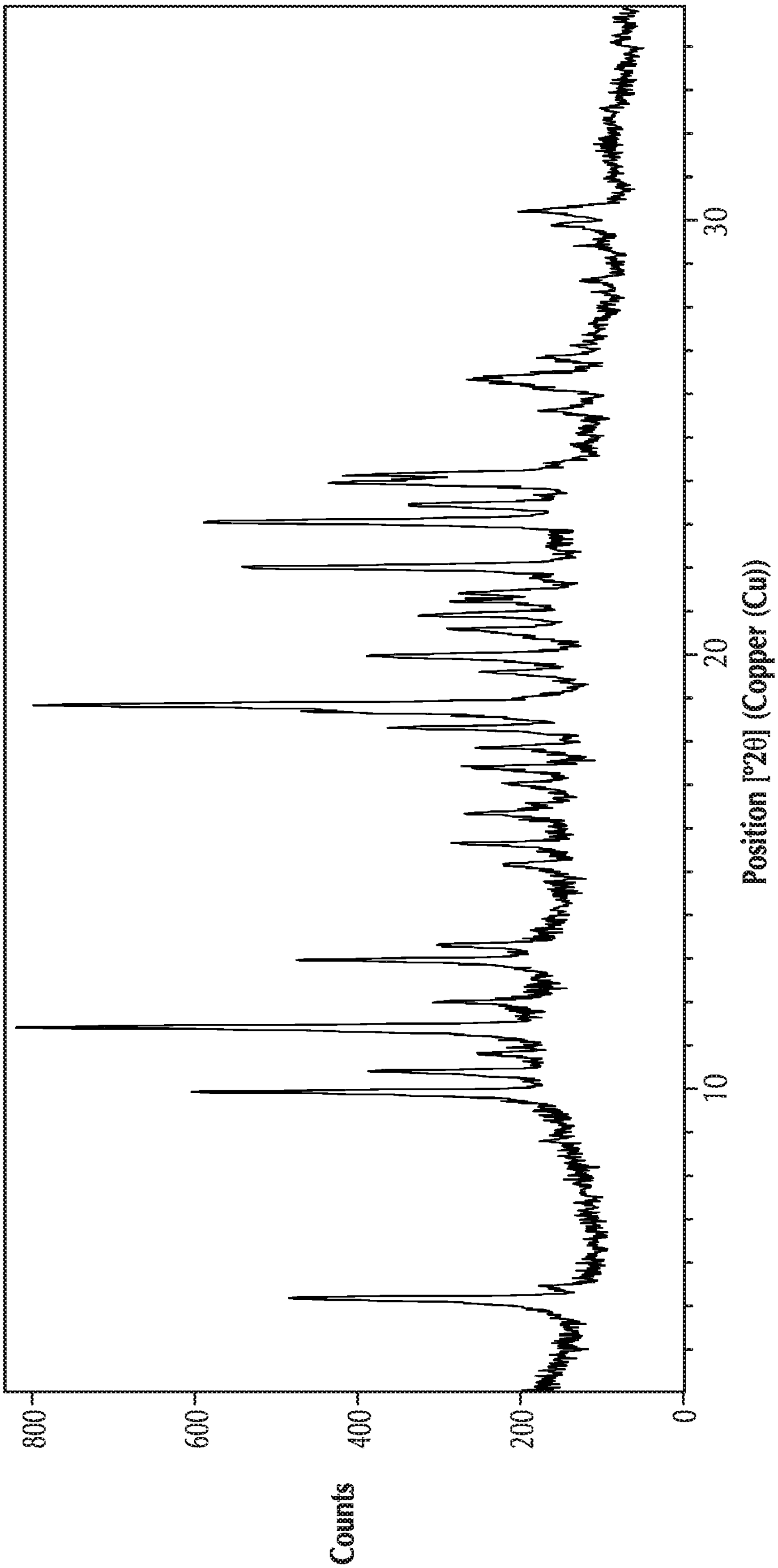
FIG. 25 shows a powder X-ray diffraction (PXRD) pattern for a sample containing a crystalline salt of Compound Ia (Tosylate Salt).

| Compound Ia (Tosylate Salt, Example 12) | |
|---|---|
| PXRD | FIG. 25: Peaks of about ≥17.9% relative intensity at 5.2° ± 0.2°, 10.0° ± 0.2°, 10.4° ± 0.2°, 12.0° ± 0.2°, 13.0° ± 0.2°, 13.4° ± 0.2°, 15.7° ± 0.2°, 16.4° ± 0.2°, 17.4° ± 0.2°, 17.9° ± 0.2°, 18.4° ± 0.2°, 18.9° ± 0.2°, 19.6° ± 0.2°, 20.0° ± 0.2°, 20.6° ± 0.2°, 20.9° ± 0.2°, 21.3° ± 0.2°, 21.5° ± 0.2°, 22.08° ± 0.2°, 23.1° ± 0.2°, 23.5° ± 0.2°, 24.0° ± 0.2°, 24.2° ± 0.2°, and 26.4° ± 0.2° °2θ |

The physical properties for a tosylate salt (Example 12) prepared using procedure from Example 12, Method 2, are summarized in Table 31 below.

TABLE 31

Figure 26:
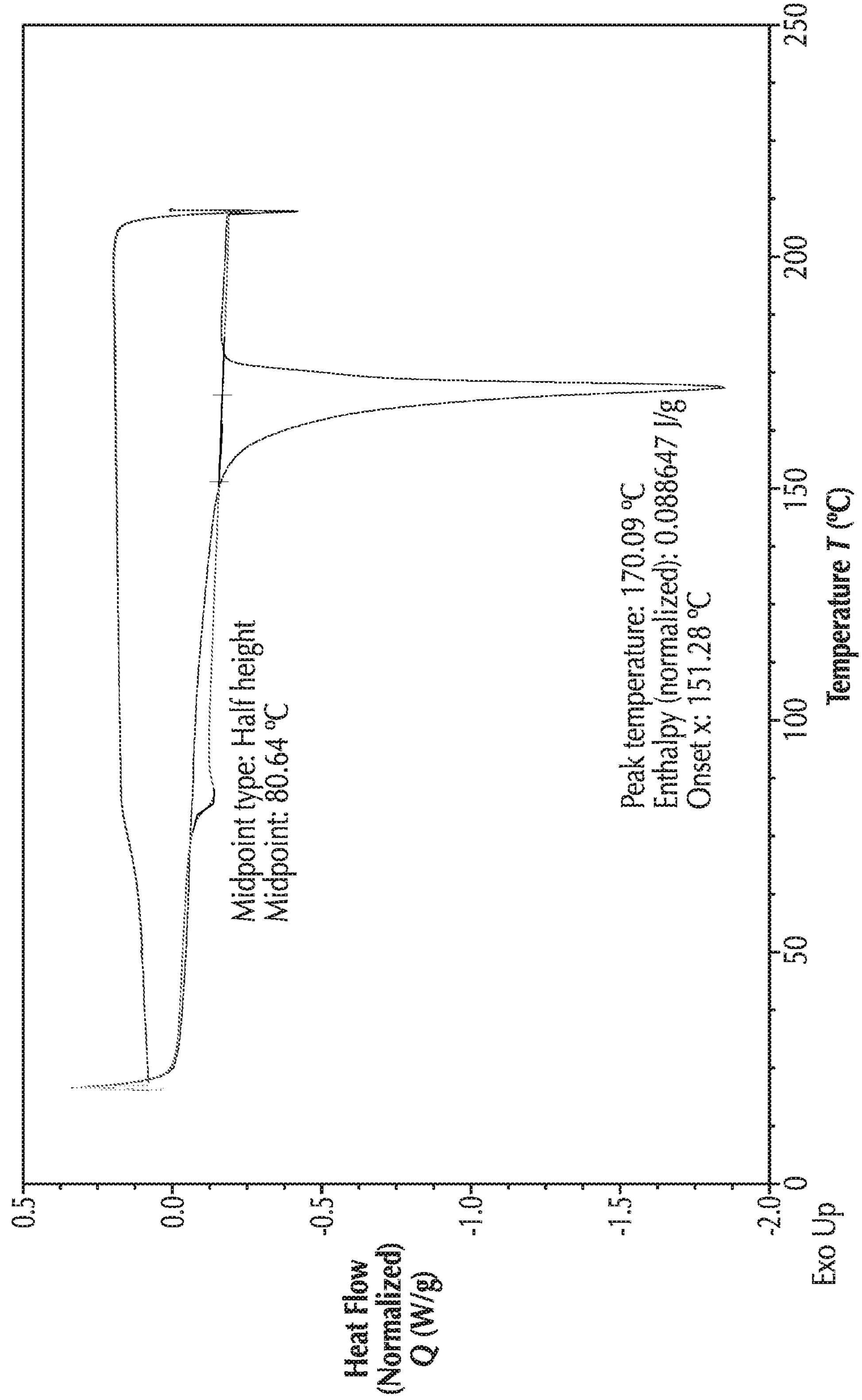
FIG. 26 shows a differential scanning calorimetry (DSC) thermogram for a sample containing a crystalline salt of Compound Ia (Tosylate Salt).
Figure 27:
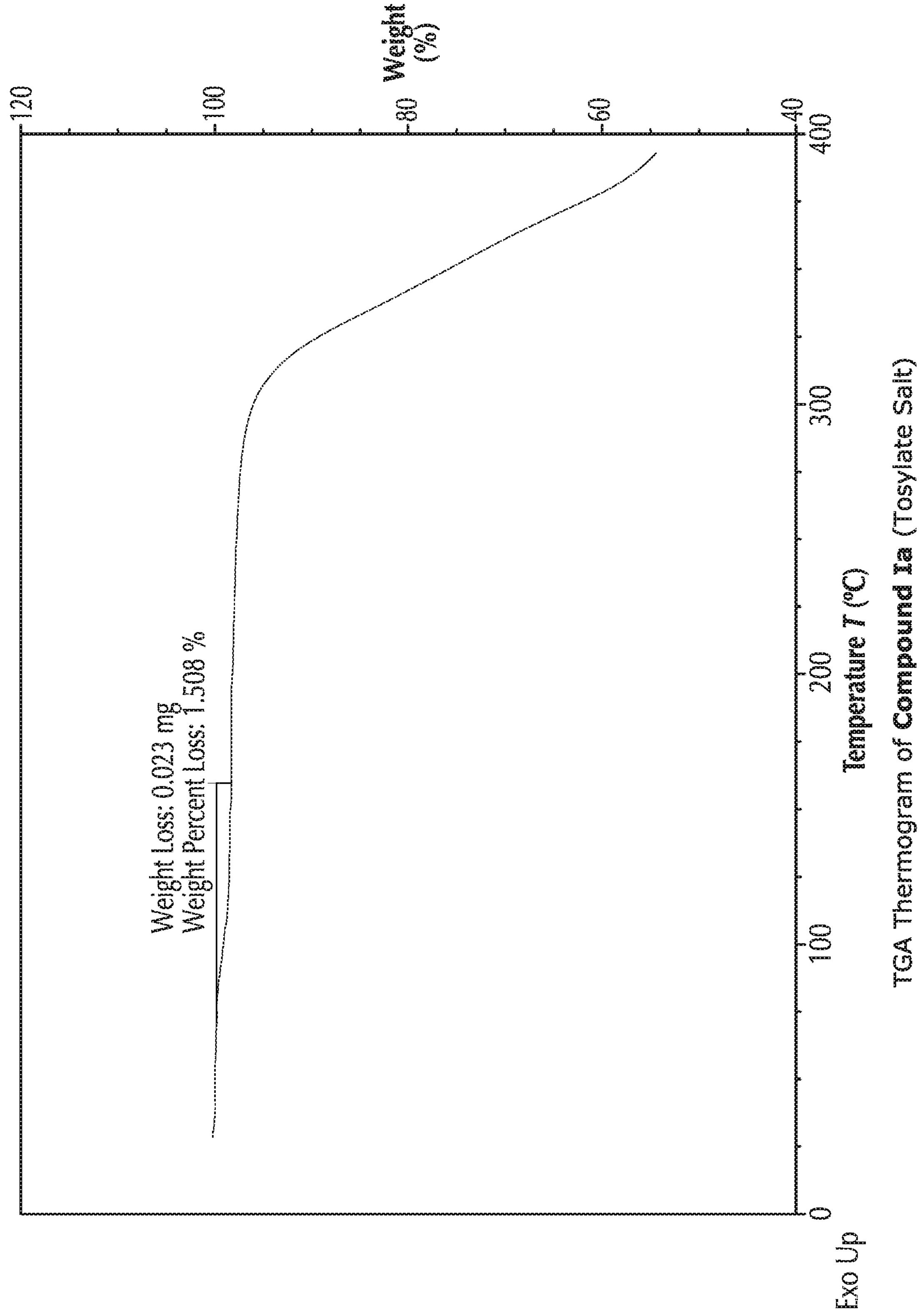
FIG. 27 shows a thermogravimetric analysis (TGA) thermogram of a sample containing a crystalline salt of Compound Ia (Tosylate Salt).

| Compound 1 (Tosylate Salt, Example 12) | |
|---|---|
| TGA | FIG. 27: Decrease in weight of about 1.5% out to about 180° C. |
| DSC | FIG. 26: Endotherm extrapolated onset temperature at about 151.3° C. |

Certain X-ray powder diffraction peaks for the tosylate salt of N-(3-(4,6-dimethylpyrimidin-5-yl)-4-(2-(pyrrolidin-1-yl)ethoxy)phenyl)cyclopropanecarboxamide (Compound Ia) are shown in Table 32 below.

TABLE 32

| Pos. [°2q.] | d-spacing [Å] | Rel. Int. [%] |
|---|---|---|
| 5.2 | 16.9 | 51.4 |
| 10.0 | 8.9 | 67.6 |
| 10.4 | 8.5 | 36.3 |
| 10.8 | 8.2 | 15.7 |
| 11.4 | 7.7 | 100.0 |
| 12.0 | 7.4 | 25.0 |
| 13.0 | 6.8 | 50.3 |
| 13.4 | 6.6 | 25.1 |
| 15.2 | 5.8 | 13.9 |
| 15.7 | 5.7 | 22.0 |
| 16.4 | 5.4 | 21.2 |
| 17.1 | 5.2 | 14.5 |
| 17.4 | 5.1 | 19.0 |
| 17.9 | 5.0 | 17.9 |
| 18.4 | 4.8 | 33.4 |
| 18.9 | 4.7 | 99.4 |
| 19.6 | 4.5 | 19.7 |
| 20.0 | 4.4 | 40.6 |
| 20.6 | 4.3 | 26.1 |
| 20.9 | 4.2 | 30.7 |
| 21.3 | 4.2 | 24.5 |
| 21.5 | 4.1 | 23.6 |
| 22.0 | 4.0 | 63.7 |
| 23.1 | 3.9 | 70.7 |
| 23.5 | 3.8 | 31.1 |
| 24.0 | 3.7 | 48.7 |
| 24.2 | 3.7 | 39.9 |
| 25.6 | 3.5 | 9.8 |
| 26.4 | 3.4 | 20.7 |
| 26.9 | 3.3 | 11.4 |
| 28.7 | 3.1 | 4.3 |
| 29.9 | 3.0 | 10.2 |
| 30.3 | 3.0 | 16.5 |

One aspect of the present disclosure relates to a tosylate salt of N-(3-(4,6-dimethylpyrimidin-5-yl)-4-(2-(pyrrolidin-1-yl)ethoxy)phenyl)cyclopropanecarboxamide.

One aspect of the present disclosure relates to a tosylate salt having an X-ray powder diffraction pattern comprising a peak, in terms of 2θ, at 5.2°±0.2°, 10.0°±0.2°, 10.4°±0.2°, 12.0°±0.2°, and 13.0°±0.2°. In some embodiments, the tosylate salt has an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, and 18.9°±0.2°.

In some embodiments, the tosylate salt has an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, 18.9°±0.2°, 19.6°±0.2°, 20.0°±0.2°, 20.6°±0.2°, and 20.9°±0.2°.

In some embodiments, the tosylate salt has an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, 18.9°±0.2°, 19.6°±0.2°, 20.0°±0.2°, 20.6°±0.2°, 20.9°±0.2°, 21.3°±0.2°, 21.5°±0.2°, 22.08°±0.2°, and 23.1°±0.2°.

In some embodiments, the tosylate salt has an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, 18.9°±0.2°, 19.6°±0.2°, 20.0°±0.2°, 20.6°±0.2°, 20.9°±0.2°, 21.3°±0.2°, 21.5°±0.2°, 22.08°±0.2°, 23.1°±0.2°, 23.5°±0.2°, 24.0°±0.2°, 24.2°±0.2°, and 26.4°±0.2°.

In some embodiments, the tosylate salt has an X-ray powder diffraction pattern substantially as shown in FIG. 25, wherein by "substantially" is meant that the reported peaks can vary by about ±0.2° 2θ.

In some embodiments, the tosylate salt has a differential scanning calorimetry thermogram comprising an endotherm with an extrapolated onset temperature between about 148.3° C. and about 173.1° C.

In some embodiments, the tosylate salt has a differential scanning calorimetry thermogram comprising an endotherm with an extrapolated onset temperature between about 149.3° C. and about 173.1° C.

In some embodiments, the tosylate salt has a differential scanning calorimetry thermogram comprising an endotherm with an extrapolated onset temperature between about 149.3° C. and about 172.1° C.

In some embodiments, the tosylate salt has a differential scanning calorimetry thermogram comprising an endotherm with an extrapolated onset temperature between about 150.3° C. and about 171.1° C.

In some embodiments, the tosylate salt has a differential scanning calorimetry thermogram comprising an endotherm with an extrapolated onset temperature at about 151.3° C. In some embodiments, the tosylate salt has a differential scanning calorimetry thermogram substantially as shown in FIG. 26, wherein by "substantially" is meant that the reported DSC features can vary by about ±4° C. and that the reported DSC features can vary by about ±20 joules per gram.

In some embodiments, the tosylate salt has a thermogravimetric analysis profile showing about 2.1% weight loss below about 180° C.

In some embodiments, the tosylate salt has a thermogravimetric analysis profile showing about 1.9% weight loss below about 180° C.

In some embodiments, the tosylate salt has a thermogravimetric analysis profile showing about 1.7% weight loss below about 180° C.

In some embodiments, the tosylate salt has a thermogravimetric analysis profile showing about 1.5% weight loss below about 180° C.

In some embodiments, the tosylate salt has a thermogravimetric analysis profile substantially as shown in FIG. 27, wherein by "substantially" is meant that the reported TGA features can vary by about ±5° C., and that that the reported TGA features can vary by about ±2% weight change.

One aspect of the present disclosure relates to the tosylate salt having:

a) an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, and 18.9°±0.2°;

b) a differential scanning calorimetry thermogram comprising an endotherm with an extrapolated onset temperature between about 148.3° C. and about 173.1° C.; and/or c) a thermogravimetric analysis profile showing about 2.1% weight loss below about 180° C.

One aspect of the present disclosure relates to the tosylate salt having:

a) an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, 18.9°±0.2°, 19.6°±0.2°, 20.0°±0.2°, 20.6°±0.2°, and 20.9°±0.2°;

b) a differential scanning calorimetry thermogram comprising an endotherm with an extrapolated onset temperature between about 149.3° C. and about 173.1° C.; and/or c) a thermogravimetric analysis profile showing about 1.9% weight loss below about 180° C.

One aspect of the present disclosure relates to the tosylate salt having:

a) an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, 18.9°±0.2°, 19.6°±0.2°, 20.0°±0.2°, 20.6°±0.2°, 20.9°±0.2°, 21.3°±0.2°, 21.5°±0.2°, 22.08°±0.2°, and 23.1°±0.2°;

b) a differential scanning calorimetry thermogram comprising an endotherm with an extrapolated onset temperature between about 149.3° C. and about 172.1° C.; and/or c) a thermogravimetric analysis profile showing about 1.7% weight loss or less below about 180° C.

One aspect of the present disclosure relates to the tosylate salt having:

a) an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4°±0.2°, 17.9°±0.2°, 18.4°±0.2°, 18.9°±0.2°, 19.6°±0.2°, 20.0°±0.2°, 20.6°±0.2°, 20.9°±0.2°, 21.3°±0.2°, 21.5°±0.2°, 22.08°±0.2°, and 23.1°±0.2°;

b) a differential scanning calorimetry thermogram comprising an endotherm with an extrapolated onset temperature between about 150.3° C. and about 171.1° C.; and/or c) a thermogravimetric analysis profile showing about 1.7% weight loss or less below about 180° C.

One aspect of the present disclosure relates to the tosylate salt having:

a) an X-ray powder diffraction pattern comprising peaks, in terms of 2θ, at 5.2°±0.2°, 10.0°±0.2°, 10.4°±0.2°, 12.0°±0.2°, 13.0°±0.2°, 13.4°±0.2°, 15.7°±0.2°, 16.4°±0.2°, 17.4° ±0.2°, 17.9°±0.2°, 18.4°±0.2°, 18.9°±0.2°, 19.6°±0.2°, 20.0°±0.2°, 20.6°±0.2°, 20.9°±0.2°, 21.3°±0.2°, 21.5°±0.2°, 22.08°±0.2°, 23.1°±0.2°, 23.5°±0.2°, 24.0°±0.2°, 24.2°±0.2°, and 26.4°±0.2°;

b) a differential scanning calorimetry thermogram comprising an endotherm with an extrapolated onset temperature at about 151.3° C.; and/or c) a thermogravimetric analysis profile showing about 1.5% weight loss or less below about 180° C.

One aspect of the present disclosure relates to the tosylate salt having:

a) an X-ray powder diffraction pattern substantially as shown in FIG. 25;

b) a differential scanning calorimetry thermogram substantially as shown in FIG. 26; and/or c) a thermogravimetric analysis profile substantially as shown in FIG. 27.

The crystalline forms described herein can be prepared by any of the suitable procedures known in the art for preparing crystalline polymorphs. In some embodiments the crystalline forms described herein are prepared according to the Examples. In some embodiments, the crystalline forms described herein can be prepared by heating crystalline forms other than the crystalline forms described herein. In some embodiments, the crystalline forms described herein can be prepared by recrystallizing crystalline forms other than the crystalline forms described herein.

Compounds of Formula (IIe) of the present disclosure may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis,* 3rd Edition, 1999 [Wiley]).

It is Understood that the Present Disclosure Embraces Each Enantiomer and Mixtures thereof. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment

In addition to the foregoing beneficial uses for the modulators of 5-$HT_{2A}$ serotonin receptor activity disclosed herein, the compounds disclosed herein are useful in the treatment of several additional diseases and disorders, and in the amelioration of symptoms thereof. Without limitation, these include the following:

The compounds of Formula (IIe), and pharmaceutically acceptable salts thereof, are useful as 5-$HT_{2A}$ serotonin receptor modulators for the treatment of disorders associated with 5-$HT_{2A}$ serotonin receptor expression and/or activity, such as cardiovascular disorders (for example, coronary artery disease, myocardial infarction, transient ischemic attack, angina, stroke, atrial fibrillation, platelet aggregation, and blood clot formation or symptoms thereof.

The modulators of 5-$HT_{2A}$ receptor activity disclosed herein are believed to be useful in the treatment of several diseases and disorders, and in the amelioration of symptoms thereof. Without limitation, some of them include the following: Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood as a result of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction. Stroke is an event in which the brain does not receive enough oxygen-rich blood, usually due to blockage of a cerebral blood vessel by a blood clot. In high-risk patients, taking antiplatelets regularly has been found to prevent the formation blood clots that cause first or second strokes.

Angioplasty is a catheter-based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism). 5-$HT_{2A}$ receptors are expressed on smooth muscle of blood vessels and 5-HT secreted by activated platelets causes vasoconstriction as well as activation of additional platelets during clotting. There is evidence that a 5-$HT_{2A}$ inverse agonist will inhibit platelet aggregation and thus be a potential treatment as an antiplatelet therapy (see Satimura, K, et al., Clin Cardiol 2002 Jan. 25 (1): 28-32; and Wilson, H. C et al., Thromb Haemost 1991 Sep. 2; 66 (3): 355-60).

The 5-$HT_{2A}$ inverse agonists disclosed herein provide beneficial improvement in microcirculation to patients in need of antiplatelet therapy by antagonizing the vasoconstrictive products of the aggregating platelets in, for example and not limitation, the indications described above. Accordingly, in some embodiments, the present invention provides methods for reducing platelet aggregation in a patient in need thereof comprising administering to said patient a composition comprising a 5-$HT_{2A}$ inverse agonist disclosed herein. In further embodiments, the present invention provides methods for treating coronary artery disease, myocardial infarction, transient ischemic attack, angina, stroke, atrial fibrillation, or a symptom of any of the foregoing in a patient in need of said treatment, comprising administering to said patient a composition comprising a 5-$HT_{2A}$ inverse agonist disclosed herein.

In further embodiments, the present invention provides methods for reducing risk of blood clot formation in an angioplasty or coronary bypass surgery patient, or a patient suffering from atrial fibrillation, comprising administering to a said patient a composition comprising a 5-$HT_{2A}$ inverse agonist disclosed herein at a time where such risk exists.

In further embodiments, the present invention provides methods for reducing risk of, or treating the effects of, PCI, comprising administering to a patient a composition comprising a 5-$HT_{2A}$ inverse agonist disclosed herein at a time where such risk exists.

In further embodiments, the present invention provides methods for the prevention or treatment of Raynaud's, comprising administering to a patient a composition comprising a 5-$HT_{2A}$ inverse agonist disclosed herein.

Synthetic Methods:

Example processes and intermediates of the present disclosure are provided below in Scheme A. As will be appreciated by those skilled in the art, the compounds provided herein, including salts thereof, can be prepared using known organic synthesis techniques and can be synthesized according to any of numerous possible synthetic routes, such as that provided in Scheme A.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry or by chromatographic methods such as high performance liquid chromatography (HPLC), liquid chromatography-mass spectroscopy (LC-MS), or thin layer chromatography (TLC). Compounds can be purified by those skilled in the art by a variety of methods, including high performance liquid chromatography (HPLC) and normal phase silica chromatography.

Scheme A provides general guidance in connection with preparing the compounds of the invention. For instance, the compound of Formula (IIe) can be prepared as shown in Scheme A.

Scheme A

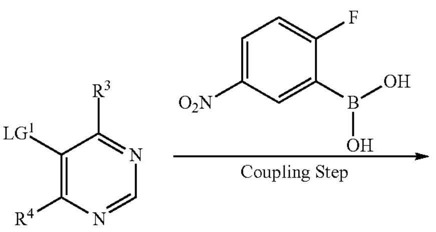

IIa

-continued

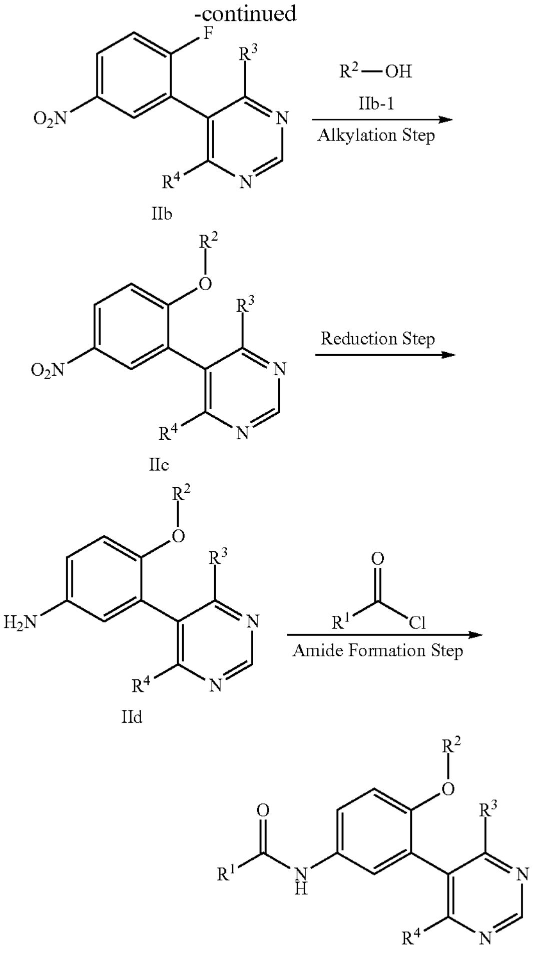

IIb

IIc

IId

IIe

Polymorphs and Pseudopolymorphs

The present disclosure includes polymorphs and pseudopolymorphs of the compound of Formula (Ia) of the present disclosure. Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, crystalline phases can contain an API host and either solvent or water molecules, respectively, as guests. Crystalline phases that share the same API host, but differ with respect to the guests, can be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stahly published a polymorph screen of 245 compounds consisting of a "wide variety of structural types" that revealed about 90% of them exhibited multiple solid forms. Overall, approximately half of the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, Crystal Growth & Design (2007), 7 (6), 1007-1026).

Certain Embodiments

One aspect of the present disclosure relates to methods for the treatment of a $5HT_{2A}$-related disorder disorder in an individual, comprising administering to the individual in need thereof, a therapeutically effective amount of a crystalline form as described herein or a pharmaceutical composition thereof.

One aspect of the present disclosure relates to a crystalline form of $5HT_{2A}$-related disorder as described herein, for use in a method of treatment of the human or animal body by therapy.

One aspect of the present disclosure relates to a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein, for use in a method of treatment of a $5HT_{2A}$-related disorder.

One aspect of the present disclosure relates to methods for the treatment of $5HT_{2A}$-related disorder in an individual, wherein the $5HT_{2A}$-related disorder is selected from a condition associated with platelet aggregation, coronary artery disease, myocardial infarction, transient ischemic attack, angina, stroke, atrial fibrillation, blood clot formation, or symptoms thereof, comprising administering to the individual in need thereof, a therapeutically effective amount of a crystalline form as described herein or a pharmaceutical composition thereof.

One aspect of the present disclosure relates to methods for the treatment of $5HT_{2A}$-related disorder in an individual, wherein the $5HT_{2A}$-related disorder is an effect of PCI selected from microvascular obstruction (MVO), myocardial injury, reduced cardiac function, or a major adverse cardiac event (MACE), comprising administering to the individual in need thereof, a therapeutically effective amount of a crystalline form as described herein or a pharmaceutical composition thereof.

One aspect of the present disclosure relates to methods for the treatment of $5HT_{2A}$-related disorder in an individual, wherein the $5HT_{2A}$-related disorder is Raynaud's, comprising administering to the individual in need thereof, a therapeutically effective amount of a crystalline form as described herein or a pharmaceutical composition thereof.

One aspect of the present disclosure relates to a method for treating a condition associated with platelet aggregation in an individual, comprising administering to said individual in need thereof, a therapeutically effective amount of a crystalline form as described herein or a pharmaceutical composition thereof.

One aspect of the present disclosure relates to a method for reducing the risk of blood clot formation in an individual, comprising administering to said individual in need thereof, a therapeutically effective amount of a crystalline form as described herein or a pharmaceutical composition thereof.

One aspect of the present disclosure relates to a method for reducing the risk of blood clot formation in an angioplasty or coronary bypass surgery individual, comprising administering to said individual in need thereof, a therapeutically effective amount of a crystalline form as described herein or a pharmaceutical composition thereof.

One aspect of the present disclosure relates to a method for reducing the risk of blood clot formation in an individual suffering from atrial fibrillation, comprising administering to said individual in need thereof, a therapeutically effective amount of a crystalline form as described herein or a pharmaceutical composition thereof.

One aspect of the present disclosure relates to methods for the treatment of a $5HT_{2A}$-related disorder disorder in an individual, comprising administering to the individual in need thereof, a therapeutically effective amount of a crystalline salt as described herein or a pharmaceutical composition thereof.

One aspect of the present disclosure relates to a crystalline salt of $5HT_{2A}$-related disorder as described herein, for use in a method of treatment of the human or animal body by therapy. One aspect of the present disclosure relates to a crystalline salt of N-(3-(4,6-dimethylpyrimidin-5-yl)-4-(2-(pyrrolidin-1-yl)ethoxy)phenyl)cyclopropanecarboxamide (Formula (Ia)) as described herein, for use in a method of treatment of a $5HT_{2A}$-related disorder.

One aspect of the present disclosure relates to methods for the treatment of $5HT_{2A}$-related disorder in an individual, wherein the $5HT_{2A}$-related disorder is selected from a condition associated with platelet aggregation, coronary artery disease, myocardial infarction, transient ischemic attack, angina, stroke, atrial fibrillation, blood clot formation, or symptoms thereof, comprising administering to the individual in need thereof, a therapeutically effective amount of a crystalline salt as described herein or a pharmaceutical composition thereof.

One aspect of the present disclosure relates to methods for the treatment of $5HT_{2A}$-related disorder in an individual, wherein the $5HT_{2A}$-related disorder is an effect of PCI selected from microvascular obstruction (MVO), myocardial injury, reduced cardiac function, or a major adverse cardiac event (MACE), comprising administering to the individual in need thereof, a therapeutically effective amount of a crystalline salt as described herein or a pharmaceutical composition thereof.

One aspect of the present disclosure relates to methods for the treatment of $5HT_{2A}$-related disorder in an individual, wherein the $5HT_{2A}$-related disorder is Raynaud's, comprising administering to the individual in need thereof, a therapeutically effective amount of a crystalline salt as described herein or a pharmaceutical composition thereof.

One aspect of the present disclosure relates to a method for treating a condition associated with platelet aggregation in an individual, comprising administering to said individual in need thereof, a therapeutically effective amount of a crystalline salt as described herein or a pharmaceutical composition thereof.

One aspect of the present disclosure relates to a method for reducing the risk of blood clot formation in an individual, comprising administering to said individual in need thereof, a therapeutically effective amount of a crystalline salt as described herein or a pharmaceutical composition thereof.

One aspect of the present disclosure relates to a method for reducing the risk of blood clot formation in an angioplasty or coronary bypass surgery individual, comprising administering to said individual in need thereof, a therapeutically effective amount of a crystalline salt as described herein or a pharmaceutical composition thereof.

One aspect of the present disclosure relates to a method for reducing the risk of blood clot formation in an individual suffering from atrial fibrillation, comprising administering to said individual in need thereof, a therapeutically effective amount of a crystalline salt as described herein or a pharmaceutical composition thereof.

Pharmaceutical Compositions

A further aspect of the present disclosure pertains to pharmaceutical compositions comprising the compounds of Formula (IIe), or pharmaceutically acceptable salt thereof as described herein and one or more pharmaceutically acceptable carriers. In some embodiments, the pharmaceutical composition comprises a compound of Formula (IIe), and a pharmaceutically acceptable carrier. In some embodiments, the pharmaceutical composition comprises a salt of the compound of Formula (IIe), and a pharmaceutically acceptable carrier.

Some embodiments of the present disclosure include a method of producing a pharmaceutical composition comprising admixing the compound of Formula (IIe), or pharmaceutically acceptable salt thereof and a pharmaceutically acceptable carrier. Some embodiments of the present disclosure include a method of producing a pharmaceutical composition comprising admixing a salt of the compound of Formula (IIe), as disclosed herein and a pharmaceutically acceptable carrier.

One aspect of the present disclosure relates to compositions comprising a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein.

One aspect of the present disclosure relates to compositions comprising a crystalline form of N-(3-(4,6-dimethylpyrimidin-5-yl)-4-(2-(pyrrolidin-1-yl)ethoxy)phenyl)cyclopropanecarboxamide (Formula (Ia)) as described herein, and a pharmaceutically acceptable carrier.

Some embodiments of the present disclosure include a method of producing a pharmaceutical composition comprising admixing at least one compound according to any of the compound embodiments disclosed herein and a pharmaceutically acceptable carrier.

One aspect of the present disclosure relates to process of making a composition comprising mixing a crystalline form of N-(3-(4,6-dimethylpyrimidin-5-yl)-4-(2-(pyrrolidin-1-yl)ethoxy)phenyl)cyclopropanecarboxamide, with a phamaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the disclosure in a suitable liquid vehicle and filter sterilizing the solution before filling and sealing an appropriate vial or ampule. These are just a few examples of the many appropriate methods well known in the art for preparing dosage forms.

A compound of the present disclosure can be formulated into pharmaceutical compositions using techniques well known to those in the art. Suitable pharmaceutically-acceptable carriers, outside those mentioned herein, are known in the art; for example, see Remington, *The Science and Practice of Pharmacy,* $20^{th}$ Edition, 2000, Lippincott Williams & Wilkins, (Editors: Gennaro et al.)

While it is possible that, for use in the prophylaxis or treatment, a compound of the disclosure may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the disclosure, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present disclosure or a solvate, hydrate or physiologically functional derivative thereof can be used as active ingredients in pharmaceutical compositions, specifically as 5-$HT_{2A}$ serotonin receptor modulators. By the term "active ingredient" is defined in the context of a "pharmaceutical composition" and refers to a component of a pharmaceutical composition that provides the primary pharmacological effect, as opposed to an "inactive ingredient" which would generally be recognized as providing no pharmaceutical benefit.

The dose when using the compounds of the present disclosure can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis conducted or on whether further active compounds are administered in addition to the compounds of the present disclosure. Representative doses of the present disclosure include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds of the present disclosure and as part of a drug combination. The dosage regimen for treating a disease condition with the compounds and/or compositions of this disclosure is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this disclosure.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present disclosure can be administrated in a wide variety of oral and parenteral dosage forms. It will be obvious to those skilled in the art that the following dosage forms may comprise, as the active component, either a compound of the disclosure or a pharmaceutically acceptable salt, solvate or hydrate of a compound of the disclosure.

For preparing pharmaceutical compositions from the compounds of the present disclosure, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" includes the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present disclosure may thus be formulated for parenteral administration (e.g., by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which can be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the disclosure may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present disclosure or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present disclosure as an aerosol can be prepared by processes well known to the person skilled in the art. For their preparation, for example, solutions or dispersions of the compounds of the present disclosure in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively, the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the disclosure may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds of the present disclosure which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine (N1,N2-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino) hexane-1,2,3,4,5-pentaol), procaine (2-(diethylamino)ethyl 4-aminobenzoate), and the like. Certain pharmaceutically acceptable salts are listed in Berge, et al., *Journal of Pharmaceutical Sciences,* 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this disclosure may form solvates with standard low molecular weight solvents using methods known to the skilled artisan.

Compounds of the present disclosure can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the disclosure containing one or more specialized non-toxic protective groups used in a transient manner to alter or to eliminate a property of the compound.

Some embodiments of the present disclosure include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

Other Utilities

Another object of the present disclosure relates to radio-labeled compounds of the present disclosure that would be useful not only in radio-imaging but also in assays, both in vitro and in vivo, for localizing and quantitating 5-$HT_{2A}$ receptors in tissue samples, including human, and for identifying 5-$HT_{2A}$ receptor ligands by inhibition binding of a radio-labeled compound. It is a further object of this disclosure to develop novel 5-$HT_{2A}$ receptor assays of which comprise such radio-labeled compounds.

The present disclosure embraces isotopically-labeled crystalline forms of the present disclosure. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{75}Br$, $^{76}Br$, $^{77}Br$, $^{82}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro 5-$HT_{2A}$ serotonin receptor labeling and competition assays, compounds that incorporate $^{3}H$, $^{14}C$, $^{82}Br$, $^{125}I$, $^{131}I$ or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a crystalline form of Compound Ia that has incorporated at least one radionuclide; in some embodiments the radionuclide is selected from the group consisting of $^{3}H$, $^{14}C$, $^{125}I$, $^{35}S$ and $^{82}Br$.

Certain isotopically-labeled crystalline forms of the present disclosure are useful in compound and/or substrate tissue distribution assays. In some embodiments the radionuclide $^{3}H$ and/or $^{14}C$ isotopes are useful in these studies. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled crystalline forms of the present disclosure can generally be prepared by following procedures analogous to those disclosed in the and Examples infra, by substituting an isotopically labeled reagent for a non-isotopically labeled reagent. Other synthetic methods that are useful are discussed infra. Moreover, it should be understood that all of the atoms represented in the compounds of the disclosure can be either the most commonly occurring isotope of such atoms or the scarcer radio-isotope or nonradioactive isotope.

Synthetic methods for incorporating radio-isotopes into organic compounds are applicable to compounds of the disclosure and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl (3H) products by treating appropriate precursors with high specific activity methyl iodide (3H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in J. Org. Chem., 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.,* 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e., $Pd(Ph_3P)_4$] or through an aryl or heteroaryl lithium, in the presence of a tri-alkyltinhalide or hexaalkylditin [e.g., $(CH_3)_3SnSn(CH_3)_3$].

Some embodiments of the present disclosure include a method of producing a pharmaceutical composition for "combination therapy" comprising admixing the compound of Formula (IIe) or any other Formula herein, such as Formula (Ia), or pharmaceutically acceptable salt thereof together with at least one known pharmaceutical agent as described herein and a pharmaceutically acceptable carrier.

It is noted that when the 5-$HT_{2A}$ receptor modulators are utilized as active ingredients in a pharmaceutical composition, these are not intended for use only in humans, but in other non-human mammals as well. Indeed, advances in the area of animal health-care mandate that consideration be given for the use of active agents, such as 5-$HT_{2A}$ receptor modulators, for the treatment of a 5-$HT_{2A}$ mediated diseases or disorders in domestic animals (e.g., cats and dogs) and in other domestic animals (e.g., such as cows, chickens, and fish). Those of ordinary skill in the art will understand the utility of such compounds in such settings.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are illustrative and not limiting.

EXAMPLES

Example 1: Preparation of 5-(2-fluoro-5-nitrophenyl)-4,6-dimethylpyrimidine (Compound IIb-1)

IIb-1

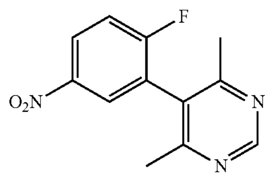

Tetrahydrofuran (THF) (37.20 kg) was added to a solution of potassium phosphate tribasic (10.24 kg) in purified water (24.32 kg), and the mixture was heated to 20-30° C. 5-Bromo-4,6-dimethylpyrimidine (3.00 kg, 16.0 mol) and 2-Fluoro-5-nitrophenylboronic acid (3.26, 17.6 mol) were added, and the reactor interior was rinsed down with purified water (6.00 kg). The mixture was sparged with nitrogen, and a nitrogen atmosphere was maintained for the duration of the reaction. SPhos Pd G3 (0.50 kg) was added, and the reaction mixture was heated to 40-45° C. for 1 h. The mixture was heated to 55-65° C. and stirred at this temperature for 4 h, when HPLC analysis showed ≤1% of 5-bromo-4,6-dimethylpyrimidine remained.

The reaction was cooled to 25-35° C., celite (0.46 kg) was added, and the mixture was stirred for 1 h. Solids were filtered and washed with THF (3.80 kg), and the washing was combined with the filtrate. The filtrate was heated to 25-35° C., stirring was stopped, and the mixture was allowed to settle. The bottom aqueous layer was back-extracted with methyl tert-butyl ether (MTBE) (11.18 kg), and the organic layers were combined. Celite (0.3 kg) was added, and the mixture was stirred for 1 h. Solids were filtered and washed with MTBE (3.00 kg), and the washing was combined with the filtrate. The filtrate was concentrated at atmospheric pressure and temperature ≤65° C. to a target volume of 15.00 L. Heptane (21.00 kg) was added, and the mixture was concentrated at atmospheric pressure and temperature ≤65° C. to a target volume of 18.00 L. The mixture was cooled to <50° C., Isopropyl Alcohol (IPA) (0.6 kg) was added, and the resulting mixture was cooled to 20-30° C. and stirred for 2 h. The mixture was filtered, and the filter cake was washed with Heptane/IPA (95:5 v/v, 10.35 kg). The solids were dried under vacuum (≥26 inches Hg) and nitrogen purge at 30-40° C. for 12 h to give 3.90 kg (15.8 mol, 98% yield) of 5-(2-fluoro-5-nitrophenyl)-4,6-dimethylpyrimidine (IIb-1). $^1$H NMR (400 MHz, methanol-$d_4$) δ=8.96 (s, 1H), 8.50-8.44 (m, 1H), 8.36 (dd, J=2.9, 6.1 Hz, 1H), 7.58 (t, J=8.8 Hz, 1H), 2.32 (s, 6H).

Example 2: Preparation of 4,6-dimethyl-5-(5-nitro-2-(2-(pyrrolidin-1-yl)ethoxy)phenyl)pyrimidine (Compound IIc-1, Hydrochloride Salt)

IIc-1

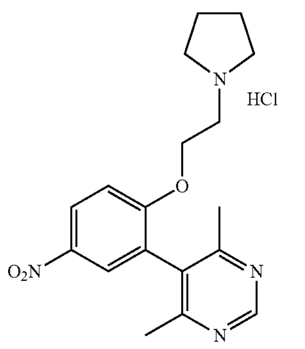

Dimethylformamide (DMF) (31.65 kg), cesium carbonate (milled) (11.18 kg), 5-(2-fluoro-5-nitrophenyl)-4,6-dimethylpyrimidine (3.36 kg, 13.6 mol), and 1-(2-hydroxyethyl) pyrrolidine (1.88 kg, 16.3 mol) were combined under nitrogen, and the mixture was heated to 80-90° C. and stirred at this temperature for 22 h, when HPLC analysis showed <3% of 5-(2-fluoro-5-nitrophenyl)-4,6-dimethylpyrimidine remained.

The mixture was cooled to 15-25° C., and purified water (50.55 kg) was added over 1 h while maintaining temperature ≤30° C. MTBE (50.55 kg) was added, and the mixture was stirred for 30 min at 20-30° C. Layers were allowed to settle, and the bottom aqueous layer was back-extracted with MTBE (50.65 kg). The organic layers were combined, washed with 5% sodium chloride aqueous solution (2×16.80 kg), and concentrated under vacuum at ≤55° C. to a target volume of 16.80 L. MTBE (80.30 kg) was added, and the mixture was filtered to remove solids. The solids were washed with MTBE (6.8 kg), and the wash was combined with the filtrate.

Hydrogen chloride (3M in methanol) (3.94 kg) was added to the filtrate while maintaining temperature ≤30° C. over 30 min, during which, the product began to precipitate. The resulting slurry was stirred for 1 h at 15-30° C., filtered, washed with MTBE (2×10 kg), and dried under vacuum (≥26 inches Hg) and nitrogen purge at 15-25° C. for 14 h to give 3.00 kg of product.

The product was dissolved in ethanol (45.50 kg) at 50-60° C. and recrystallized by addition of MTBE (22.20 kg), cooling to 15-25° C., and stirring at this temperature for at least 8 h. The recrystallized product was filtered and washed with MTBE/Ethanol (3:1 v/v, 11 kg) and MTBE (8.60 kg), and dried under vacuum (≥26 inches Hg) and nitrogen purge at 15-25° C. for at least 12 h to give 2.25 kg (5.94 mol, 44% yield) of 4,6-dimethyl-5-(5-nitro-2-(2-(pyrrolidin-1-yl) ethoxy)phenyl)pyrimidine hydrochloride (IIc-1).

Example 3: Preparation of 3-(4,6-dimethylpyrimidin-5-yl)-4-(2-(pyrrolidin-1-yl)ethoxy) aniline (Compound IId-1, Hydrochloride Salt)

IId-1

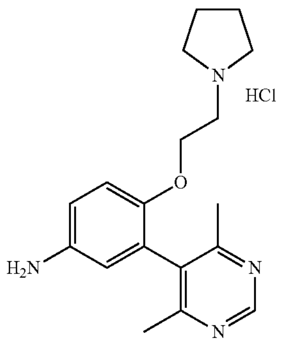

4,6-Dimethyl-5-(5-nitro-2-(2-(pyrrolidin-1-yl)ethoxy) phenyl)pyrimidine hydrochloride (2.25 kg, 5.94 mol) was dissolved in purified water (25.14 kg) under nitrogen. In a separate reactor, palladium (Pd) (10% on Carbon, 0.24 kg) and ethanol (26.80 kg) were combined, and the mixture was purged with nitrogen/vacuum three times. To this Pd/C in ethanol mixture, the 4,6-Dimethyl-5-(5-nitro-2-(2-(pyrrolidin-1-yl)ethoxy)phenyl)pyrimidine hydrochloride solution was added under vacuum, and the mixture was purged with nitrogen/vacuum three times. The reactor was pressurized to 10-20 psig with hydrogen and maintained at this pressure until reaction completion. The reaction mixture was stirred at 15-25° C. for 27 h, when HPLC analysis showed ≤1% 4,6-Dimethyl-5-(5-nitro-2-(2-(pyrrolidin-1-yl)ethoxy)phenyl)pyrimidine hydrochloride remained.

The hydrogen pressure was released through a scrubber, and the reactor was purged with nitrogen three times and maintained under nitrogen for the duration of the workup. The mixture was filtered, washed with purified water (5.62 kg), and the wash was combined with the filtrate. The filtrate was stirred with SiliaMetS Thiourea (0.30 kg) at 15-25° C. for 24 h to scavenge residual Pd. The solids were filtered, washed with purified water (5.50 kg), and the wash was combined with the filtrate. The filtrate was concentrated under vacuum at temperature ≤45° C. to a volume of 15 L. Residual water was removed through azeotropic distillation with Ethanol (10×18 kg) to a final volume of ~20 L until Karl Fischer analysis showed ≤1% water remained. The mixture was cooled to 0-10° C. and stirred at this temperature for 5 h. The product was filtered, washed with cold Ethanol (11.44 kg, precooled to −5° C.), cold MTBE (11.48 kg, precooled to −5° C.), and dried under vacuum (≥26 inches Hg) and nitrogen purge at 15-25° C. for 17 h until LOD ≤5% to give 1.71 kg (4.90 mol, 83% yield) of 3-(4,6-dimethylpyrimidin-5-yl)-4-(2-(pyrrolidin-1-yl) ethoxy) aniline hydrochloride (IId-1). $^1$H NMR (400 MHz, DMSO-d6) δ=8.81 (s, 1H), 6.88 (d, J=8.3 Hz, 1H), 6.62 (dd, J=2.9, 8.8 Hz, 1H), 6.35 (d, J=2.9 Hz, 1H), 4.78 (br s, 2H), 3.86 (t, J=5.9 Hz, 2H), 2.51 (d, J=2.0 Hz, 2H), 2.26-2.20 (m, 4H), 2.17 (s, 6H), 1.54 (td, J=3.1, 6.6 Hz, 4H).

Example 4: Preparation of N-(3-(4,6-dimethylpyrimidin-5-yl)-4-(2-(pyrrolidin-1-yl)ethoxy)phenyl) cyclopropanecarboxamide (Compound Ia)

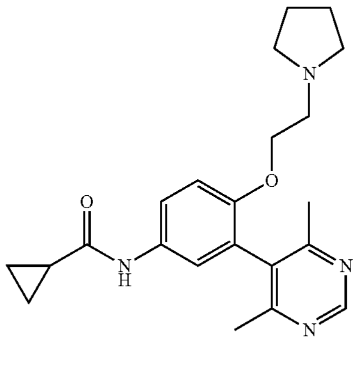
Ia

To a solution of potassium carbonate (1.84 kg) in purified water (29.70 kg) was added methylene chloride (DCM) (13.60 kg) and 3-(4,6-dimethylpyrimidin-5-yl)-4-(2-(pyrrolidin-1-yl)ethoxy) aniline hydrochloride (1.55 kg, 4.44 mol) at 15-25° C. A solution of cyclopropane carbonyl chloride (0.96 kg) in DCM (31.15 kg) was added over 45 min, maintaining temperature at 15-25° C. The biphasic reaction mixture was stirred at 15-25° C. for 90 min, when HPLC analysis showed ≤1% of 3-(4,6-dimethylpyrimidin-5-yl)-4-(2-(pyrrolidin-1-yl)ethoxy) aniline hydrochloride remained.

Stirring was stopped, the layers were allowed to settle, and the bottom product organic layer was separated. The aqueous layer was back-extracted with DCM (20.65 kg), and the organic layers were combined. The organic layer was washed with potassium carbonate aqueous solution (5%, 15.52 kg), purified water (15.50 kg), and polish-filtered through a 0.2-micron cartridge filter, rinsing with DCM (6.20 kg) and combining the rinse with the filtrate. MTBE (23.30 kg) was added to the filtrate, and the mixture was concentrated to a residue by distillation at atmospheric pressure and temperature of 50-55° C. The residue was cooled to 45° C., MTBE (20.55 kg) was added, and the mixture was cooled to 15-25° C. over 1 h, during which, a slurry formed. The slurry was cooled to 0-10° C. and stirred at this temperature for 1 h. The solids were filtered, washed with cold MTBE (12.00 kg, precooled to 0° C.), and dried under vacuum (≥26 inches Hg) and nitrogen purge at 15-25° C. for at least 12 h to give 1.13 kg (2.97 mol, 67% yield) of N-(3-(4,6-dimethylpyrimidin-5-yl)-4-(2-(pyrrolidin-1-yl) ethoxy)phenyl)cyclopropanecarboxamide (la) in a crystalline form. $^1H$ NMR (400 MHz, methanol-$d_4$) δ=8.83 (s, 1H), 7.58 (dd, J=2.6, 8.9 Hz, 1H), 7.39 (d, J=2.6 Hz, 1H), 7.12 (d, J=8.9 Hz, 1H), 4.11 (t, J=5.4 Hz, 2H), 2.73 (t, J=5.4 Hz, 2H), 2.41-2.33 (m, 4H), 2.27 (s, 6H), 1.78-1.72 (m, 1H), 1.69 (td, J=3.3, 6.9 Hz, 4H), 0.97-0.90 (m, 2H), 0.88-0.80 (m, 2H). LC/MS m/z=380.9 $[M+H]^+$.

The material was characterized by PXRD (FIG. 1), and DSC/TGA (FIGS. 2 and 3 respectively). DSC analysis showed a broad endothermic melt with onset at 140.1° C. and peak at 151.5° C. TGA analysis displayed a 3.6 wt. % loss up to 240° C. (theoretically 0.8 eq. water).

Example 5: Preparation of N-(3-(4,6-dimethylpyrimidin-5-yl)-4-(2-(pyrrolidin-1-yl)ethoxy)phenyl) cyclopropanecarboxamide (Compound Ia; Besylate Salt)

N-(3-(4,6-dimethylpyrimidin-5-yl)-4-(2-(pyrrolidin-1-yl) ethoxy)phenyl)cyclopropanecarboxamide (1.0 g, 2.13 mmol) was dissolved in 20 mL ethyl acetate. Benzenesulfonic acid (0.416 g, 2.63 mmol) was dissolved in 4 mL ethyl acetate and this solution was added dropwise over 5 minutes to the N-(3-(4,6-dimethylpyrimidin-5-yl)-4-(2-(pyrrolidin-1-yl)ethoxy)phenyl)cyclopropanecarboxamide solution at 40° C. and was stirred at this temperature for a further two hours. The benzenesulfonate (besylate) salt precipitated and was collected by filtration using a Buchner funnel and dried at 40° C. for 16 hours.

The resulting crystalline material, besylate salt characterized by PXRD (FIG. 4), and DSC/TGA (FIGS. 5 and 6 respectively). DSC analysis showed a endothermic melt with onset at 219.4° C. and peak at 225.7° C. TGA analysis displayed a 2.1 wt. % loss up to 220° C. (theoretically 0.64 eq. water).

Example 6: Preparation of N-(3-(4,6-dimethylpyrimidin-5-yl)-4-(2-(pyrrolidin-1-yl)ethoxy)phenyl) cyclopropanecarboxamide (Compound Ia; Citrate Salt)

N-(3-(4,6-dimethylpyrimidin-5-yl)-4-(2-(pyrrolidin-1-yl) ethoxy)phenyl)cyclopropanecarboxamide (2.00 g, 5.26 mmol) was added to a 250 mL round bottom flask and dissolved in ethanol (40 mL). Citric acid monohydrate (1.105 g, 5.26 mmol) was added to a 100 mL Erlenmeyer flask and dissolved in ethanol (10 mL). The citric acid solution was added to the N-(3-(4,6-dimethylpyrimidin-5-yl)-4-(2-(pyrrolidin-1-yl)ethoxy)phenyl)cyclopropanecarboxamide solution in 0.5 mL portions over 10 minutes while stirring the reaction. The citrate salt began to slowly precipitate form solution after a few minutes and the reaction was stirred for 24 h. The salt was isolated by Buchner filtration and subsequently dried in the oven at 40° C. for 5 hours.

The resulting crystalline material, citrate salt characterized by PXRD (FIG. 7), and DSC/TGA (FIGS. 8 and 9 respectively). DSC analysis showed a endothermic melt with onset at 172.2° C. and peak at 173.5° C. TGA analysis displayed no significant mass loss until the melt/dissociation point.

Example 7: Preparation of N-(3-(4,6-dimethylpyrimidin-5-yl)-4-(2-(pyrrolidin-1-yl)ethoxy)phenyl) cyclopropanecarboxamide (Compound Ia; Fumarate Salt)

N-(3-(4,6-dimethylpyrimidin-5-yl)-4-(2-(pyrrolidin-1-yl) ethoxy)phenyl)cyclopropanecarboxamide (20 mg) was dissolved in 0.2 ml ethyl acetate and an equimolar amount of fumaric acid was also dissolved in 0.2 mL ethyl acetate. N-(3-(4,6-dimethylpyrimidin-5-yl)-4-(2-(pyrrolidin-1-yl) ethoxy)phenyl)cyclopropanecarboxamide solution was added to the fumaric acid solution while stirring at 40° C. and then stirred at 40° C.40° C. for one hour. Then it was cooled to 20° C. with stirring for additional 72 hours. The precipitated salt was isolated by centrifugation.

The resulting crystalline material, fumarate salt, was characterized by PXRD (FIG. 10), and DSC/TGA (FIGS. 11 and 12 respectively). DSC analysis showed a endothermic melt with onset at 151.3° C. and peak at 156.1° C. TGA analysis displayed a 4.9 wt. % loss up to 200° C. (theoretically 2.5 eq. water).

Example 8: Preparation of N-(3-(4,6-dimethylpyrimidin-5-yl)-4-(2-(pyrrolidin-1-yl)ethoxy)phenyl) cyclopropanecarboxamide (Compound Ia; Hydrochloride Salt)

N-(3-(4,6-dimethylpyrimidin-5-yl)-4-(2-(pyrrolidin-1-yl) ethoxy)phenyl)cyclopropanecarboxamide (100 mg) was dissolved in 2 mL isopropyl acetate and heated to 40° C. and an equimolar amount of aqueous 3.3M HCl solution (79.6 mL) was added and stirred for one hour at 40° C. The reaction was stirred overnight during which it cooled down to 20° C. The reaction mixture was evaporated at room temperature and then the resulting solid was dried in a vacuum oven at 40° C. for 48 hours.

The resulting crystalline material, hydrochloride salt, was characterized by PXRD (FIG. 13), and DSC/TGA (FIGS. 14 and 15 respectively). DSC analysis showed a broad endothermic event (onset: 23.8° C.; peak: 74.6° C.) associated with solvent loss and a second endothermic event (onset: 188.5° C.; peak: 193.9° C.) associated with melting. TGA analysis displayed a 4.3 wt. % loss up to 200° C. (theoretically 1.03 eq. water).

Example 9: Preparation of N-(3-(4,6-dimethylpyrimidin-5-yl)-4-(2-(pyrrolidin-1-yl)ethoxy)phenyl) cyclopropanecarboxamide (Compound Ia; Mesylate Salt)

N-(3-(4,6-dimethylpyrimidin-5-yl)-4-(2-(pyrrolidin-1-yl) ethoxy)phenyl)cyclopropanecarboxamide (20 mg) was dissolved in 0.4 mL ethyl acetate and heated to 40° C. with rapid stirring and 1.0 equivalent of methanesulfonic acid (3.3M in ethyl acetate) solution was added and continued stirring at 40° C. for one hour and then stirred overnight during which it cooled down to 20° C. The reaction mixture was evaporated at room temperature and then the resulting solid was dried in a vacuum oven at 40° C. for 24 hours.

The resulting crystalline material, mesylate salt, was characterized by PXRD (FIG. 16), and DSC/TGA (FIGS. 17 and 18 respectively). DSC analysis showed one endothermic event (onset: 181.4° C.; peak: 189.7° C.) associated with melting. TGA analysis displayed a 2.2 wt. % loss up to 180° C. (theoretically 0.6 eq. water).

Example 10: Preparation of N-(3-(4,6-dimethylpyrimidin-5-yl)-4-(2-(pyrrolidin-1-yl)ethoxy)phenyl) cyclopropanecarboxamide (Compound Ia; Phosphate Salt)

N-(3-(4,6-dimethylpyrimidin-5-yl)-4-(2-(pyrrolidin-1-yl) ethoxy)phenyl)cyclopropanecarboxamide (100 mg) was dissolved in 2.0 mL acetonitrile and heated to 40° C. with rapid stirring and 1.0 equivalent of phosphoric acid (79 mL, 3.3M) solution was added and continued stirring at 40° C. for one hour and then it was cooled down to 20° C. The reaction mixture was decanted and the collected solids dried in a vacuum oven at 40° C. for 3 hours.

The resulting crystalline material, phosphate salt, was characterized by PXRD (FIG. 19), and DSC/TGA (FIGS. 20 and 21 respectively). DSC analysis showed one endothermic event (onset: 201.7° C.; peak: 217.9° C.) associated with melting. TGA analysis displayed a 3.4 wt. % loss up to 180° C. (theoretically 0.9 eq. water).

Example 11: Preparation of N-(3-(4,6-dimethylpyrimidin-5-yl)-4-(2-(pyrrolidin-1-yl)ethoxy)phenyl) cyclopropanecarboxamide (Compound Ia; Succinate Salt)

N-(3-(4,6-dimethylpyrimidin-5-yl)-4-(2-(pyrrolidin-1-yl) ethoxy)phenyl)cyclopropanecarboxamide (175 mg) was dissolved in 3.5 mL ethyl acetate and heated to 40° C. with rapid stirring and 1.0 equivalent of succinic acid solution (in ethyl acetate) was added and continued stirring at 40° C. for one hour and then it was cooled down to 20° C. overnight. The precipitated solids were collected by filtration and the collected solids dried in a vacuum oven at 40° C.

The resulting crystalline material, succinate salt, was characterized by PXRD (FIG. 22), and DSC/TGA (FIGS. 23 and 24 respectively). DSC analysis showed one endothermic event (onset: 116.3° C.; peak: 119.8° C.) associated with melting. TGA analysis displayed a 24.8 wt. % loss up to 150° C. (theoretically 1.05 eq succinic acid).

Example 12: Preparation of N-(3-(4,6-dimethylpyrimidin-5-yl)-4-(2-(pyrrolidin-1-yl)ethoxy)phenyl) cyclopropanecarboxamide (Compound Ia; Tosylate Salt)

N-(3-(4,6-dimethylpyrimidin-5-yl)-4-(2-(pyrrolidin-1-yl) ethoxy)phenyl)cyclopropanecarboxamide (175 mg) was dissolved in 3.5 mL ethyl acetate and heated to 40° C. with rapid stirring and 1.0 equivalent of p-toluenesulfonic acid solution (in ethyl acetate) was added and continued stirring at 40° C. for one hour and then it was cooled down to 20° C. overnight. The precipitated solids were collected by filtration and the collected solids dried in a vacuum oven at 40° C.

The resulting crystalline material, tosylate salt, was characterized by PXRD (FIG. 25), and DSC/TGA (FIGS. 26 and 27 respectively). DSC analysis showed one endothermic event (onset: 151.3° C.; peak: 170.1° C.) associated with melting. TGA analysis displayed a 1.5 wt. % loss up to 168° C. (theoretically 0.47 eq. water).

Example 12: Powder X-ray Diffraction

PXRD analysis was carried out on a PANalytical X'pert pro with PIXcel detector (128 channels), scanning the samples between 3 and 35° 2θ. The material was gently ground (where required) to release any agglomerates and loaded onto a multi-well plate with Kapton or Mylar polymer film to support the sample. The multi-well plate was then placed into the diffractometer and analysed using Cu K radiation ($\alpha_1$ $\lambda$=1.54060 Å; $\alpha_2$=1.54443 Å; $\beta$=1.39225 Å; $\alpha_1$: $\alpha_2$ ratio=0.5) running in transmission mode (step size 0.0130° 2θ, step time 18.87 s) using 40 kV/40 mA generator settings. Data were visualized and images generatedusing the HighScore Plus 4.7 desktop application (PANalytical, 2017).

Example 13: Differential Scanning Calorimetry (DSC)

Approximately, 1-5 mg of material was weighed into an aluminium DSC pan and sealed non-hermetically with an aluminium lid. The sample pan was then loaded into a TA Instruments Discovery DSC 2500 differential scanning calorimeter equipped with a RC90 cooler. The sample and reference were heated to 200° C., 250° C., or 300° C. at a scan rate of 10° C./min and the resulting heat flow response monitored. The sample was re-cooled to 20° C. and then reheated again to the specified temperature all at 10° C./min. Nitrogen was used as the purge gas, at a flow rate of 50 $cm^3$/min.

Example 14: Thermal Gravimetric Analysis

Approximately, 5-10 mg of material was added into a pre-tared open aluminium pan and loaded into a TA Instruments Discovery SDT 650 Auto-Simultaneous DSC and held at room temperature. The sample was then heated at a rate of 10° C./min from 30° C. to 400° C. during which time the change in sample weight was recorded along with the heat flow response (DSC). Nitrogen was used as the sample purge gas, at a flow rate of 200 $cm^3$/min.

Those skilled in the art will recognize that various modifications, additions, substitutions, and variations to the illustrative examples set forth herein can be made without departing from the spirit of the invention and are, therefore, considered within the scope of the invention.

What is claimed is:

1. A crystalline form of N-(3-(4,6-dimethylpyrimidin-5-yl)-4-(2-(pyrrolidin-1-yl)ethoxy)phenyl)cyclopropanecarboxamide.

2. The crystalline form according to claim 1, comprising an X-ray powder diffraction pattern comprising a peak, in terms of 2θ, at 5.3°±0.2°, 10.6°±0.2°, 12.4°±0.2°.

3. The crystalline form according to claim 1, comprising an X-ray powder diffraction pattern comprising peaks, in terms of 2θ, at 5.3°±0.2°, 10.6°±0.2°, 12.4°±0.2°, 14.9°±0.2°, and 15.9°±0.2°.

4. The crystalline form according to claim 1, comprising an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°, 19.8°±0.2°, 20.1°±0.2°, and 21.1°±0.2°, 22.0°±0.2°, 23.3°±0.2°, and 24.9°±0.2°.

5. The crystalline form according to claim 1, wherein said crystalline form has a differential scanning calorimetry thermogram comprising an endotherm with an extrapolated onset temperature between about 138.1° C. and about 153.5° C.

6. The crystalline form according to claim 1, wherein said crystalline form has a thermogravimetric analysis profile showing about 4.0% weight loss below about 240° C.

7. The crystalline form according to claim 1, wherein said crystalline form has:

a) an X-ray powder diffraction pattern comprising peaks, in terms of 2θ, at 5.3°±0.2°, 10.6°±0.2°, 12.4°±0.2°, 14.9°±0.2°, 15.9°±0.2°, 16.2°±0.2°, 16.8°±0.2°, 18.8°±0.2°, and 19.0°±0.2°;

b) a differential scanning calorimetry thermogram comprising an endotherm with an extrapolated onset temperature between about 138.1° C. and about 153.5° C.; and/or c) a thermogravimetric analysis profile showing about 4.0% weight loss below about 240° C.

8. A pharmaceutical composition comprising the crystalline form of N-(3-(4,6-dimethylpyrimidin-5-yl)-4-(2-(pyrrolidin-1-yl)ethoxy)phenyl)cyclopropanecarboxamide of claim 1, and a pharmaceutically acceptable carrier.

9. A process for preparing a crystalline salt of N-(3-(4,6-dimethylpyrimidin-5-yl)-4-(2-(pyrrolidin-1-yl)ethoxy)phenyl)cyclopropanecarboxamide of Formula (Ia):

(Ia)

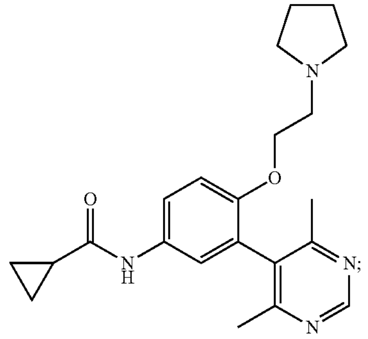

comprising the following steps:

a) contacting N-(3-(4,6-dimethylpyrimidin-5-yl)-4-(2-(pyrrolidin-1-yl)ethoxy)phenyl)cyclopropanecarboxamide (Formula (Ia)) with an acid, in the presence of a contacting-step solvent;

b) crystallizing said N-(3-(4,6-dimethylpyrimidin-5-yl)-4-(2-(pyrrolidin-1-yl)ethoxy)phenyl)cyclopropanecarboxamide (Formula (Ia)) to obtain a crystalline salt of N-(3-(4,6-dimethylpyrimidin-5-yl)-4-(2-(pyrrolidin-1-yl)ethoxy)phenyl)cyclopropanecarboxamide (Formula (Ia)) in a crystallizing mixture; and c) isolating said crystalline salt of N-(3-(4,6-dimethylpyrimidin-5-yl)-4-(2-(pyrrolidin-1-yl)ethoxy)phenyl)cyclopropanecarboxamide (Formula (Ia)) from said crystallizing mixture to obtain said crystalline salt of N-(3-(4,6-dimethylpyrimidin-5-yl)-4-(2-(pyrrolidin-1-yl)ethoxy)phenyl)cyclopropanecarboxamide (Formula (Ia)).

10. The process according to claim 9, wherein after said isolating, said crystalline salt of N-(3-(4,6-dimethylpyrimidin-5-yl)-4-(2-(pyrrolidin-1-yl)ethoxy)phenyl)cyclopropane carboxamide has a chemical purity of about 95% or greater.

11. A process of preparing a compound of Formula (IIe), comprising:

IIc

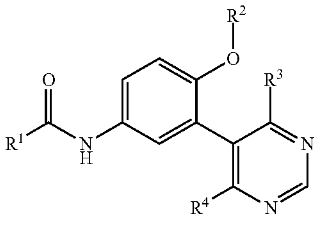

coupling a compound of Formula (IId) or a salt thereof:

IId

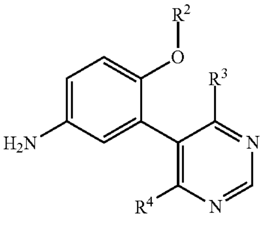

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$ ($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$ ($C_1$-$C_3$ alkyl), and optionally containing one additional heteroatom selected from the group of N, O, and S; and;

$R^3$ and $R^4$ are each independently selected from H, $C_1$-$C_6$ alkyl, and $C_1$-$C_6$ haloalkyl;

with an acyl chloride of Formula (IId-1)

IId-1

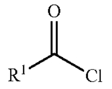

wherein $R^1$ is selected from $C_1$-$C_6$ alkyl, $C_3$-$C_6$ cycloalkyl, phenyl, 5-10 membered heteroaryl, and 5-9 membered heterocycloalkyl;

in the presence of a base and a solvent to form said compound of Formula (IIe).

12. The process of claim 11, wherein the compound of Formula (IId) or salt thereof has the formula:

IId

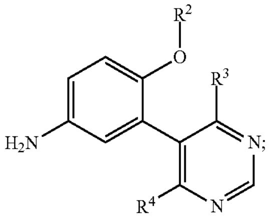

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-7 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl); and;

$R^3$ and $R^4$ are each independently selected from H, $C_1$-$C_6$ alkyl, and $C_1$-$C_6$ haloalkyl;

wherein the compound of Formula (IId) is prepared by a process comprising the step of reducing a compound of Formula (IIc) or a salt thereof:

IIc

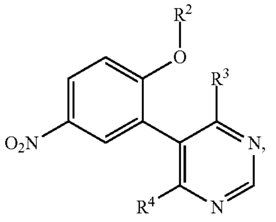

wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-7 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl); and;

$R^3$ and $R^4$ are each independently selected from H, $C_1$-$C_6$ alkyl, and $C_1$-$C_6$ haloalkyl.

13. The process according to claim 12, wherein:

said compound of Formula (IIc) or salt thereof is:

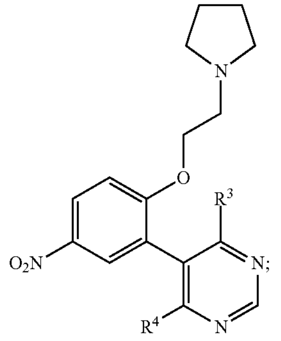

said step of reducing comprises contacting said compound of Formula (IIc) with a reducing-step agent comprising hydrogen and palladium/carbon (Pd/C); and said step of reducing comprises a solvent comprising ethanol and water.

14. The process of claim 13, wherein the compound of Formula (IIc) or a salt thereof is prepared by a process comprising a step of alkylating a compound of Formula (IIb-1):

IIb-1

$R^2$—OH, wherein $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), and —O—($C_1$-$C_3$ alkyl);

$R^{2A}$ and $R^{2B}$ are each independently selected from H, $C_1$-$C_3$ alkyl, $C_1$-$C_3$ haloalkyl, and $C_3$-$C_6$ cycloalkyl; or wherein $R^{2A}$ and $R^{2B}$, taken together with the nitrogen to which they are attached, form a 3-7 membered heterocycloalkyl ring optionally substituted with one or more substituents independently selected from halogen, oxo, —OH, $C_1$-$C_3$ alkyl, ($C_1$-$C_3$ haloalkyl), and —O—($C_1$-$C_3$ alkyl);

with a compound of Formula (IIb):

IIb

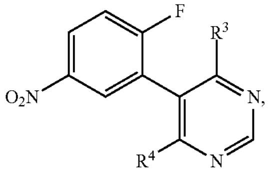

wherein $R^3$ and $R^4$ are each independently selected from H, $C_1$-$C_6$ alkyl, and $C_1$-$C_6$ haloalkyl;

wherein the step of alkylating is optionally followed by treatment with a mineral acid in the presence of an alcoholic solvent to form the salt of the compound of Formula (IIc).

15. A method of treating a $5HT_{2A}$-related disorder in an individual, comprising administering to said individual in need thereof, a therapeutically effective amount of the crystalline form according to claim 1.

16. A method of treating a disorder in an individual in need thereof, comprising administering to said individual in need thereof a therapeutically effective amount of the crystalline form of N-(3-(4,6-dimethylpyrimidin-5-yl)-4-(2-(pyrrolidin-1-yl)ethoxy)phenyl)cyclopropanecarboxamide of claim 1, wherein the disorder is selected from a condition associated with platelet aggregation; coronary artery disease; myocardial infarction; transient ischemic attack; angina; stroke; atrial fibrillation; blood clot formation; an effect of percutaneous coronary interventions (PCI) selected from microvascular obstruction (MVO), myocardial injury, reduced cardiac function, and a major adverse cardiac event (MACE); and Raynaud's disease or syndrome, or a symptom thereof.

* * * * *